(12) United States Patent
Gray et al.

(10) Patent No.: US 12,311,034 B2
(45) Date of Patent: May 27, 2025

(54) FEEDBACK ENABLED SYNTHETIC GENES, TARGET SEED MATCH CASSETTES, AND THEIR USES

(71) Applicant: THE UNIVERSITY OF NORTH CAROLINA AT CHAPEL HILL, Chapel Hill, NC (US)

(72) Inventors: Steven James Gray, Southlake, TX (US); Sarah Sinnett, Farmers Branch, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 967 days.

(21) Appl. No.: 17/271,432

(22) PCT Filed: Aug. 29, 2019

(86) PCT No.: PCT/US2019/048776
§ 371 (c)(1),
(2) Date: Feb. 25, 2021

(87) PCT Pub. No.: WO2020/047234
PCT Pub. Date: Mar. 5, 2020

(65) Prior Publication Data
US 2021/0170051 A1 Jun. 10, 2021

Related U.S. Application Data

(60) Provisional application No. 62/861,044, filed on Jun. 13, 2019, provisional application No. 62/725,126, filed on Aug. 30, 2018.

(51) Int. Cl.
*A61K 48/00* (2006.01)
*A61P 25/28* (2006.01)
*C07K 14/47* (2006.01)

(52) U.S. Cl.
CPC ............ *A61K 48/005* (2013.01); *A61P 25/28* (2018.01); *C07K 14/4703* (2013.01)

(58) Field of Classification Search
CPC ..... C07K 14/475; A61P 25/00; C12N 5/0668; C12N 15/86; A61K 38/00
See application file for complete search history.

(56) References Cited

U.S. PATENT DOCUMENTS

| | | | |
|---|---|---|---|
| 4,501,729 A | 2/1985 | Boucher et al. | |
| 5,399,346 A | 3/1995 | Anderson et al. | |
| 7,195,916 B2 | 3/2007 | Qin et al. | |
| 7,201,898 B2 | 4/2007 | Monahan et al. | |
| 8,440,431 B2 | 5/2013 | Voytas et al. | |
| 8,871,445 B2 | 10/2014 | Cong et al. | |
| 8,889,356 B2 | 11/2014 | Zhang | |
| 10,000,772 B2 | 6/2018 | Doudna et al. | |
| 11,891,616 B2 * | 2/2024 | Gray | C12N 15/86 |
| 2013/0225666 A1 | 8/2013 | Kaspar et al. | |
| 2014/0200261 A1 * | 7/2014 | Hoge | A61P 35/00 |
| | | | 435/320.1 |

FOREIGN PATENT DOCUMENTS

| | | |
|---|---|---|
| JP | 2016504050 A | 2/2016 |
| WO | 0191803 A2 | 12/2001 |
| WO | 2009126563 A1 | 10/2009 |
| WO | 2018172795 A1 | 9/2018 |

OTHER PUBLICATIONS

Sinnett et al., Jun. 16, 2017, "Improved MECP2 Gene Therapy Extends the Survival of MeCP2-Null Mice without Apparent Toxicity after Intracisternal Delivery" Molecular Therapy Methods & Clinical Development, 5, p. 106-115 and Supplemental Information. (Year: 2017).*
Gadalla et al., 2013, "Improved Survival and Reduced Phenotypic Severity Following AAV9/MECP2 Gene Transfer to Neonatal and Juvenile Male Mecp2 Knockout Mice" Molecular Therapy, 21(1), p. 18-30 (Year: 2013).*
Guy et al., 2001, "A mouse Mecp2-null mutation causes neurological symptoms that mimic Rett syndrome" Nature Genetics, 27, p. 322-326 (Year: 2001).*
Sinnett, Boyle, et al., 2021, "Engineered microRNA-based regulatory element permits safe high-dose miniMECP2 gene therapy in Rett mice" Brain, 144, p. 3005-3019 (Year: 2021).*
Iqbal and Iqbal, 2014, "Human Epidermal Growth Factor Receptor 2 (HER2) in Cancers: Overexpression and Therapeutic Implications", Molecular Biology International, p. 1-9 (Year: 2014).*
Tabrizi et al., 2019, "Huntingtin Lowering Strategies for Disease Modification in Huntington's Disease", Neuron Review, p. 801-819 (Year: 2019).*
Chipman and Pasquinelli, 2019, "miRNA Targeting: Growing beyond the Seed", Trends in Genetics, 35(3), p. 215-255 (Year: 2019).*
Sætrom et al., 2007, "Distance constraints between microRNA target sites dictate efficacy and cooperativity" Nucleic Acids Research, 35(7), p. 2333-2342 (Year: 2007).*
Agarwal et al., 2015, "Predicting effective microRNA target sites in mammalian mRNAs" eLIFE, 4:e05005 (Year: 2015).*
Extended European Search Report corresponding to European Patent Application No. 19853521.3 (8 pages) (dated May 19, 2022).

(Continued)

*Primary Examiner* — Jennifer Dunston
*Assistant Examiner* — Jenna L Persons
(74) *Attorney, Agent, or Firm* — Myers Bigel, P.A.

(57) ABSTRACT

This invention relates to feedback-enabled synthetic genes, polynucleotide target cassettes, vectors, and pharmaceutical compositions for the purpose of providing transgene expression in target tissues that is capable of endogenous regulation for treating disorders such as dose-sensitive intellectual ability disorders, as well as methods of making and methods of using the same.

9 Claims, 20 Drawing Sheets
Specification includes a Sequence Listing.

(56) References Cited

OTHER PUBLICATIONS

Gadalla et al. "Development of a Novel AAV Gene Therapy Cassette with Improved Safety Features and Efficacy in a Mouse Model of Rett Syndrome" Molecular Therapy: Methods & Clinical Development, Supplemental Information, vol. 5 (8 pages) (2017).
Sinnett et al. "Engineered microRNA-based regulatory element permits safe high-dose miniMECP2 gene therapy in Rett mice" Bain, 144:3005-3019 (2021).
Zuo et al. "Specific Expression of MicroRNA in Different Tissues of Nervous System and Expression Changes in Nerve Regeneration" Sheng Li Ke Xue Jin Zhan, 42(4):261-268 (2011) (English translation of abstract).
International Preliminary Report on Patentability corresponding to International Application No. PCT/US2019/048776, dated Mar. 11, 2021, 10 pages.
Agarwal et al. "Predicting effective microRNA target sites in mammalian mRNAs" eLife, 4:e05005 (2015).
Araujo et al. "Cerebal overinhibition could be the basis for the high prevalence of epilepsy in persons with Down syndrome" Epilepsy & Behavior, 53:120-125 (2015) (Abstract only).
Berube et al. "Neurodevelopmental defects resulting from ATRX overexpression in transgenic mice" Human Molecular Genetics, 11(3):253-261 (2002).
Boettcher et al. "Choosing the Right Tool for the Job: RNAi, TALEN, or CRISPR" Molecular Cell, 58:575-585 (2015).
Bouazzi et al. "Novel ATRX gene damaging missense mutation c.6740A>C segregates with profound to severe Intellectual deficiency without alpha thalassaemia" Indian Journal of Medical Research, 143:43-48 (2016).
Carter et al. "Neuroanatomic correlates of autism and stereotypy in children with Down syndrome" NeuroReport, 19(6):653-656 (2008) (Abstract only).
Cesaretti et al. "Prenatal detection of 5q14.3 duplication including MEF2C and brain phenotype" American Journal of Medical Genetics, 170A(5):1352-1357 (2016) (Abstract only).
Copping et al. "Neuronal overexpression of Ube3a isoform 2 causes behavioral impairments and neuroanatomical pathology relevant to 15q11.2-q13.3 duplication syndrome" Human Molecular Genetics, 26(20):3995-4010 (2017).
De Queiroz et al. "Orofacial Findings and Dental Treatment in an 8-year-old Patient With Trisomy 18: A Case Report" Journal of Dentistry for Children, 74:67-72 (2007).
De Winter et al. "Phenotype and natural history in 101 individuals with Pitt-Hopkins syndrome through an internet questionnaire system" Orphanet Journal of Rare Diseases, 11(37):1-12 (2016).
Duchon et al. "DYRK1A, a Dosage-Sensitive Gene Involved in Neurodevelopmental Disorders, Is a Target for Drug Development in Down Syndrome" Frontiers in Behavioral Neuroscience, 10(104):1-17 (2016).
Fuertes-Gonzalez et al. "Oral findings in Rett syndrome: A systematic review of the dental literature" Med Oral Patol Oral Cir Bucal, 16(1):e37-41 (2011).
Gadalla et al. "Development of a Novel AAV Gene Therapy Cassette with Improved Safety Features and Efficacy in a Mouse Model of Rett Syndrome" Molecular Therapy: Methods & Clinical Development, 5:180-190 (2017).
Grimson et al. "MicroRNA Targeting Specificity in Mammals: Determinants beyond Seed Pairing" Molecular Cell, 27:91-105 (2007).
Guedj et al. "DYRK1A: a master regulatory protein controlling brain growth" Neurobiology of Disease, 46(1):190-203 (2012) (Abstract only).
Hassan et al. "miR-218 Directs a Wnt Signaling Circuit to Promote Differentiation of Osteoblasts and Osteomimicry of Metastatic Cancer Cells" Journal of Biological Chemistry, 287(50):42084-42092 (2012).
Hegarty et al. "Zeb2: A multifunctional regulator of nervous system development" Progress in Neurobiology, 132:81-95 (2015) (Abstract only).
Kalsotra et al. "The Mef2 transcription network is disrupted in myotonic dystrophy heart tissue dramatically altering miRNA and mRNA expression" Cell Reports, 6(2):336-345 (2014).
Kent et al. "Speech Impairment in Down Syndrome: A Review" Journal of Speech, Language, and Hearing Research, 56(1):178-210 (2013).
Leonard et al. "Clinical and biological progress over 50 years in Rett syndrome" Nature Reviews Neurology, 13:37-51 (2017).
Lewis et al. "Conserved Seed Pairing, Often Flanked by Adenosines, Indicates that Thousands of Human Genes are MicroRNA Targets" Cell, 120:15-20 (2005).
Luco et al. "Case report of novel DYRK1A mutations in 2 individuals with syndromic intellectual disability and a review of the literature" BMC Medical Genetics, 17(15):1-8 (2016).
Lugtenberg et al. "Xq13.2q21.1 duplication encompassing the ATRX gene in a man with mental retardation, minor facial and genital anomalies, short stature and broad thorax" American Journal of Medical Genetics, 149A(4):760-766 (2009) (Abstract only).
Matsumoto et al. "An Xp22.12 microduplication including RPS6KA3 identified in a family with variably affected intellectual and behavioral disabilities" Journal of Human Genetics, 58:755-757 (2013).
Miguet et al. "Further delineation of the MECP2 duplication syndrome phenotype in 59 French male patients, with a particular focus on morphological and neurological features" Journal of Medical Genetics, 55:359-371 (2018).
Miyata et al. "Periventricular small cystic lesions in a patient with Coffin-Lowry syndrome who exhibited a novel mutation in the RPS6KA3 gene" Brain and Development, 40(7):566-569 (2018) (Abstract only).
Morino et al. "Eight years of follow-up after laminectomy of calcium pyrophosphate crystal deposition in the cervical yellow ligament of patient with Coffin-Lowry syndrome" Medicine, 95(31):e4468 (2016).
Mullegama et al. "Reciprocal deletion and duplication at 2q23.1 indicates a role for MBD5 in autism spectrum disorder" European Journal of Human Genetics, 22:57-63 (2014).
Pelc et al. "Behavior and neuropsychiatric manifestations in Angelman syndrome" Neuropsychiatric Disease and Treatment. 4(3):577-584 (2008).
Pelc et al. "Are there distinctive sleep problems in Angelman syndrome?" Sleep Medicine, 9(4):434-441 (2008) (Abstract only).
Roberts et al. "Anatomy of trisomy 18" Clinical Anatomy, 29(5):628-632 (2016) (Abstract only).
Rosenfeld et al. "Further Evidence of Contrasting Phenotypes Caused by Reciprocal Deletions and Duplications: Duplication of NSD1 Causes Growth Retardation and Microcephaly" Molecular Syndromology, 3:247-254 (2012).
Schirle et al. "Structural Basis for microRNA Targeting" Science, 346(6209):608-613 (2014).
Schirle et al. "Water-mediated recognition of t1-adenosine anchors Argonaute2 to microRNA targets" eLife, 4:e07646 (2015).
Seltzer et al. "Genetic disorders associated with postnatal microcephaly" American Journal of Medical Genetics Part C, Seminars in Medical Genetics, 166C(2):140-155 (2014) (Abstract only).
Sinnett et al. "Improved MECP2 Gene Therapy Extends the Survival of MeCP2-Null Mice without Apparent Toxicity after Intracisternal Delivery" Molecular Therapy: Methods & Clinical Development, 5:106-115 (2017).
Talkowski et al. "Assessment of 2q23.1 Microdeletion Syndrome Implicates MBD5 as a Single Causal Locus of Intellectual Disability, Epilepsy, and Autism Spectrum Disorder" American Journal of Human Genetics, 89:551-563 (2011).
Tejada et al. "A Child With Mild X-Linked Intellectual Disability and a Microduplication at Xp22.12 Including RPS6KA3" 128:e1029-e1033 (2011).
Tillotson et al. "Radically truncated MeCP2 rescues Rett syndrome-like neurological defects" Nature, 550(7676):398-401 (2017).

(56) References Cited

OTHER PUBLICATIONS

Tos et al. "A familial case of Coffin-Lowry syndrome caused by RPS6KA3 C.898C>T mutation associated with multiple abnormal brain imaging findings" Genetic Counseling, 26(1):47-52 (2015) (Abstract only).

Touraine et al. "A syndromic form of X-linked mental retardation: the Coffin-Lowry syndrome" European Journal of Pediatrics, 161:179-187 (2002).

Urdinguio et al. "Disrupted microRNA expression caused by Mecp2 loss in a mouse model of Rett syndrome" Epigenetics, 5(7):656-663 (2010).

Vrecar et al. "Further Clinical Delineation of the MEF2C Haploinsufficiency Syndrome" Journal of Pediatric Genetics, 6:129-141 (2017).

Wegiel et al. "Differences Between the Pattern of Developmental Abnormalities in Autism Associated With Duplications 15q11.2-q13 and Idiopathic Autism" Journal of Neuropathology & Experimental Neurology, 71(5):382-397 (2012).

Wu et al. "Genome-wide analysis reveals methyl-CpG-binding protein 2-dependent regulation of microRNAs in a mouse model of Rett syndrome" Proceedings of the National Academy of Sciences USA, 107(42):18161-18166 (2010).

Yuan et al. "A de novo triplication on 2q22.3 including the entire ZEB2 gene associated with global developmental delay, multiple congenital anomalies and behavioral abnormalities" Molecular Cytogenetics, 8(99):1-7 (2015).

Gadalla K.K.E. et al. "Development of a novel AAV gene therapy cassette with improved safety features and efficacy in a mouse model of Rett syndrome" Molecular Therapy: Methods & Clinical Development, 5:180-190 2017.

Gadalla, K. K. E. et al., "Improved survival and reduced phenotypic severity following AAV9/MECP2 gene transfer to neonatal and juvenile male Mecp2 knockout mice", Molecular Therapy, 21(1):18-30 2013.

International Search Report and Written Opinion corresponding to International Application No. PCT/US2019/048776, dated Dec. 17, 2019 14 pages.

McGowan H et al. "Regulatory functions and pathological relevance of the MECP2 3' UTR in the central nervous system" Cell Regeneration, 4(1):1-10 2015.

Sinnett S.E. et al. "Improved MECP2 gene therapy extends the survival of MeCP2-null mice without apparent toxicity after intracisternal delivery" Molecular Therapy: Methods & Clinical Development, 5:106-115 2017.

Muniategui et al. "Joint analysis of miRNA and mRNA expression data" Briefings in Bioinformatics, 14(3):263-278 (2013).

\* cited by examiner

| MOUSE ID (TREATMENT) | NORMALIZED MYC INTENSITY IN GFP(+) CELLS | |
|---|---|---|
| | AVERAGED ACROSS Z-STACKS | AVERAGED ACROSS ALL MICE |
| #91 (V2-T1) | 0.83 (6 STACKS) | 0.87 |
| #88 (V2-T1) | 0.91 (3 STACKS) | |
| #96 (V2) | 1.01 (5 STACKS) | 1.04 |
| #99 (V2) | 0.88 (5 STACKS) | |
| #03 (V2) | 1.23 (5 STACKS) | |

| VECTORS | WT MOUSE ID# | MEAN MECP2 INTENSITY ± SEM, NORMALIZED TO MYC(-) CELLS | |
|---|---|---|---|
| PUBLISHED/ NEGATIVE CONTROL | 126 | 4.1±0.5 | 5.0±0.7 |
| | 127 | 4.5±0.4 | |
| | 133 | 6.4±0.9 | |
| NEURONAL KNOCKDOWN | 123 | 3.6±0.4 | 2.7±0.5, P=0.06 |
| | 124 | 1.9±0.2 | |
| | 130 | 2.6±0.2 | |
| REG1 | 121 | 2.3±0.1 | 2.6±0.3, *p=0.02 |
| | 122 | 3.3±0.4 | |
| | 128 | 2.6±0.1 | |
| | 129 | 2.2±0.2 | |

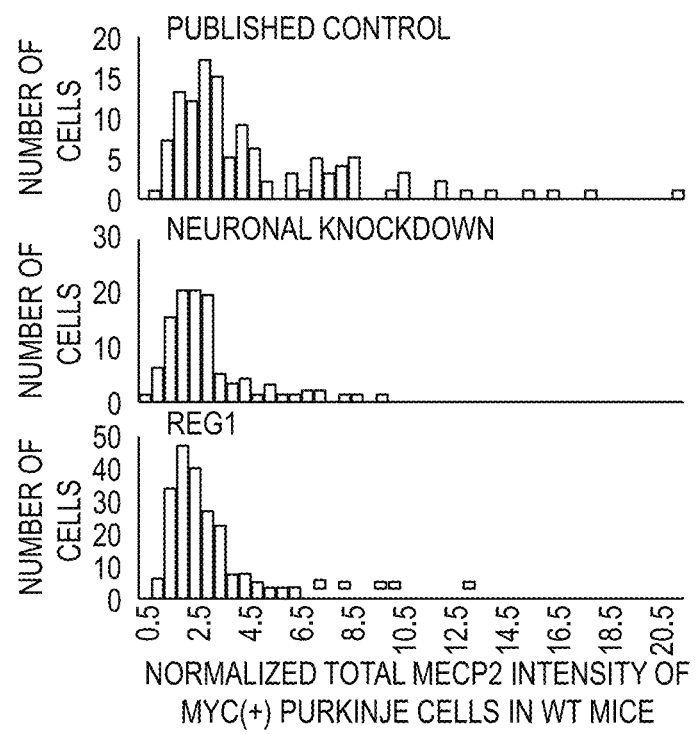
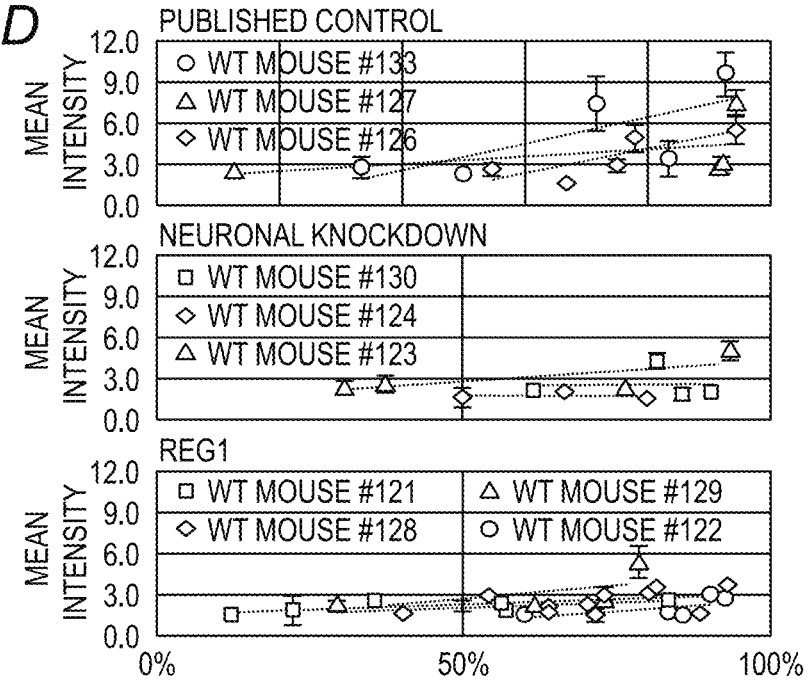
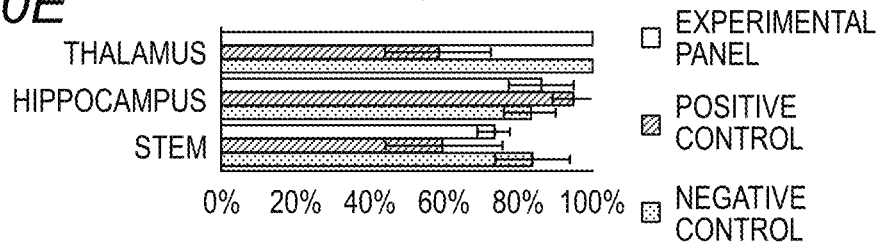

SEQUENCE LISTING

<160> NUMBER OF SEQ ID NOS: 109

<210> SEQ ID NO 1
<211> LENGTH: 175
<212> TYPE: DNA
<213> ORGANISM: artificial
<220> FEATURE:
<223> OTHER INFORMATION: Reg2

<400> SEQUENCE: 1
ctgttctagc ccccaaagag ttttctgtgc ttgcttttga aacttgaagt cttgaaaacc    60
aaagacatag atgtgaaaat tttaggcagt gtaagctgat agcacaagtt ctggcgactc   120
acaattatgc tgtgaatttt acaaaaagaa gcagtaatct acctcagccg ataac        175

<210> SEQ ID NO 2
<211> LENGTH: 87
<212> TYPE: DNA
<213> ORGANISM: artificial
<220> FEATURE:
<223> OTHER INFORMATION: Reg1

<400> SEQUENCE: 2
ataagggcag aaacggttca cattccattc tgccccggac ctacctccct ccctctcctt    60
atcaaaccct agccttgctt gttaaat                                        87

<210> SEQ ID NO 3
<211> LENGTH: 11
<212> TYPE: RNA
<213> ORGANISM: Homo sapiens

<400> SEQUENCE: 3
cuccuggcac u                                                         11

<210> SEQ ID NO 4
<211> LENGTH: 12
<212> TYPE: RNA
<213> ORGANISM: Homo sapiens

<400> SEQUENCE: 4
gacacuuauc ca                                                        12

<210> SEQ ID NO 5
<211> LENGTH: 12
<212> TYPE: RNA
<213> ORGANISM: Homo sapiens

<400> SEQUENCE: 5
cuguucuagc cc                                                        12

<210> SEQ ID NO 6
<211> LENGTH: 11
<212> TYPE: RNA
<213> ORGANISM: Homo sapiens

<400> SEQUENCE: 6
guuuucugug c                                                         11

<210> SEQ ID NO 7
<211> LENGTH: 11
<212> TYPE: RNA
<213> ORGANISM: Homo sapiens

<400> SEQUENCE: 7

```
uaauuuauug u                                                    11

<210> SEQ ID NO 8
<211> LENGTH: 12
<212> TYPE: RNA
<213> ORGANISM: Homo sapiens

<400> SEQUENCE: 8 cuguuuuau ag                                                    12

<210> SEQ ID NO 9
<211> LENGTH: 11
<212> TYPE: RNA
<213> ORGANISM: Homo sapiens

<400> SEQUENCE: 9
aauauguuuu a                                                    11

<210> SEQ ID NO 10
<211> LENGTH: 11
<212> TYPE: RNA
<213> ORGANISM: Homo sapiens

<400> SEQUENCE: 10
uguggagcaa u                                                    11

<210> SEQ ID NO 11
<211> LENGTH: 12
<212> TYPE: RNA
<213> ORGANISM: Homo sapiens

<400> SEQUENCE: 11
cauuugcauu ag                                                   12

<210> SEQ ID NO 12
<211> LENGTH: 11
<212> TYPE: RNA
<213> ORGANISM: Homo sapiens

<400> SEQUENCE: 12
gauaagaaca u                                                    11

<210> SEQ ID NO 13
<211> LENGTH: 11
<212> TYPE: RNA
<213> ORGANISM: Homo sapiens

<400> SEQUENCE: 13
ggggaaaaaa c                                                    11

<210> SEQ ID NO 14
<211> LENGTH: 11
<212> TYPE: RNA
<213> ORGANISM: Homo sapiens

<400> SEQUENCE: 14
auucacaugg g                                                    11

<210> SEQ ID NO 15
<211> LENGTH: 12
<212> TYPE: RNA
<213> ORGANISM: Homo sapiens
```

```
<400> SEQUENCE: 15
uuuaugaaau uu                                                          12

<210> SEQ ID NO 16
<211> LENGTH: 11
<212> TYPE: RNA
<213> ORGANISM: Homo sapiens

<400> SEQUENCE: 16
uuuugguuga u                                                           11

<210> SEQ ID NO 17
<211> LENGTH: 12
<212> TYPE: DNA
<213> ORGANISM: artificial
<220> FEATURE:
<223> OTHER INFORMATION: vg miR-9-5p target 5' flanking

<400> SEQUENCE: 17
ctgttctagc cc                                                          12

<210> SEQ ID NO 18
<211> LENGTH: 11
<212> TYPE: DNA
<213> ORGANISM: artificial
<220> FEATURE:
<223> OTHER INFORMATION: vg miR-9-5p target 3' flanking

<400> SEQUENCE: 18
gttttctgtg c                                                           11

<210> SEQ ID NO 19
<211> LENGTH: 11
<212> TYPE: RNA
<213> ORGANISM: Homo sapiens

<400> SEQUENCE: 19
aggcuugcag a                                                           11

<210> SEQ ID NO 20
<211> LENGTH: 11
<212> TYPE: RNA
<213> ORGANISM: Homo sapiens

<400> SEQUENCE: 20
gccugcuccu u                                                           11

<210> SEQ ID NO 21
<211> LENGTH: 11
<212> TYPE: RNA
<213> ORGANISM: Homo sapiens

<400> SEQUENCE: 21
uugcuuuuga a                                                           11

<210> SEQ ID NO 22
<211> LENGTH: 11
<212> TYPE: RNA
<213> ORGANISM: Homo sapiens

<400> SEQUENCE: 22
gucuugaaaa c                                                           11
```

```
<210> SEQ ID NO 23
<211> LENGTH: 11
<212> TYPE: RNA
<213> ORGANISM: Homo sapiens

<400> SEQUENCE: 23
uuuuuuuuuu a                                                            11

<210> SEQ ID NO 24
<211> LENGTH: 11
<212> TYPE: RNA
<213> ORGANISM: Homo sapiens

<400> SEQUENCE: 24
aagauugcaa a                                                            11

<210> SEQ ID NO 25
<211> LENGTH: 11
<212> TYPE: RNA
<213> ORGANISM: Homo sapiens

<400> SEQUENCE: 25
aagaagaagc c                                                            11

<210> SEQ ID NO 26
<211> LENGTH: 11
<212> TYPE: RNA
<213> ORGANISM: Homo sapiens

<400> SEQUENCE: 26
cccucaauaa a                                                            11

<210> SEQ ID NO 27
<211> LENGTH: 11
<212> TYPE: RNA
<213> ORGANISM: Homo sapiens

<400> SEQUENCE: 27
gagguugaga c                                                            11

<210> SEQ ID NO 28
<211> LENGTH: 11
<212> TYPE: RNA
<213> ORGANISM: Homo sapiens

<400> SEQUENCE: 28
cucaggcaga g                                                            11

<210> SEQ ID NO 29
<211> LENGTH: 11
<212> TYPE: RNA
<213> ORGANISM: Homo sapiens

<400> SEQUENCE: 29
acaauuuugg u                                                            11

<210> SEQ ID NO 30
<211> LENGTH: 11
<212> TYPE: RNA
<213> ORGANISM: Homo sapiens

<400> SEQUENCE: 30
uuguuaaaga a                                                            11
```

```
<210> SEQ ID NO 31
<211> LENGTH: 11
<212> TYPE: RNA
<213> ORGANISM: Homo sapiens

<400> SEQUENCE: 31
aaaagaaaac a                                                          11

<210> SEQ ID NO 32
<211> LENGTH: 11
<212> TYPE: RNA
<213> ORGANISM: Homo sapiens

<400> SEQUENCE: 32
cauuuucaau a                                                          11

<210> SEQ ID NO 33
<211> LENGTH: 11
<212> TYPE: RNA
<213> ORGANISM: Homo sapiens

<400> SEQUENCE: 33
ucugugaagg a                                                          11

<210> SEQ ID NO 34
<211> LENGTH: 11
<212> TYPE: RNA
<213> ORGANISM: Homo sapiens

<400> SEQUENCE: 34
gugaugcaug u                                                          11

<210> SEQ ID NO 35
<211> LENGTH: 11
<212> TYPE: RNA
<213> ORGANISM: Homo sapiens

<400> SEQUENCE: 35
uuucucaugg g                                                          11

<210> SEQ ID NO 36
<211> LENGTH: 11
<212> TYPE: RNA
<213> ORGANISM: Homo sapiens

<400> SEQUENCE: 36
guggacucau c                                                          11

<210> SEQ ID NO 37
<211> LENGTH: 11
<212> TYPE: DNA
<213> ORGANISM: artificial
<220> FEATURE:
<223> OTHER INFORMATION: vg miR-26-5p target 5' flanking

<400> SEQUENCE: 37
ttgcttttga a                                                          11

<210> SEQ ID NO 38
<211> LENGTH: 11
<212> TYPE: DNA
<213> ORGANISM: artificial
<220> FEATURE:
<223> OTHER INFORMATION: vg miR-26-5p target 3' flanking
```

-continued

```
<400> SEQUENCE: 38
gtcttgaaaa c                                                           11

<210> SEQ ID NO 39
<211> LENGTH: 11
<212> TYPE: RNA
<213> ORGANISM: Homo sapiens

<400> SEQUENCE: 39
uuuuuuaaua c                                                           11

<210> SEQ ID NO 40
<211> LENGTH: 11
<212> TYPE: RNA
<213> ORGANISM: Homo sapiens

<400> SEQUENCE: 40
agcaaagaau a                                                           11

<210> SEQ ID NO 41
<211> LENGTH: 11
<212> TYPE: RNA
<213> ORGANISM: Homo sapiens

<400> SEQUENCE: 41
aaacaaaaag c                                                           11

<210> SEQ ID NO 42
<211> LENGTH: 11
<212> TYPE: RNA
<213> ORGANISM: Homo sapiens

<400> SEQUENCE: 42
agugcacuua a                                                           11

<210> SEQ ID NO 43
<211> LENGTH: 11
<212> TYPE: RNA
<213> ORGANISM: Homo sapiens

<400> SEQUENCE: 43
aacacuaugu a                                                           11

<210> SEQ ID NO 44
<211> LENGTH: 11
<212> TYPE: RNA
<213> ORGANISM: Homo sapiens

<400> SEQUENCE: 44
uggaaacuug g                                                           11

<210> SEQ ID NO 45
<211> LENGTH: 11
<212> TYPE: RNA
<213> ORGANISM: Homo sapiens

<400> SEQUENCE: 45
ccuucucuug g                                                           11

<210> SEQ ID NO 46
<211> LENGTH: 11
<212> TYPE: RNA
```

```
<213> ORGANISM: Homo sapiens

<400> SEQUENCE: 46
gaucugucga u                                                        11

<210> SEQ ID NO 47
<211> LENGTH: 11
<212> TYPE: RNA
<213> ORGANISM: Homo sapiens

<400> SEQUENCE: 47
uuuccaaagg g                                                        11

<210> SEQ ID NO 48
<211> LENGTH: 11
<212> TYPE: RNA
<213> ORGANISM: Homo sapiens

<400> SEQUENCE: 48
uuggagugaa a                                                        11

<210> SEQ ID NO 49
<211> LENGTH: 11
<212> TYPE: RNA
<213> ORGANISM: Homo sapiens

<400> SEQUENCE: 49
caaagacaua g                                                        11

<210> SEQ ID NO 50
<211> LENGTH: 11
<212> TYPE: RNA
<213> ORGANISM: Homo sapiens

<400> SEQUENCE: 50
aauuuuaggc a                                                        11

<210> SEQ ID NO 51
<211> LENGTH: 11
<212> TYPE: RNA
<213> ORGANISM: Homo sapiens

<400> SEQUENCE: 51
cagcugguuc c                                                        11

<210> SEQ ID NO 52
<211> LENGTH: 12
<212> TYPE: RNA
<213> ORGANISM: Homo sapiens

<400> SEQUENCE: 52
cugaguguuc uc                                                       12

<210> SEQ ID NO 53
<211> LENGTH: 11
<212> TYPE: RNA
<213> ORGANISM: Homo sapiens

<400> SEQUENCE: 53
aaguaagaaa a                                                        11

<210> SEQ ID NO 54
<211> LENGTH: 11
```

```
<212> TYPE: RNA
<213> ORGANISM: Homo sapiens

<400> SEQUENCE: 54
acaaauguag a                                                        11

<210> SEQ ID NO 55
<211> LENGTH: 11
<212> TYPE: RNA
<213> ORGANISM: Homo sapiens

<400> SEQUENCE: 55
uuaugacaua u                                                        11

<210> SEQ ID NO 56
<211> LENGTH: 11
<212> TYPE: RNA
<213> ORGANISM: Homo sapiens

<400> SEQUENCE: 56
cacaucacaa a                                                        11

<210> SEQ ID NO 57
<211> LENGTH: 11
<212> TYPE: RNA
<213> ORGANISM: Homo sapiens

<400> SEQUENCE: 57
auuugguuca c                                                        11

<210> SEQ ID NO 58
<211> LENGTH: 11
<212> TYPE: RNA
<213> ORGANISM: Homo sapiens

<400> SEQUENCE: 58
gugcccucca u                                                        11

<210> SEQ ID NO 59
<211> LENGTH: 11
<212> TYPE: DNA
<213> ORGANISM: artificial
<220> FEATURE:
<223> OTHER INFORMATION: vg miR-23-3p target 5' flanking

<400> SEQUENCE: 59
caaagacata g                                                        11

<210> SEQ ID NO 60
<211> LENGTH: 11
<212> TYPE: DNA
<213> ORGANISM: artificial
<220> FEATURE:
<223> OTHER INFORMATION: vg miR-23-3p target 3' flanking

<400> SEQUENCE: 60
aattttaggc a                                                        11

<210> SEQ ID NO 61
<211> LENGTH: 11
<212> TYPE: RNA
<213> ORGANISM: Homo sapiens

<400> SEQUENCE: 61
```
uucuuaccga c                                                                11

<210> SEQ ID NO 62
<211> LENGTH: 12
<212> TYPE: RNA
<213> ORGANISM: Homo sapiens

<400> SEQUENCE: 62
gucagguuga ag                                                               12

<210> SEQ ID NO 63
<211> LENGTH: 12
<212> TYPE: RNA
<213> ORGANISM: Homo sapiens

<400> SEQUENCE: 63
aacuuuagua ac                                                               12

<210> SEQ ID NO 64
<211> LENGTH: 11
<212> TYPE: RNA
<213> ORGANISM: Homo sapiens

<400> SEQUENCE: 64
caaauuaaaa a                                                                11

<210> SEQ ID NO 65
<211> LENGTH: 11
<212> TYPE: RNA
<213> ORGANISM: Homo sapiens

<400> SEQUENCE: 65
uuaaugagaa g                                                                11

<210> SEQ ID NO 66
<211> LENGTH: 11
<212> TYPE: RNA
<213> ORGANISM: Homo sapiens

<400> SEQUENCE: 66
uuuugauuuu g                                                                11

<210> SEQ ID NO 67
<211> LENGTH: 11
<212> TYPE: RNA
<213> ORGANISM: Homo sapiens

<400> SEQUENCE: 67
gcacgaauau a                                                                11

<210> SEQ ID NO 68
<211> LENGTH: 12
<212> TYPE: RNA
<213> ORGANISM: Homo sapiens

<400> SEQUENCE: 68
ucucuuaacu gc                                                               12

<210> SEQ ID NO 69
<211> LENGTH: 12
<212> TYPE: RNA
<213> ORGANISM: Homo sapiens

<400> SEQUENCE: 69

```
guguaagcug au                                                    12

<210> SEQ ID NO 70
<211> LENGTH: 11
<212> TYPE: RNA
<213> ORGANISM: Homo sapiens

<400> SEQUENCE: 70
guucuggcga c                                                     11

<210> SEQ ID NO 71
<211> LENGTH: 12
<212> TYPE: RNA
<213> ORGANISM: Homo sapiens

<400> SEQUENCE: 71
aauaagaaau gu                                                    12

<210> SEQ ID NO 72
<211> LENGTH: 11
<212> TYPE: RNA
<213> ORGANISM: Homo sapiens

<400> SEQUENCE: 72
cauaauuuuc c                                                     11

<210> SEQ ID NO 73
<211> LENGTH: 11
<212> TYPE: RNA
<213> ORGANISM: Homo sapiens

<400> SEQUENCE: 73
auuuauacuu u                                                     11

<210> SEQ ID NO 74
<211> LENGTH: 11
<212> TYPE: RNA
<213> ORGANISM: Homo sapiens

<400> SEQUENCE: 74
cuagaaaauu g                                                     11

<210> SEQ ID NO 75
<211> LENGTH: 11
<212> TYPE: RNA
<213> ORGANISM: Homo sapiens

<400> SEQUENCE: 75
ucagcauaaa c                                                     11

<210> SEQ ID NO 76
<211> LENGTH: 11
<212> TYPE: RNA
<213> ORGANISM: Homo sapiens

<400> SEQUENCE: 76
aaauuuaguc u                                                     11

<210> SEQ ID NO 77
<211> LENGTH: 12
<212> TYPE: DNA
<213> ORGANISM: artificial
<220> FEATURE:
```

```
<223> OTHER INFORMATION: vg miR-218-5p target 5' flanking

<400> SEQUENCE: 77
gtgtaagctg at                                                          12

<210> SEQ ID NO 78
<211> LENGTH: 11
<212> TYPE: DNA
<213> ORGANISM: artificial
<220> FEATURE:
<223> OTHER INFORMATION: vg miR-218-5p target 3' flanking

<400> SEQUENCE: 78
gttctggcga c                                                           11

<210> SEQ ID NO 79
<211> LENGTH: 11
<212> TYPE: RNA
<213> ORGANISM: Homo sapiens

<400> SEQUENCE: 79
gauaaaucuc u                                                           11

<210> SEQ ID NO 80
<211> LENGTH: 11
<212> TYPE: RNA
<213> ORGANISM: Homo sapiens

<400> SEQUENCE: 80
ucacaauuau g                                                           11

<210> SEQ ID NO 81
<211> LENGTH: 11
<212> TYPE: RNA
<213> ORGANISM: Homo sapiens

<400> SEQUENCE: 81
uuuuacaaaa a                                                           11

<210> SEQ ID NO 82
<211> LENGTH: 11
<212> TYPE: RNA
<213> ORGANISM: Homo sapiens

<400> SEQUENCE: 82
uuuaaaaaaa u                                                           11

<210> SEQ ID NO 83
<211> LENGTH: 11
<212> TYPE: RNA
<213> ORGANISM: Homo sapiens

<400> SEQUENCE: 83
auuaacaugc u                                                           11

<210> SEQ ID NO 84
<211> LENGTH: 11
<212> TYPE: RNA
<213> ORGANISM: Homo sapiens

<400> SEQUENCE: 84
ucaugaaaua a                                                           11
```

```
<210> SEQ ID NO 85
<211> LENGTH: 11
<212> TYPE: RNA
<213> ORGANISM: Homo sapiens

<400> SEQUENCE: 85 uuugggggggg g                                                              11

<210> SEQ ID NO 86
<211> LENGTH: 11
<212> TYPE: RNA
<213> ORGANISM: Homo sapiens

<400> SEQUENCE: 86
aaaucauaca g                                                               11

<210> SEQ ID NO 87
<211> LENGTH: 11
<212> TYPE: RNA
<213> ORGANISM: Homo sapiens

<400> SEQUENCE: 87
gacuugccuu u                                                               11

<210> SEQ ID NO 88
<211> LENGTH: 11
<212> TYPE: RNA
<213> ORGANISM: Homo sapiens

<400> SEQUENCE: 88
acaaaccuaa a                                                               11

<210> SEQ ID NO 89
<211> LENGTH: 11
<212> TYPE: RNA
<213> ORGANISM: Homo sapiens

<400> SEQUENCE: 89
gccauuguaa a                                                               11

<210> SEQ ID NO 90
<211> LENGTH: 11
<212> TYPE: RNA
<213> ORGANISM: Homo sapiens

<400> SEQUENCE: 90
uuuuuuuuuu u                                                               11

<210> SEQ ID NO 91
<211> LENGTH: 11
<212> TYPE: RNA
<213> ORGANISM: Homo sapiens

<400> SEQUENCE: 91
ggaacuugaa g                                                               11

<210> SEQ ID NO 92
<211> LENGTH: 11
<212> TYPE: RNA
<213> ORGANISM: Homo sapiens

<400> SEQUENCE: 92
uuggggcuuu c                                                               11
```

```
<210> SEQ ID NO 93
<211> LENGTH: 11
<212> TYPE: RNA
<213> ORGANISM: Homo sapiens

<400> SEQUENCE: 93
auguaugaac a                                                              11

<210> SEQ ID NO 94
<211> LENGTH: 11
<212> TYPE: DNA
<213> ORGANISM: artificial
<220> FEATURE:
<223> OTHER INFORMATION: vg miR-27a-3p target 5' flanking

<400> SEQUENCE: 94
tcacaattat g                                                              11

<210> SEQ ID NO 95
<211> LENGTH: 11
<212> TYPE: DNA
<213> ORGANISM: artificial
<220> FEATURE:
<223> OTHER INFORMATION: vg miR-27a-3p target 3' flanking

<400> SEQUENCE: 95
ttttacaaaa a                                                              11

<210> SEQ ID NO 96
<211> LENGTH: 11
<212> TYPE: RNA
<213> ORGANISM: Homo sapiens

<400> SEQUENCE: 96
guuguuaguu a                                                              11

<210> SEQ ID NO 97
<211> LENGTH: 11
<212> TYPE: RNA
<213> ORGANISM: Homo sapiens

<400> SEQUENCE: 97
cucuccugac a                                                              11

<210> SEQ ID NO 98
<211> LENGTH: 11
<212> TYPE: RNA
<213> ORGANISM: Homo sapiens

<400> SEQUENCE: 98
gaagcaguaa u                                                              11

<210> SEQ ID NO 99
<211> LENGTH: 11
<212> TYPE: RNA
<213> ORGANISM: Homo sapiens

<400> SEQUENCE: 99
ugccgauaac c                                                              11

<210> SEQ ID NO 100
<211> LENGTH: 12
<212> TYPE: RNA
<213> ORGANISM: Homo sapiens
```

```
<400> SEQUENCE: 100
caaauugauu ca                                                        12

<210> SEQ ID NO 101
<211> LENGTH: 11
<212> TYPE: RNA
<213> ORGANISM: Homo sapiens

<400> SEQUENCE: 101
guuuaauuca g                                                         11

<210> SEQ ID NO 102
<211> LENGTH: 11
<212> TYPE: RNA
<213> ORGANISM: Homo sapiens

<400> SEQUENCE: 102
ucugccccuc u                                                         11

<210> SEQ ID NO 103
<211> LENGTH: 11
<212> TYPE: RNA
<213> ORGANISM: Homo sapiens

<400> SEQUENCE: 103
uuccacucau g                                                         11

<210> SEQ ID NO 104
<211> LENGTH: 11
<212> TYPE: RNA
<213> ORGANISM: Homo sapiens

<400> SEQUENCE: 104
cacugugugu g                                                         11

<210> SEQ ID NO 105
<211> LENGTH: 11
<212> TYPE: RNA
<213> ORGANISM: Homo sapiens

<400> SEQUENCE: 105
gugaccuuuu a                                                         11

<210> SEQ ID NO 106
<211> LENGTH: 11
<212> TYPE: RNA
<213> ORGANISM: Homo sapiens

<400> SEQUENCE: 106
gagccuacuu c                                                         11

<210> SEQ ID NO 107
<211> LENGTH: 11
<212> TYPE: RNA
<213> ORGANISM: Homo sapiens

<400> SEQUENCE: 107
uuaaggcacu u                                                         11

<210> SEQ ID NO 108
<211> LENGTH: 11
<212> TYPE: DNA
```

-continued

```
<213> ORGANISM: artificial
<220> FEATURE:
<223> OTHER INFORMATION: vg let-7e/98-5p target 5' flanking

<400> SEQUENCE: 108
gaagcagtaa t                                                          11

<210> SEQ ID NO 109
<211> LENGTH: 11
<212> TYPE: DNA
<213> ORGANISM: artificial
<220> FEATURE:
<223> OTHER INFORMATION: vg let-7e/98-5p target 3' flanking

<400> SEQUENCE: 109
agccgataac c                                                          11
```

FEEDBACK ENABLED SYNTHETIC GENES, TARGET SEED MATCH CASSETTES, AND THEIR USES

STATEMENT OF PRIORITY

This patent application is a 35 U.S.C. § 371 national phase application of PCT Application PCT/US2019/048776 filed Aug. 29, 2019, which claims the benefit, under 35 U.S.C. § 119(e), of U.S. Provisional Applications No. 62/725,126, filed on Aug. 30, 2018, and No. 62/861,044, filed on Jun. 13, 2019, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-844_ST25.txt, 17,424 bytes in size, generated on Feb. 9, 2021 and filed via EFS-Web, is provided in lieu of a paper copy. This Sequence Listing is hereby incorporated herein by reference into the specification for its disclosures.

FIELD OF THE INVENTION

This invention relates to feedback-enabled synthetic genes, polynucleotide target cassettes, vectors, and pharmaceutical compositions for the purpose of providing transgene expression in target tissues that is capable of endogenous regulation for treating disorders such as dose-sensitive intellectual ability disorders, as well as methods of making and methods of using the same.

BACKGROUND OF THE INVENTION

A number of neurodevelopmental disorders characterized by intellectual disability are mediated by mutations in genes that must be tightly regulated (see Table 1). Expression of endogenous gene products is carefully regulated in both target and non-target tissues through known and as-yet-unknown molecular mechanisms. There are negative outcomes in current gene therapies of over- and under-expression of the gene products from gene therapy vectors in target tissues with improper or incomplete regulation. Thus, there is a need in the art for vectors with improved regulation of expression. The present invention overcomes shortcomings in the art by providing feedback-enabled synthetic genes, polynucleotide target cassettes, vectors, and pharmaceutical compositions for the purpose of providing transgene expression in target tissues that is capable of endogenous regulation for treating disorders such as dose-sensitive intellectual ability disorders.

SUMMARY OF THE INVENTION

The present invention is based, in part, on the development of feedback-enabled synthetic genes, polynucleotide target cassettes, vectors, and pharmaceutical compositions for the purpose of providing transgene expression in target tissues that is capable of endogenous regulation for treating disorders such as dose-sensitive intellectual ability disorders such as Rett Syndrome (RTT). This invention was made in part with support from the Rett Syndrome Research Trust.

Thus, one aspect of the invention relates to a synthetic gene comprising a polynucleotide comprising a coding region encoding a protein or nucleic acid of interest and one or more regulatory regions, wherein the polynucleotide further comprises one or more nucleic acid segments each comprising a seed match identified as a binding site for an endogenous miRNA and a 5' flanking sequence and a 3' flanking sequence neighboring said seed match, wherein said one or more nucleic acid segments are inserted into a regulatory region of said polynucleotide such that expression of said protein or nucleic acid of interest when said synthetic gene is delivered to a cell expressing the endogenous miRNA is reduced relative to expression of a protein or nucleic acid of interest when a synthetic gene that does not comprise the one or more nucleic acid segments is delivered to a cell expressing the endogenous miRNA.

A further aspect of the invention relates to vectors and pharmaceutical compositions comprising the synthetic gene of the present invention.

Another aspect of the invention relates to a polynucleotide target cassette for providing dose dependent inhibitory feedback to the synthetic gene of the present invention.

An additional aspect relates to a method of preparing a synthetic gene, comprising the step of inserting the polynucleotide target cassette into a regulatory region of the synthetic gene.

A further aspect of the invention relates to a method of making a synthetic gene comprising the steps of inserting one or more nucleic acid segments comprising a seed match and 5' and 3' flanking sequences into a regulatory region of the polynucleotide of the synthetic gene.

Another aspect of the invention relates to a method of identifying one or more seed matches and flanking sequences to be inserted into a synthetic gene, comprising the steps of identifying a seed match and flanking sequences, and inserting said seed match and flanking sequences into a regulatory region of a synthetic gene.

An additional aspect of the invention relates to a method of delivering a synthetic gene to a subject, comprising administering to the subject the synthetic gene, vectors, or pharmaceutical composition of the present invention.

A further aspect of the invention relates to a method of treating a disease associated with abnormal expression of an endogenous gene, comprising administering the synthetic genes, vectors, or pharmaceutical compositions of the present invention, thereby treating the disease.

Another aspect of the invention relates to a method of treating a disease associated with abnormal expression of an endogenous gene or expression of a mutant protein encoded by an endogenous gene in a subject, comprising genetically knocking down the endogenous gene in a cell of the subject, and administering the synthetic genes, vectors, or pharmaceutical compositions of the present invention, thereby treating the disease.

These and other aspects of the invention are set forth in more detail in the description of the invention below.

BRIEF DESCRIPTION OF THE DRAWINGS

FIG. 2A shows miRNA expression level results increased or decreased in MeCP2-null versus WT tissue with a p-value less than 0.10; FIG. 2B shows miRNA expression level results increased or decreased in MeCP2-null versus WT tissue with a p-value less than 0.05; FIG. 2C shows miRNA expression level results increased or decreased in MeCP2-null versus WT tissue with a p-value less than 0.01.

FIGS. 10A-10E show how the RTT-specific panel reg1 tightly regulates total MeCP2 expression in WT Purkinje cells. Purkinje cells are located close to the intracisternal injection site and are vulnerable to supraphysiological transgene expression. The corrected total cell fluorescence (anti-MeCP2 signal) for each nucleus was normalized to that of the mean MeCP2 signal for myc(−) Purkinje nuclei. The means presented for each mouse in FIG. 10A represent the normalized MeCP2 signal averaged across all myc(+) nuclei quantified for the specified host. Iterative averaging across cells within a Z-stack, then across Z-stacks within a single mouse, likewise yields a significant decrease in total MeCP2 expression. FIGS. 10A and 10B show that after treatment with the published control (AAV9/MeP426-miniMECP2-myc-RDH1pA; Gadalla et al., 2017), the mean total MeCP2 expression (mini+endogenous full-length) in transduced Purkinje cells was 5× that of non-transduced Purkinje cells. The positive control panel for neuronal knockdown (featuring 3 targets for miR-124-3p) decreased overexpression by half (p=0.06). The reg1 cassette also decreased overexpression by half (p=0.02). FIG. 10C shows histograms of total MeCP2 intensity, showing that reg1 narrows the distribution of total MeCP2 intensity, indicative of tighter regulation. FIG. 10D shows the mean total MeCP2 intensity of transduced Purkinje cells versus local transduction efficiency, where each data point represents the mean intensity and transduction efficiency for Purkinje cells within a single Z-stack. Trendlines connect Z-stacks from a single mouse. The reg1 cassette limits total MeCP2 expression, even in areas of the cerebellum with high transduction efficiency. In contrast, the negative control panel permits total MeCP2 expression that grossly exceeds physiological levels in areas with high local transduction efficiency. FIG. 10E shows that the reg1 cassette permits transgene expression in NeuN+ cells. In contrast, the positive control for neuronal knockdown decreases the percentage of NeuN+ cells. Data are means±SEM.

FIG. 15B shows representative images for the thalamus, hippocampus, and medulla. Gain settings were manipulated for reg2 images so that the anti-myc signal would be easily visible. FIG. 15C shows that Reg2 enhances apparent neuronal tropism in thalamus. Data are means±SEM. Scale bar indicates 20 µm. *$p \leq 0.05$.

DETAILED DESCRIPTION OF THE INVENTION

Figure 1:
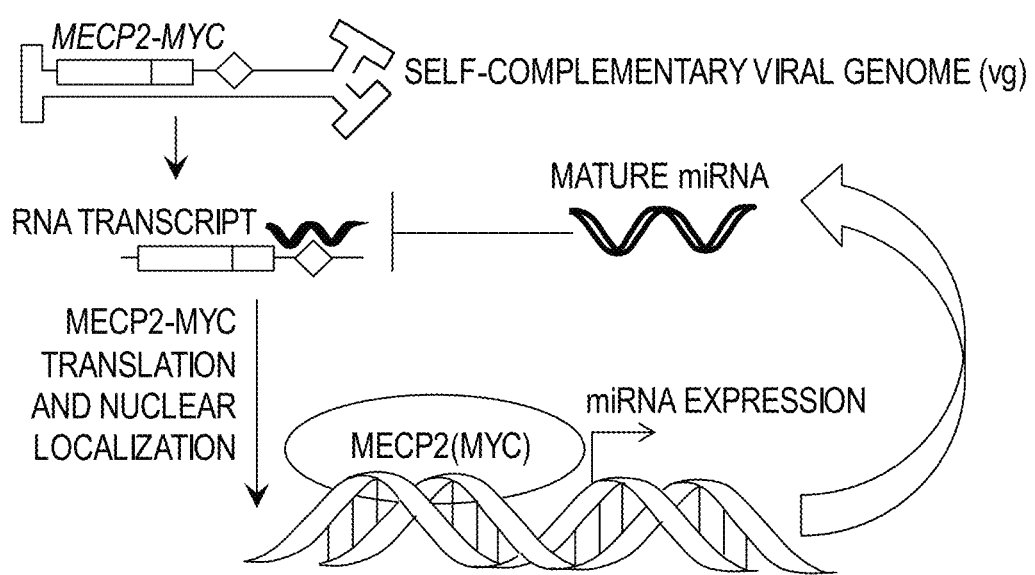
FIG. 1 shows a feedback loop depicting how MeCP2-driven miRNAs may attenuate toxic overexpression exogenous MeCP2.
Figure 2A:
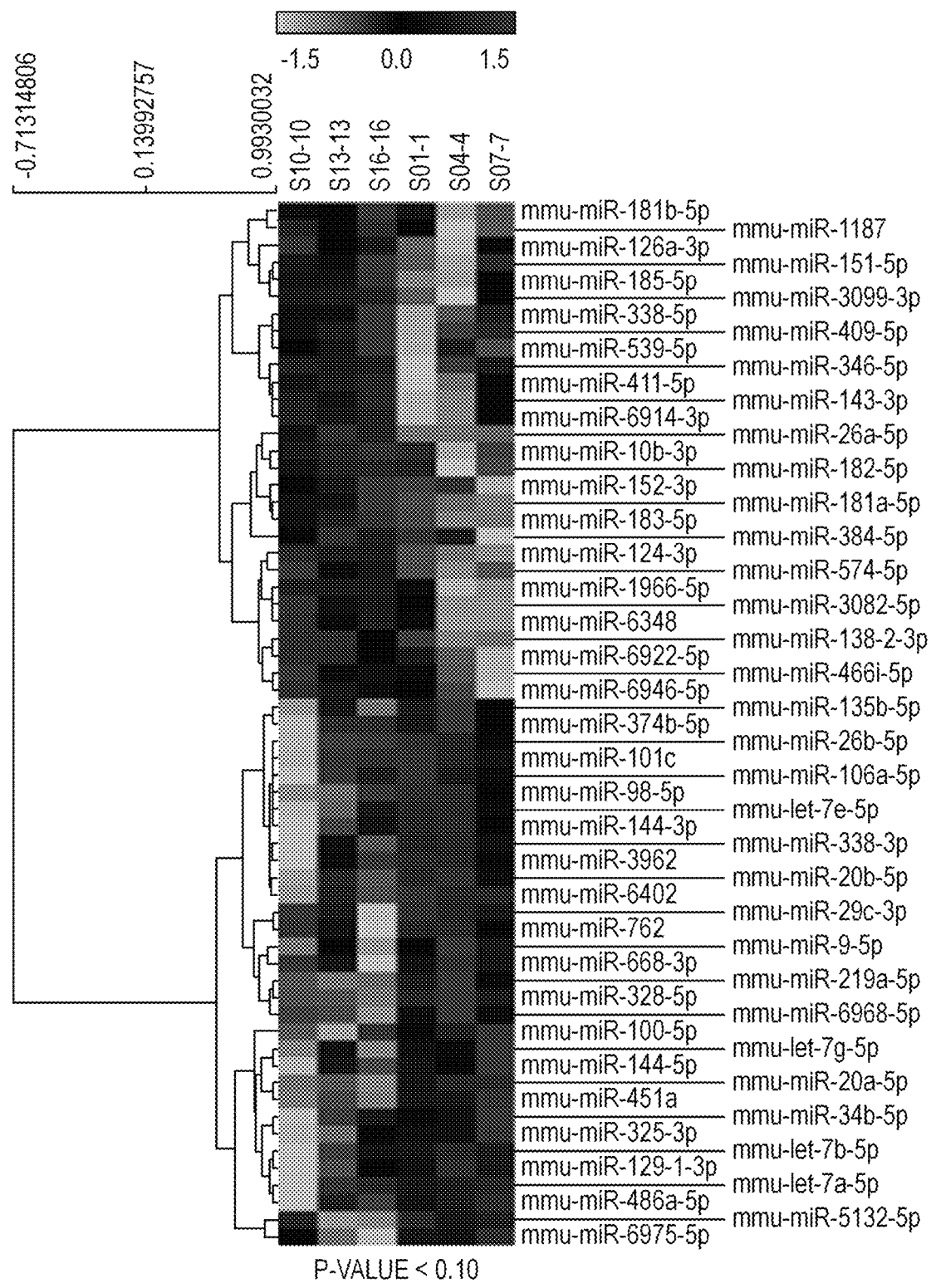
FIGS. 2A-2C show sample microarray data. The selected data quantifies miRNA expression levels in MeCP2-null versus wild-type (WT) tissue.
Figure 2B:
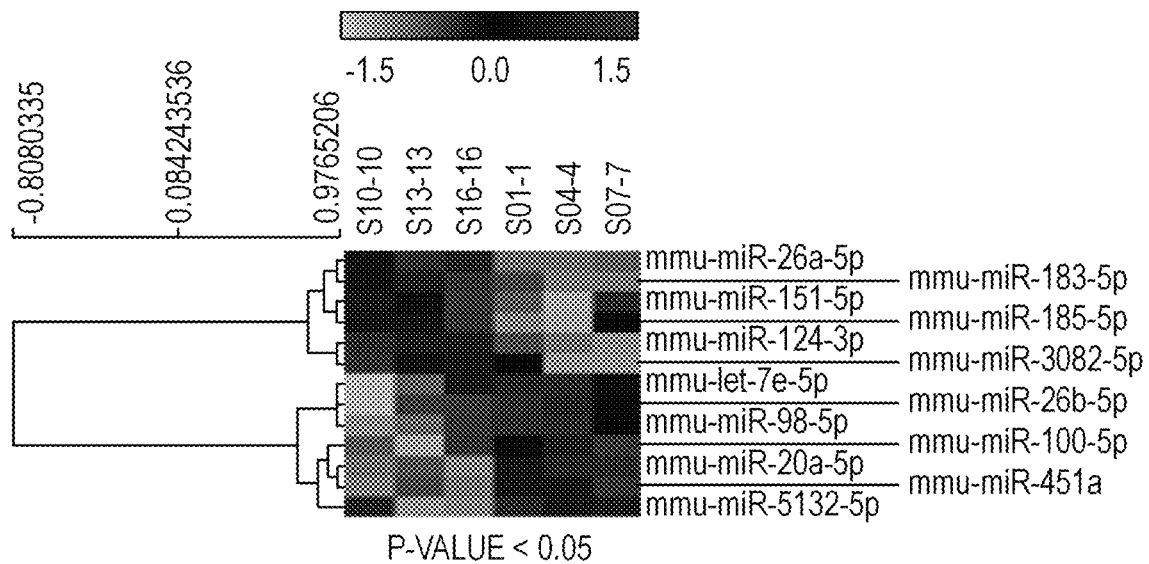
Figure 2C:
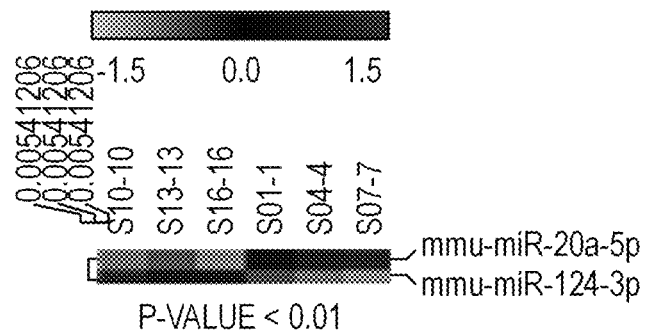
Figure 3:
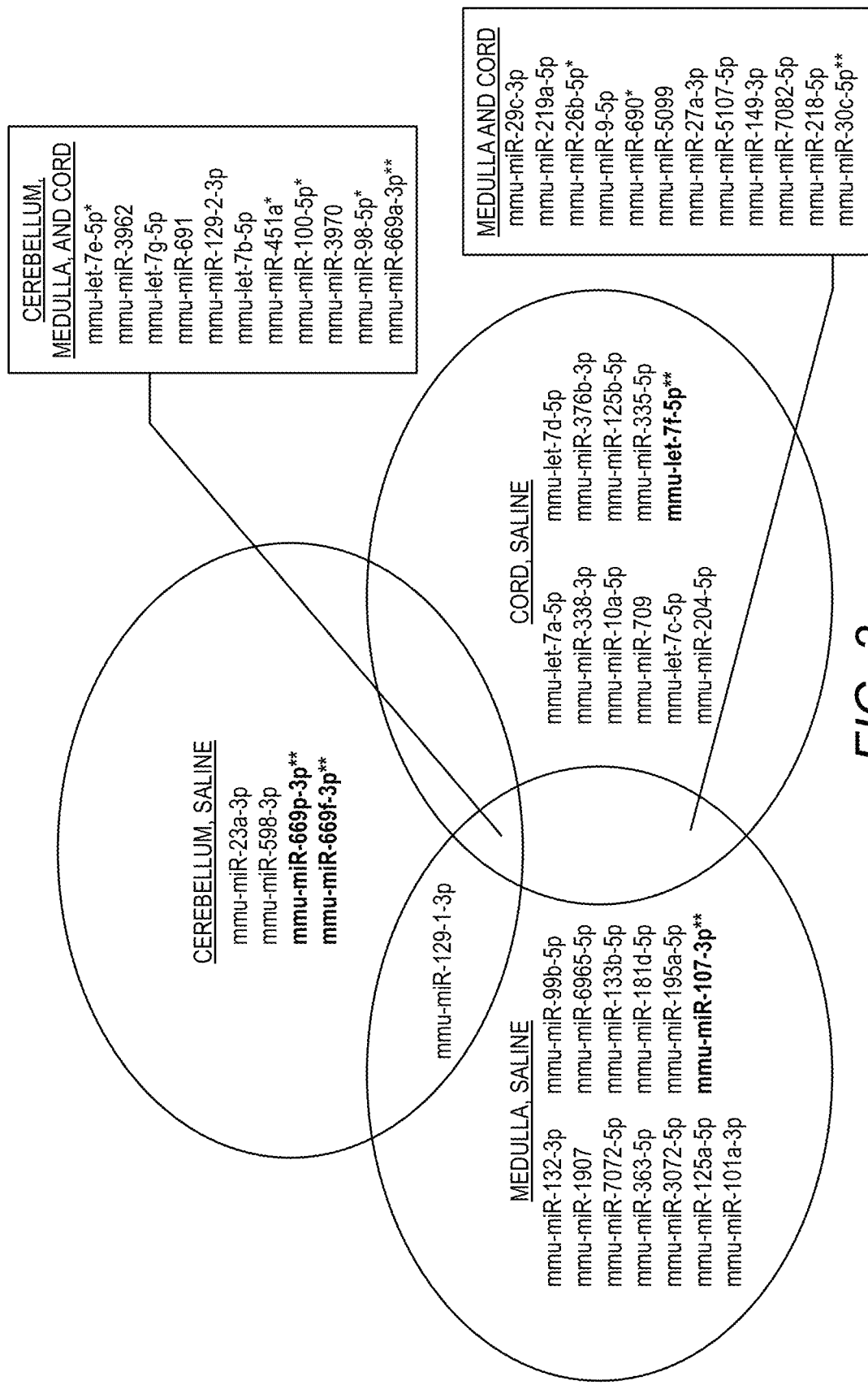
FIG. 3 shows miRNAs with increased mean expression levels in saline-treated WT mice (compared to saline-treated KO mice). miRNAs with statistically significant increases in expression (in at least 1 of the 3 tissue types) are indicated (*). False positive hits that are also upregulated in response to AAV9/EGFP (in any tissue) are indicated (**). n=2 screening replicates per biological sample; n=3 mice per treatment group.
Figure 4:
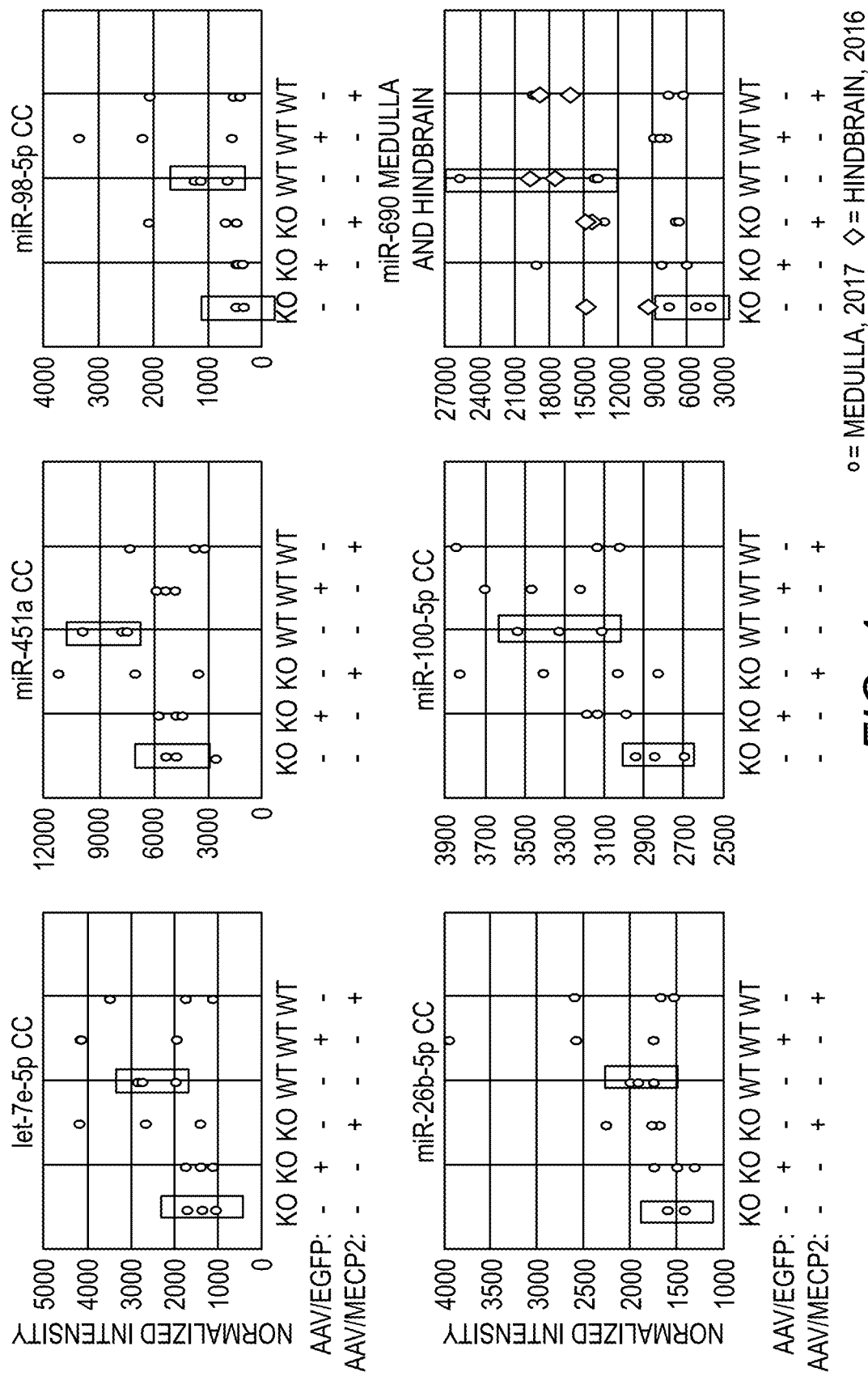
FIG. 4 shows miRNAs with increased expression in either cervical cord (CC) or medulla in correlation with endogenous MeCP2 expression. Each data point is the average of 2 screening replicates for a single mouse. Groups that are significantly different from each other are boxed in red. n=3 mice per treatment group.
Figure 5:
FIG. 5 shows miRNAs with increased mean expression levels in AAV/MECP2-treated KO mice (compared to saline-treated KO mice). miRNAs with statistically significant increases in expression (in at least 1 of the 3 tissue types) are indicated (*). False positive hits that are also upregulated in response to AAV9/EGFP (in any tissue) are indicated (**). n=2 screening replicates per biological sample; n=3 mice per treatment group.
Figure 6:
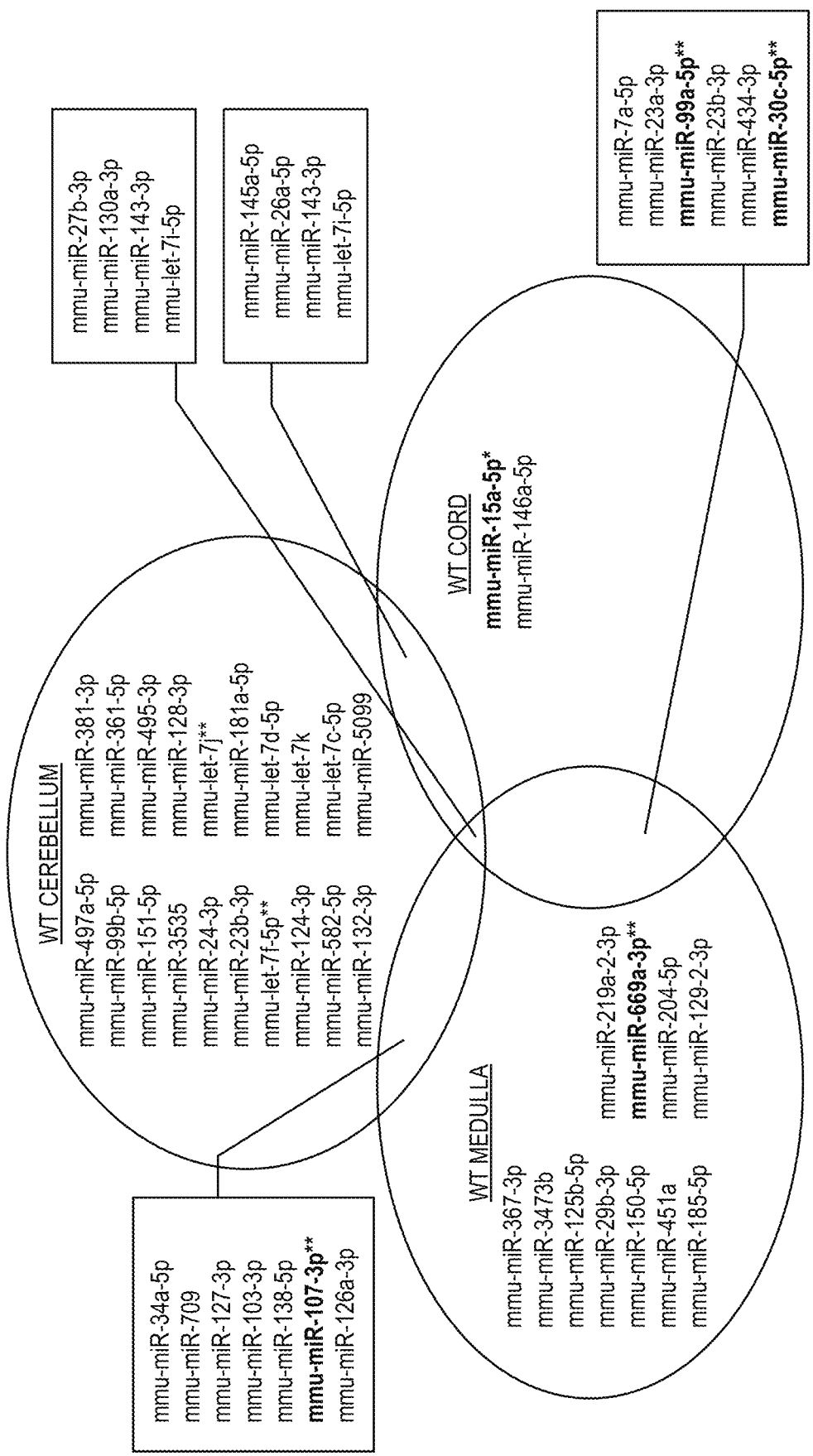
FIG. 6 shows miRNAs with increased mean expression levels in AAV/MECP2-treated WT mice (compared to saline-treated WT mice). miRNAs with statistically significant increases in expression (in at least 1 of the 3 tissue types) are indicated (*). False positive hits that are also upregulated in response to AAV9/EGFP (in any tissue) are indicated (**). n=2 screening replicates per biological sample; n=3 mice per treatment group.
Figure 7:
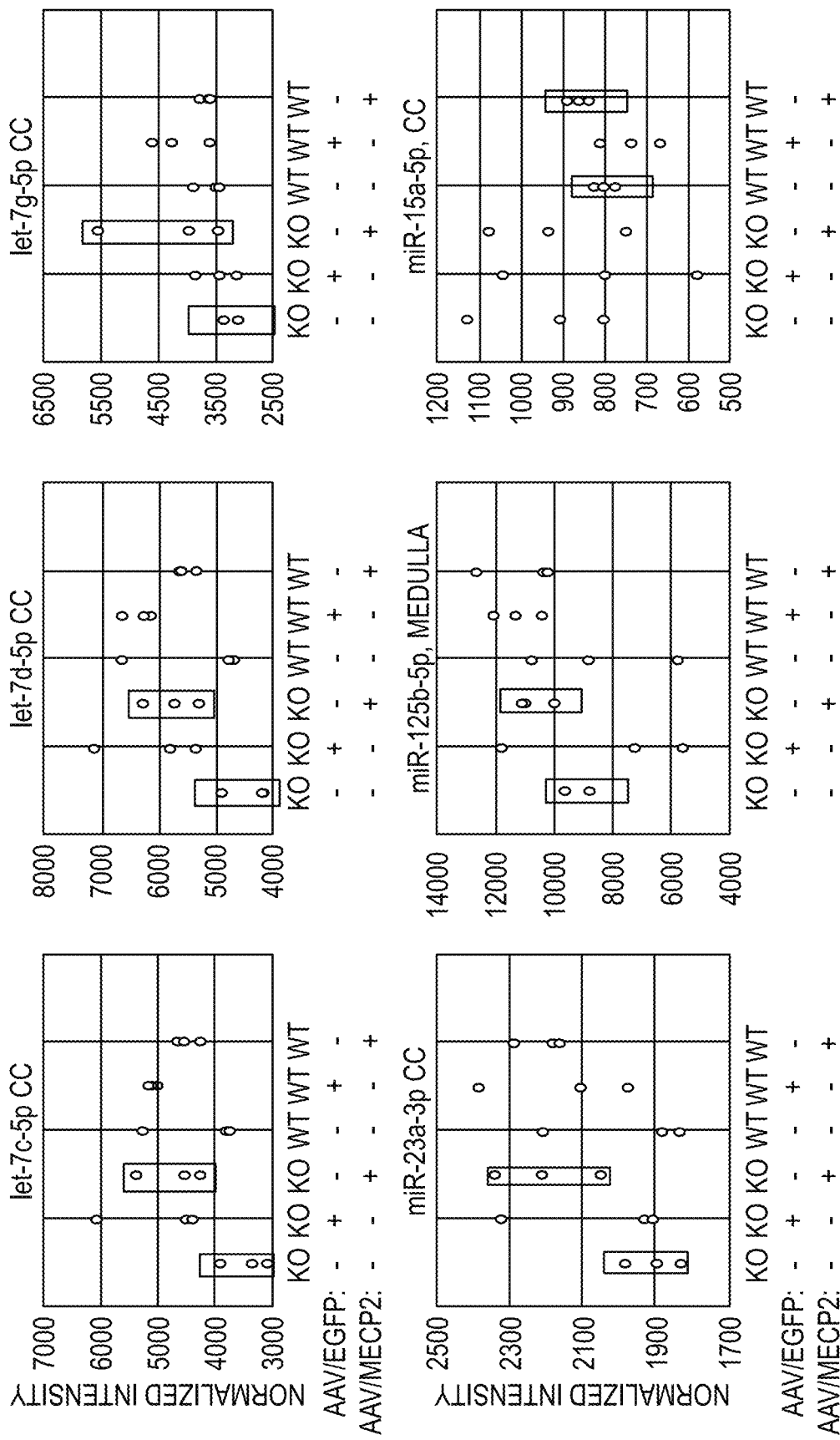
FIG. 7 shows miRNAs with increased expression in correlation with exogenous MeCP2 expression in either WT or KO mice.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic genes, polypeptides, antibodies or antigen-binding fragments thereof, manipulation of nucleic acid sequences, production of transformed cells, the construction of vector constructs, and the generation and analysis of datasets. Such techniques are known to those skilled in the art. See. e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

"Optional" or "optionally" means that the subsequently described event or circumstance can or cannot occur, and that the description includes instances where the event or circumstance occurs and instances where it does not.

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or fewer (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or fewer additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "sequence identity," as used herein, has its standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/RE-ADME.html. WU-BLAST-2 uses several search parameters, which are preferably set to their default values. The parameters are dynamic values and are established by the program itself depending upon the composition of the particular sequence of interest and the composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-BLAST-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences that contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations, relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

The term "endogenous" refers to a component naturally found in an environment, i.e., a gene, nucleic acid, miRNA, protein, cell, or other natural component expressed in the subject, as distinguished from an introduced component, i.e., an "exogenous" component.

As used herein, the term "heterologous" refers to a nucleotide/polypeptide that originates from a foreign species, or, if from the same species, is substantially modified from its native form in composition and/or genomic locus by deliberate human intervention.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or modified nucleotide bases. The term "nucleotide sequence" or "nucleic acid sequence" refers to both the sense and antisense strands of a nucleic acid, either as individual single strands or in the duplex. The term "ribonucleic acid" (RNA) is inclusive of RNAi (inhibitory RNA), dsRNA (double stranded RNA), siRNA (small interfering RNA), shRNA (short/small hairpin RNA), mRNA (messenger RNA), miRNA (micro-RNA), tRNA (transfer RNA, whether charged or discharged with a corresponding acylated amino acid), long non-coding RNA (lncRNA), ribosomal RNA (rRNA), small nuclear RNA (snRNA), small nucleolar RNA (snoRNA) and cRNA (complementary RNA), and the term "deoxyribonucleic acid" (DNA) is inclusive of cDNA and genomic DNA and DNA-RNA hybrids.

MicroRNAs are a class of noncoding small RNAs that originate from primary miRNA (pri-miRNA) transcripts that are encoded by miRNA genes. The pri-miRNA transcripts are processed into smaller 19-24 nucleotide RNAs, which can regulate gene expression, for example, through silencing reactions mediated by translational inhibition or cleavage.

The terms "nucleic acid segment," "nucleotide sequence," or more generally "segment" will be understood by those in the art as functional terms that include genomic sequences, ribosomal RNA sequences, transfer RNA sequences, messenger RNA sequences, small regulatory RNAs, operon sequences and smaller engineered nucleotide sequences that express or may be adapted to express, proteins, polypeptides or peptides. Nucleic acids of the present disclosure may also be synthesized, either completely or in part, by methods known in the art. Thus, all or a portion of the nucleic acids of the present disclosure may be synthesized using codons preferred by a selected host. Such species-preferred codons may be determined, for example, from the codons used most frequently in the proteins expressed in a particular host species. Other modifications of the nucleotide sequences may result in mutants having slightly altered activity.

As used herein with respect to nucleic acids, the term "fragment" refers to a nucleic acid that is reduced in length relative to a reference nucleic acid and that comprises, consists essentially of and/or consists of a nucleotide sequence of contiguous nucleotides identical or almost identical (e.g., 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. In some embodiments, the nucleic acid fragment comprises, consists essentially of or consists of at least about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive nucleotides. In some embodiments, the nucleic acid fragment comprises, consists essentially of or consists of less than about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive nucleotides.

As used herein with respect to polypeptides, the term "fragment" refers to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive amino acids. In some embodiments, the polypeptide fragment comprises, consists essentially of or consists of less than about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive amino acids.

As used herein with respect to nucleic acids, the term "functional fragment" or "active fragment" refers to nucleic acid that encodes a functional fragment of a polypeptide.

As used herein with respect to polypeptides, the term "functional fragment" or "active fragment" refers to polypeptide fragment that retains at least about 20%, 25%, 30%, 35%, 40%, 45%, 50%, 55%, 60%, 65%, 70%, 75%, 80%, 85%, 90%, 95%, 96%, 97%, 98%, 99%, 99.5% or more of at least one biological activity of the fill-length polypeptide (e.g., the ability to up- or down-regulate gene expression). In some embodiments, the functional fragment actually has a higher level of at least one biological activity of the full-length polypeptide.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

The terms "enhance" and "increase" refer to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The terms "inhibit" and "reduce" or grammatical variations thereof as used herein refer to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts may be referred to as "transcription products" and encoded polypeptides may be referred to as "translation products." Transcripts and encoded polypeptides may be collectively referred to as "gene products." If the polynucleotide is derived from genomic DNA, expression may include splicing of the mRNA in a eukaryotic cell. The expression product itself, e.g., the resulting nucleic acid or protein, may also be said to be "expressed." An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

As used herein, the term "synthetic gene" refers to a nucleic acid sequence generated non-naturally by deliberate human design, the synthetic gene comprising, among other components, a coding region for a protein or nucleic acid of interest, and regulatory regions for expression of the coding region. Structural and functional components of the synthetic gene may be incorporated from differing and/or a plurality of source material. The synthetic gene may be delivered exogenously to a subject, wherein it would be exogenous in comparison to a corresponding endogenous gene. When expressed in a cell, the synthetic gene product may be referred to as a synthetic product (e.g., "synthetic RNA" or "synthetic polypeptide"). Under certain conditions, the synthetic gene may also be interchangeably referred to as a "transgene."

As used herein, the terms "transgenic" and/or "transgene" refer to a nucleic acid sequence containing a functional coding region for a gene that comprises one or more exogenous nucleic acids. The exogenous nucleic acid can be stably integrated within the genome such that the polynucleotide is passed on in successive cell divisions. The exogenous nucleic acid can be integrated into the genome alone or as part of a recombinant expression cassette. "Transgenic" may be used to designate any substrate the genotype of which has been altered by the presence of an exogenous nucleic acid.

The term "feedback" refers to molecular encoded information being provided to a substrate as a result of some result, effect, or function performed by that same substrate. The substrate may be any type of micro or macro molecule, including but not limited to genes or transcriptional or translation products of genes such as RNAs and proteins. The term "feedback loop" refers to the loop of a molecule performing a function, effect, and/or result, whereupon the information of that function, effect, and/or result is returned to the receiving source. For example, the function, effect, and/or result of the expression of a gene (e.g., MECP2) can result in feedback via the binding of miRNAs onto the mRNA derived from that gene, when those miRNAs were expressed due to the function, effect, and/or result of the expression of that gene. A feedback loop can be inhibitory/ negative (i.e., suppressing the continuation of further function, effect, and/or result), or positive (enhancing continuation). A substrate capable of receiving feedback is said to be "feedback-enabled." Feedback that is variable in strength of inhibition and/or enhancement dependent on the expression level and/or function of a nucleic acid or transcription or translation product of a gene can be said to be "dose dependent" feedback, and/or a "dose dependent feedback loop."

The terms "polypeptide," "peptide" and "protein" may be used interchangeably to refer to polymers of amino acids of any length. The terms "nucleic acid," "nucleic acid sequence," and "polynucleotide" may be used interchangeably to refer to polymers of nucleotides of any length. As used herein, the terms "nucleotide sequence," "polynucleotide," "nucleic acid sequence," "nucleic acid molecule" and "nucleic acid fragment" refer to a polymer of RNA, DNA, or RNA and DNA that is single- or double-stranded, optionally containing synthetic, non-natural and/or altered nucleotide bases.

As used herein, the terms "gene of interest," "nucleic acid of interest" and/or "protein of interest" refer to that gene/ nucleic acid/protein desired under specific contextual conditions.

The term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. The region in a nucleic acid sequence or polynucleotide in which one or more regulatory elements are found is referred to as a "regulatory region."

The term coding region as used herein, refers to the portion of a polynucleotide, e.g., a gene, that encodes a polypeptide.

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

As used herein, the term "binding site" refers to any general structural feature that acts as a location for binding between components. As applied to nucleic acids or polynucleotides, the term "binding site" can refer to, though is not limited to, a nucleotide sequence in a specific motif of primary, secondary, or tertiary structure wherein that motif provides a binding location for an interacting molecule, which may comprise other nucleic acids or proteins. As applied to peptides, polypeptides, or proteins, the term "binding site" can refer to, though is not limited to, a sequence of amino acids in a specific motif of primary, secondary, tertiary or quaternary structure wherein that motif provides a binding location for an interacting molecule, which may comprise other nucleic acids or proteins.

As used herein, the term "seed match" specifically refers to a subset of nucleotides within a longer endogenous mRNA sequence empirically identified, validated, or putatively predicted to be the relevant target nucleotide sequence for recognition by, and complementary binding of, a miRNA species to the corresponding mRNA containing said seed match. The terms "seed" or "seed region" refer to a subset of nucleotides within the longer endogenous miRNA sequence empirically identified, validated, or putatively predicted to be the relevant nucleotide sequence for recognition of, and complementary binding to, a target seed match of an mRNA species by that miRNA species. In general, the seed match of an mRNA is encoded within its respective 3 prime (3') untranslated region (3' UTR), but may be present in other locations. A "validated" or "empirically identified" seed match is defined as a seed match currently known in the art and those identified in the future. A "putative" or "predicted" seed match is defined as a seed match not yet empirically known or defined.

The terms "5 prime (5') flanking sequence" and/or "3' flanking sequence" refer to a subset of nucleotides in sequence found immediately adjacent to (i.e. "neighboring") a specified sequence (e.g., the seed match) on either end of the sequence of interest (i.e., the 5' flanking end, and/or the 3' flanking end) within the source sequence. In some cases, 5' flanking sequences may provide additional Watson-Crick (WC) complementary binding to the matching miRNA. Together, the 5' and 3' flanking sequences contribute to an inter-seed match spacing that may promote cooperative repression by two or more miRNAs binding to neighboring seed matches (Grimson et al., 2007). 5' and 3' flanking sequences may also provide a high % adenylate-uridylate (AU) nucleotide context that has been correlated with effective seed matches (Grimson et al., 2007).

The term "3' UTR" refers to the section of mRNA that immediately follows the translation termination codon. In general, an mRNA molecule is transcribed from a DNA sequence and later translated into a peptide, polypeptide, or protein. Several regions of sequence of the mRNA molecule are not translated into protein, including the 5' cap, 5' untranslated region (5' UTR), 3' UTR, and polyadenylation (polyA) tail. In general, the 3' UTR contains regulatory regions that may influence gene expression post-transcriptionally.

As used herein, the terms "gene-dose sensitive" or "dose sensitive" disorders refer to diseases or disorders where the initiation, presentation, progression, symptoms, phenotypes and other related phenomena are variable due to and in congruence with the relative functional expression levels of nucleic acids (e.g., a gene) or transcription or translation products of that gene (e.g., an RNA species or protein) involved in the initiation, presentation, progression, symptoms, phenotypes or other related phenomena of the disease or disorder. For example, a disorder may be described as dose sensitive if its phenotype changes with different expression levels of a specific gene. For another example, a disorder may also be referred to as dose-sensitive when a gene is mutated to produce a hypo- or hyper-functioning protein that influences the initiation, presentation, progression, symptoms, phenotypes or other related phenomena of the disorder.

As used herein, the term "intellectual ability disorders" refers to a group of diseases, disorders, or disabilities that affect the neurodevelopmental intellectual functioning, mental abilities, cognitive abilities, and/or adaptive functioning of a subject, i.e., the "intellectual ability" of a subject, including the abilities to reason, plan, think, and communicate. The term "intellectual ability disorder" may be used interchangeably with "intellectual disability." Other symptomology that may present along with intellectual ability disorders includes, but is not limited to, speech abnormalities, seizures, microcephaly, hypotonia, bruxism, and/or stereotypy. Intellectual ability disorders that vary in their initiation, presentation, progression, symptoms, phenotypes or other related phenomena may be referred to as "dose sensitive intellectual ability disorders," and their causative genes may be referred to as "dose-sensitive genes that mediate intellectual ability."

As used herein, the terms "target tissue" and "off-target tissue" refer to bodily regions, organs, tissues, structures and/or cells of the subject wherein a specified nucleic acid or protein of interest is expressed. "Target tissues" are those regions, organs, tissues, structures and/or cells of the subject wherein the endogenous nucleic acid or protein of interest is expressed under typical healthy and/or diseased conditions. "Off-target tissues" are those regions, organs, tissues, structures and/or cells of the subject wherein the endogenous nucleic acid or protein of interest is not expressed under typical healthy and/or diseased conditions.

A "vector" refers to a compound used as a vehicle to carry foreign genetic material into another cell, where it can be replicated and/or expressed. A cloning vector containing foreign nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs or expression cassettes) are for the expression of the exogenous gene in the target cell, and generally have a promoter sequence that drives expression of the exogenous gene. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a nanoparticle.

By "pharmaceutically acceptable" it is meant a material that is not toxic or otherwise undesirable, i.e., the material may be administered to a subject without causing any undesirable biological effects.

As used herein, the term "polynucleotide target cassette" refers to a nucleotide sequence and/or nucleotide cassette comprising one or more predetermined seed matches and 5' and 3' flanking sequences neighboring each seed match. The polynucleotide target cassette may be designed by appropriate selection of seed matches to protect against overexpression phenotypes shared by multiple disorders with distinct genetic etiologies, but common target tissues, when the cassette is inserted to a target gene. The polynucleotide target cassette can comprise any number of seed matches and 5' and 3' flanking sequences.

By the terms "treat," "treating," and "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder.

As used herein, the terms "prevent," "prevents," and "prevention" (and grammatical equivalents thereof) refer to a delay in the onset of a disease or disorder or the lessening of symptoms upon onset of the disease or disorder. The terms are not meant to imply complete abolition of disease and encompass any type of prophylactic treatment that reduces the incidence of the condition or delays the onset and/or progression of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "administering" and "administration" of a synthetic gene, expression cassette, vector, plasmid, viral vector, transformed cell, nanoparticle, or pharmaceutical composition to a subject include any route of introducing or delivering to a subject a compound to perform its intended function. Administration can be carried out by any suitable route, including orally, intranasally, parenterally (intravenously, intramuscularly, intraperitoneally, intracisternally, intrathecally, intraventricularly, or subcutaneously), or topically. Administration includes self-administration and administration by another.

Synthetic Genes

This invention relates to feedback-enabled synthetic genes, polynucleotide target cassettes, vectors, and pharmaceutical compositions for the purpose of providing transgene expression in target tissues that is capable of endogenous regulation, for treating disorders such as dose-sensitive intellectual ability disorders.

Thus, one aspect of the invention relates to a synthetic gene comprising a polynucleotide comprising a coding region encoding a protein or nucleic acid of interest and one or more regulatory regions, wherein the polynucleotide further comprises one or more nucleic acid segments each comprising a seed match identified as a binding site for an endogenous miRNA and a 5' flanking sequence and a 3' flanking sequence neighboring said seed match, wherein said one or more nucleic acid segments are inserted into a regulatory region of said polynucleotide such that expression of said protein or nucleic acid of interest when said synthetic gene is delivered to a cell expressing the endogenous miRNA is reduced relative to expression of a protein or nucleic acid of interest when a synthetic gene that does not comprise the one or more nucleic acid segments is delivered to a cell expressing the endogenous miRNA.

In some embodiments, the coding region encoding a nucleic acid or protein of interest comprises the coding region of a gene or an active fragment of a gene, e.g., a gene associated with intellectual ability gene-dose sensitive disorders. Genes associated with intellectual ability gene-dose sensitive disorders include but are not limited to TCF4, UBE3A, DYRK1A, MEF2C, NSD1, ZEB2, MBD5, RPS6KA3, ATRX, MECP2, FOXG1, AKT3, SLC6A1, or an active fragment thereof. In some embodiments, the coding region encoding a protein or nucleic acid of interest comprises the coding region of the gene MECP2 or an active fragment thereof.

The seed match may be of any nucleotide sequence length, generally of about 3 to about 10 nucleotides. e.g., 3, 4, 5, 6, 7, 8, 9, 10 or any range therein. In some embodiments, the seed match of the present invention is about 5 to about 10 nucleotides in length. In some embodiments, the seed match of the present invention is about 6 to about 8 nucleotides in length.

The synthetic gene of the present invention may contain one or more seed matches and 5' and 3' flanking sequences. In some embodiments, the synthetic gene comprises at least two seed matches, e.g., at least 2, 3, 4, 5, 6, 7, 8, 9, 10 or more or any range therein. In some embodiments, the synthetic gene comprises three or more seed matches. In some embodiments, the synthetic gene comprises three or more seed matches. In some embodiments, the synthetic gene comprises 3 to 8 seed matches. In some embodiments, some or all seed matches are in the 3' UTR.

The 5' and/or 3' flanking nucleotide sequence may be of any length, generally of about 1 to about 30 nucleotides on each 5' and/or 3' end of the specified sequence (e.g., the seed match). In some embodiments, the flanking nucleotide sequences of the present invention are about 9 to about 13 nucleotides on each 5' and/or 3' end of the specified sequence (e.g., the seed match). In some embodiments, the flanking nucleotide sequences are about 11 nucleotides on each 5' and/or 3' end of the specified sequence (e.g., the seed match). Thus, in some embodiments of the present invention, the total number of nucleotides of the 5' and 3' flanking sequences of the specified sequence (e.g., the seed match), is about 7 to about 40 nucleotides, e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides or any range therein. In some embodiments, the total number of nucleotides of the 5' and 3' flanking sequences of the specified sequence (e.g., the seed match), is about 20 to about 25 nucleotides. In some embodiments, the total number of nucleotides of the 5' and 3' flanking sequences of the specified sequence (e.g., the seed match), is about 22 nucleotides. In some embodiments, each seed match is separated from the next most proximate seed match by the 3' and 5' flanking sequences between them. Thus, in some embodiments of the present invention, the at least two seed matches are separated by about 7 to about 40 nucleotides. In some embodiments, the at least two seed matches are separated by about 20 to about 25 nucleotides. In some embodiments, the at least two seed matches are separated by about 22 nucleotides.

The seed matches and 5' and 3' flanking sequences of the present invention may bind to one or more miRNAs. In some embodiments, the seed matches and 5' and 3' flanking sequences bind to one or more miRNAs including miR-690, miR-124-3p, miR-451a, miR-9-5p, miR-26-5p, miR-23-3p, miR-218-5p, miR-27-3p, let-7-5p/98-5p, miR-29-3p, miR-338-3p, miR-98-5p, miR-7-5p, miR-494-3p, or any combination thereof. In addition, while not wishing to be bound by theory, it is conceptually possible that miRNAs yet to be identified could contribute to the MeCP2 feedback loop. Any miRNA containing a seed sequence permitting Watson-Crick (WC) base-pairing between a particular miRNA seed and the miRNA seed matches in a target panel may help mediate endogenous regulation of the exogenous target nucleic acid or protein of interest, i.e., the product of the coding region encoding a nucleic acid or protein of interest. Thus, in some embodiments, the seed matches and 5' and 3' flanking sequences bind to one or more miRNAs comprising a seed sequence permitting WC base-pairing between the miRNA seed sequence and the seed matches of the present invention. In some embodiments, the seed matches and 5' and 3' flanking sequences bind to the miRNAs miR-9-5p, miR-26-5p, miR-23-3p, miR-218-5p, miR-27-3p, and let-7-5p. In some embodiments, the seed matches and 5' and 3' flanking sequences bind to the miRNAs miR-690, miR-451a, and let-7-5p. In some embodiments, the seed matches and 5' and 3' flanking sequences do not bind to the miRNAs miR-22, miR-19, miR-132, and/or miR-124. In some embodiments, the seed matches and flanking 5' and 3' sequences neighboring the seed matches comprise, consist essentially of, or consist of the nucleotide sequence of SEQ ID NO:1 or a nucleotide at least 70% identical thereto, e.g., at least about 70, 75, 80, 85, 90, 91, 92, 93, 94, 95, 96, 97, 98, or 99% identical thereto, which contains seed matches for miR-9-5p, miR-26-5p miR-23-3p, miR-218-5p, miR-27-3p, and let-7-5p. Seed matches are underlined.

"Reg2" target seed matches and 5' and 3' flanking sequences

SEQ ID NO: 1.
5'CTGTTCTAGCCCCCAAAGAGTTTTCTGTGCTTGCTTTTGAAACTTGA

AGTCTTGAAAACCAAAGACATAGATGTGAAAATTTTAGGCAGTGTAAGCT

GATAGCACAAGTTCTGGCGACTCACAATTATGCTGTGAATTTTACAAAAA

GAAGCAGTAATCTACCTCAGCCGATAAC-3'

In some embodiments, the seed matches and flanking 5' and 3' sequences neighboring the seed matches comprise, consist essentially of, or consist of the nucleotide sequence of SEQ ID NO:2 or a nucleotide at least 70% identical thereto, e.g., at least about 70, 75, 80, 85, 90, 91, 92, 93, 94, 95, 96, 97, 98, or 99% identical thereto, which contains seed matches for miR-451a, let-7-5p, and miR-690. Seed matches are underlined.

"Reg1" target seed matches and 5' and 3' flanking sequences

SEQ ID NO: 2.
5'ATAAGGGCAGAAACGGTTCACATTCCATTCTGCCCCGGACCTACCTCC

CTCCCTCTCCTTATCAAACCCTAGCCTTGCTTGTTAAAT-3'

In some embodiments, the present invention comprises a vector comprising a synthetic gene. A vector can be any suitable means for delivering a polynucleotide to a cell. In some embodiments, the vector is a plasmid, a viral vector, an expression cassette, a transformed cell, or a nanoparticle.

In particular embodiments, the present invention provides a pharmaceutical composition comprising a synthetic gene or vector of the invention in a pharmaceutically acceptable carrier. In some embodiments, the present invention provides a pharmaceutical composition comprising a synthetic gene or vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

In particular embodiments, the present invention provides a polynucleotide target cassette for providing dose dependent inhibitory feedback to a synthetic gene, the cassette comprising one or more nucleic acid segments each comprising a seed match identified as a binding site for an endogenous miRNA and 5' and 3' flanking sequences neighboring said seed match. Polynucleotide target cassettes can be used to generate a synthetic gene via insertion of the cassette into a regulatory region of a polynucleotide of the synthetic gene, thereby providing the capability of dose dependent inhibitory feedback to the synthetic gene wherein miRNAs capable of binding to the provided seed matches within the polynucleotide target cassette can regulate expression of the synthetic gene.

The polynucleotide target cassette can comprise any number of seed matches and 5' and 3' flanking sequences. In some embodiments, the polynucleotide comprises at least two seed matches and 5' and 3' flanking sequences, e.g., 2, 3, 4, 5, 6, 7, 8, 9, 10 or more or any range therein. In some embodiments, the polynucleotide target cassette comprises three or more seed matches and 5' and 3' flanking sequences. In some embodiments, the polynucleotide target cassette comprises 3 to 8 seed matches and 5' and 3' flanking sequences. In some embodiments, the polynucleotide target cassette comprises seed matches and 5' and 3' flanking sequences that bind to one or more miRNAs which may help mediate exogenous regulation of the target nucleic acid or protein of interest, i.e., the product of the coding region encoding a nucleic acid or protein of interest, wherein said one or more miRNAs comprise a seed sequence permitting WC base-pairing between the miRNA seed sequence and the seed matches. In some embodiments, the polynucleotide target cassette comprises seed matches and 5' and 3' flanking sequences that bind to one or more miRNAs selected from miR-690, miR-9-5p, miR-26-5p miR-23-3p, miR-218-5p, miR-27-3p, let-7-5p, or any combination thereof. In some embodiments, the polynucleotide target cassette comprises seed matches and 5' and 3' flanking sequences that bind to the miRNAs miR-9-5p, miR-26-5p miR-23-3p, miR-218-5p, miR-27-3p, and let-7-5p. In some embodiments, the polynucleotide target cassette comprises seed matches and 5' and 3' flanking sequences that bind to the miRNAs miR-690, miR-451a, and let-7-5p. In some embodiments, the polynucleotide target cassette comprises seed matches wherein the seed match is about 5 to about 10 nucleotides in length. In some embodiments, the polynucleotide target cassette comprises seed matches wherein the seed match is about 6 to about 8 nucleotides in length. In some embodiments, the polynucleotide target cassette comprises 5' and 3' flanking sequences neighboring the seed matches that are each about 9 to about 13 nucleotides in length. In some embodiments, the polynucleotide target cassette comprises 5' and 3' flanking sequences neighboring the seed matches that are each about 11 nucleotides in length. In some embodiments, the polynucleotide target cassette comprises seed matches and 5' and 3' flanking sequences neighboring the seed matches that comprise, consist essentially of, or consist of the nucleotide sequence SEQ ID NO:1 or a nucleotide at least 70% identical thereto, e.g., at least about 70, 75, 80, 85, 90, 91, 92, 93, 94, 95, 96, 97, 98, or 99% identical thereto. In some embodiments, the polynucleotide target cassette comprises seed matches and 5' and 3' flanking sequences neighboring the seed matches that comprise, consist essentially of, or consist of the nucleotide sequence SEQ ID NO:2 or a nucleotide at least 70% identical thereto, e.g., at least about 70, 75, 80, 85, 90, 91, 92, 93, 94, 95, 96, 97, 98, or 99% identical thereto.

Methods of Making a Synthetic Gene

The present invention further provides methods of making synthetic genes, wherein the synthetic genes exhibit dose dependent inhibitory feedback. In one embodiment, the present invention provides a method of preparing a synthetic gene comprising a polynucleotide comprising a coding region encoding a protein or nucleic acid of interest and one or more regulatory regions, comprising the step of inserting a polynucleotide target cassette of the invention into a regulatory region of the synthetic gene.

In some embodiments, the present invention provides a method of inserting a nucleic acid segment into a regulatory region of the synthetic gene. In some embodiments, the present invention provides a method of inserting a seed match known or newly identified to bind to a miRNA of interest into a regulatory region of a polynucleotide of a synthetic gene. In some embodiments, the present invention provides a method of preparing a synthetic gene by inserting a polynucleotide target cassette into a regulatory region of a polynucleotide of the synthetic gene, thereby providing the capability of dose dependent inhibitory feedback to the synthetic gene wherein miRNAs capable of binding to the provided seed matches within the polynucleotide target cassette can regulate expression of the synthetic gene. In some embodiments, the present invention provides a method of making a synthetic gene comprising the step of inserting one or more nucleic acid segments comprising a seed match and 5' and 3' flanking sequences into a regulatory region of a polynucleotide of the synthetic gene. In some embodiments, the methods may include removing one or more endogenous seed matches found within a regulatory region of a polynucleotide of a synthetic gene.

In some embodiments, seed matches and 5' and 3' flanking sequences inserted in a synthetic gene can bind to miRNAs expressed in target tissues and/or off-target tissues, thereby providing feedback enablement to the synthetic gene that inhibits expression of the synthetic gene in off-target tissues and provides endogenous regulation of the synthetic gene in target tissues. In some embodiments, the synthetic gene of the present invention excludes seed matches and 5' and 3' flanking sequences from miRNAs expressed in off-target tissues. In some embodiments, the synthetic gene of the present invention excludes seed matches and 5' and 3' flanking sequences for the miRNAs miR-22, miR-19, miR-132, and/or miR124.

In another embodiment, the present invention provides a method of making a synthetic gene, comprising the steps of: screening for miRNAs with increased expression when a protein or nucleic acid of interest is expressed in a cell relative to when the protein or nucleic acid of interest is not expressed; identifying a seed match and flanking regions for one or more miRNAs having increased expression; preparing a nucleic acid segment comprising said seed match and flanking regions to be inserted into a regulatory region of said polynucleotide, inserting one or more of the nucleic acid segments comprising a seed match identified as a binding site for an endogenous miRNA and 5' and 3' flanking sequences neighboring said seed match into a regulatory region of a polynucleotide comprising a coding region encoding a protein or nucleic acid of interest and one or more regulatory regions.

In some embodiments of a method of making a synthetic gene, the coding region encoding a protein or nucleic acid of interest comprises a coding region of a gene selected from TCF4, UBE3A, DYRK1A, MEF2C, NSD1, ZEB2, MBD5, RPS6KA3, ATRX, MECP2, SLC6A1, FOXG1, AKT3, or an active fragment thereof. Active fragments may include, but are not limited to, active fragments of MeCP2, such as the ΔN, ΔNC, and/or ΔNIC active MeCP2 fragments which account for 88%, 52% and 32% respectively of full-length MeCP2, but retain conserved functionality of methyl-CpG binding and nuclear receptor co-repressor/silencing mediator of retinoic acid and thyroid hormone receptors (NCoR/SMRT) interaction to allow for physical connection of DNA with the NCoR/SMRT complex. These active fragments are truncations of full-length MeCP2 protein, wherein ΔN contains a deletion of residues 13-71 N-terminal to the methyl-CpG binding domain (MBD), residues 72-173) of full-length MeCP2 isoform e2, ΔNC contains an additional deletion of residues 313-484 C-terminal of the NCoR-SMRT interaction domain (NID, residues 272-312), and ΔNIC additionally replaces the intervening amino acids between the MBD and NID domains with a nuclear localization signal from SV40 virus connected by a short flexible linker, as described in Tillotson et al. (Tillotson et al. 2017 *Nature* 550(7676):398-401), which disclosure is fully incorporated herein by reference. Active fragments of MeCP2 used for the treatment of RTT are derived from the e1 isoform of MeCP2. The amino acid numbering described herein is based on the MeCP2 e2 isoform amino acid sequence, by convention.

In some embodiments, the coding region encoding a protein or nucleic acid of interest comprises the coding region of a gene MECP2 or an active fragment thereof. In some embodiments, the one or more nucleic acid segments bind to one or more miRNAs selected from the group consisting of miR-690, miR-124-3p, miR-451a, miR-9-5p, miR-26-5p, miR-23-3p, miR-218-5p, miR-27-3p, let-7-5p/98-5p, and miR-494-3p. In some embodiments, the seed matches and 5' and 3' flanking sequences bind to the miRNAs miR-9-5p, miR-26-5p miR-23-3p, miR-218-5p, miR-27-3p, and let-7-5p. In some embodiments, the seed matches and 5' and 3' flanking sequences bind to the miRNAs miR-690, miR-451a, and let-7-5p.

In another aspect, the present invention provides for a method of identifying one or more seed matches and 5' and 3' flanking sequences to be inserted in a synthetic gene, comprising the steps of: identifying a seed match and 5' and 3' flanking sequences for one or more miRNAs having increased expression when a protein or nucleic acid of interest is expressed in a cell relative to when the protein or nucleic acid of interest is not expressed in the cell; and inserting said seed match and 5' and 3' flanking sequences into a regulatory region of a synthetic gene comprising a polynucleotide comprising a coding region encoding the protein or nucleic acid of interest and one or more regulatory regions. In some embodiments, a method of identifying one or more seed matches and 5' and 3' flanking sequences to be inserted into a synthetic gene additionally comprises the steps of: expressing the protein or nucleic acid of interest in a cell; collecting miRNA from the cell; and calculating expression levels of said miRNAs when said protein or nucleic acid of interest is expressed in the cell relative to when said protein or nucleic acid of interest is not expressed in the cell, thereby creating a nucleic acid dataset of said miRNAs. In some embodiments, the method of identifying can comprise screening a nucleic acid dataset (e.g., a pre-existing dataset) for miRNAs with increased expression when a protein or nucleic acid of interest is expressed in a cell relative to when the protein or nucleic acid of interest is not expressed in the cell, and/or identifying miRNAs with increased expression when a protein or nucleic acid of interest is expressed in a cell relative to when the protein or nucleic acid of interest is not expressed in the cell, and/or screening a nucleic acid dataset for a validated or putative seed match and 5' and 3' flanking sequences.

As used herein, the term "dataset" refers to a collection of related sets of information, i.e., data, attained from experimental or computational analyses, comprising any type of data, including but not limited to nucleic acid sequences or amino acid sequences. The dataset may be screened and/or otherwise searched for particular data of interest depending on variable parameters as defined by each particular dataset. In some embodiments, the dataset is a nucleic acid dataset, i.e., a dataset comprising nucleic acid sequences. In some embodiments, the dataset is a 3' UTR dataset.

In some embodiments, the protein or nucleic acid of interest is a transcription or translation product of a gene selected from TCF4, UBE3A, DYRK1A, MEF2C, NSD1, ZEB2, MBD5, RPS6KA3, ATRX, SLC6A1, FOXG1, AKT3, MECP2, or an active fragment thereof. In some embodiments, the protein or nucleic acid of interest is a transcription or translation product of a gene MECP2 or an active fragment thereof.

Methods of Using a Synthetic Gene

In another aspect of the present invention, a method of delivering a synthetic gene is provided, the method comprising administering to the subject a synthetic gene, a vector, and/or a pharmaceutical composition of the invention, thereby delivering the synthetic gene to the subject.

In an additional aspect of the present invention, a method of treating a disease associated with abnormal expression of an endogenous gene in a target tissue or expression of a mutant protein encoded by an endogenous gene in a target tissue is provided, the method comprising administering a synthetic gene, a vector, and/or a pharmaceutical composition of the present invention encoding a protein or nucleic acid of interest encoded by the endogenous gene, thereby treating the disease. In some embodiments, the present invention can be administered to target tissues. In some embodiments, the present invention can be administered to target and off-target tissues, thereby inhibiting expression of the synthetic gene in off-target tissues and endogenously regulating expression of the synthetic gene in target tissues.

In some embodiments, the method of treating a disease may further comprise the step of genetically knocking down and/or knocking out an endogenous gene encoding the protein or nucleic acid of interest in the subject. In some embodiments, the endogenous gene encoding the protein or nucleic acid of interest is MECP2. Genetically knocking down or "knock down of," or knocking out or "knock out of" an endogenous gene can be performed with any technique or method known currently or later identified in the art, including but not limited to using RNAi, Transcription Activator-like Effectors and Nucleases (TALE and TALEN), or Clustered Regularly Interspaced Short Palindromic Repeats (CRISPR-cas9) methods to introduce a matching shRNA, TALE or TALEN, or CRISPR/cas9 expression vector into the subject, tissue, and/or cell expressing the endogenous gene, thereby removing or reducing the expression of the endogenous nucleic acid or protein of interest relative to the expression of the endogenous nucleic acid or protein without the treatment of RNAi, TALE, TALEN, or CRISPR/cas9. These techniques and others are reviewed in Boettcher and McManus 2015 *Mol. Cell* 58(4):575-585, and U.S. Pat. No. 7,195,916 to Qin et al., 8,440,431 to Voytas et al., U.S. Pat. No. 8,889,356 to Zhang, U.S. Pat. No. 8,871,445 to Cong et al., and 10,000,772 to Doudna et al, each incorporated herein by reference in its entirety.

In an additional embodiment of the present invention, a method of treating a disease associated with abnormal expression of an endogenous gene or expression of a mutant protein encoded by an endogenous gene in a subject is provided, the method comprising the steps of genetically knocking down the endogenous gene in a cell of the subject, and administering the synthetic gene, vector, pharmaceutical composition of the present invention encoding a protein or nucleic acid of interest encoded by the endogenous gene, thereby treating the disease.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g. horse, cow, pig, goat, sheep). In some embodiments, the patient, subject or individual is a human. In some embodiments, the patient, subject or individual is at risk for an intellectual ability gene-dose sensitive disorder. In some embodiments, the patient, subject, or individual is at risk for Rett syndrome. As a further option, the subject can be a laboratory animal and/or an animal model of disease.

A further aspect of the invention relates to a method of treating a disorder associated with aberrant expression of a nucleic acid or protein of interest in a subject in need thereof, comprising delivering to the subject a therapeutically effective amount of the synthetic gene, vector, and/or pharmaceutical composition of the invention, thereby treating the disorder associated with aberrant expression of the nucleic acid or protein of interest in the subject. In some embodiments, the nucleic acids or proteins of interest are associated with intellectual ability gene-dose sensitive disorders. Nucleic acids or proteins of interest associated with intellectual ability gene-dose sensitive disorders include but are not limited to TCF4, UBE3A, DYRK1A, MEF2C, NSD1, ZEB2, MBD5, RPS6KA3, ATRX, FOXG1, AKT3, SLC6A1, MECP2 or any active fragment thereof.

Intellectual ability gene-dose sensitive disorders include, but are not limited to Rett syndrome, MeCP2 duplication syndrome, Angelman syndrome, dup15Q, DYRK1A haploinsufficiency, Down syndrome, MEF2C haploinsufficiency syndrome, dup5Q14.3, Sotos syndrome, Reverse Sotos syndrome, Alpha-thalassemia X-linked intellectual disability syndrome, Xq13.2q21.1 duplication, Coffin-Lowry syndrome, Xp22.12 duplication, Pitt Hopkins syndrome, Mowat-Wilson Syndrome, 2q22.3 triplication, 2q23.1 duplication, 2q23.1 microdeletion, FOXG1 syndrome, West Syndrome, megalencephaly-polymicrogyria-polydactyly-hydrocephalus syndrome, AKT3 duplication, Doose syndrome, SLC6A1 duplication, and Trisomy 18. In some embodiments, the nucleic acid or protein of interest is MECP2 or any active fragment thereof, and the intellectual ability gene-dose sensitive disorders associated with MECP2 are Rett Syndrome and/or MeCP2 duplication syndrome.

In certain embodiments, the synthetic gene, vector, and/or pharmaceutical composition is delivered to the subject, e.g., systemically (e.g., intravenously) or directly to the central nervous system (e.g., to the cerebrospinal fluid by intrathecal, intracisternal, or intraventricular injection) of the subject. In some embodiments, the synthetic gene, vector, and/or pharmaceutical composition is delivered by a delivery route selected from enteral, parenteral, intrathecal, intracisternal, intracerebral, intraventricular, intranasal, intra-aural, intra-ocular, peri-ocular, intrarectal, intramuscular, intraperitoneal, intravenous, oral, sublingual, subcutaneous and transdermal. In some embodiments, the synthetic gene, vector, and/or pharmaceutical composition is delivered intravenously. In some embodiments, the synthetic gene, vector, and/or pharmaceutical composition is delivered intravenously, intracisternally, intrathecally, and/or intraventricularly to be delivered directly to the cerebrospinal fluid ("intraCSF").

One aspect of the present invention is a method of transferring a synthetic gene to a cell in vitro. The synthetic gene and/or vector of the invention may be introduced to the cells in the appropriate amount. In embodiments of a virus vector, the virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^2$ infectious units, more preferably at least about $10^2$, $10^3$, $10^4$, $10^5$, $10^6$, $10^7$, $10^8$, $10^9$, $10^{10}$, $10^{11}$, $10^{12}$, or $10^{13}$ infectious units are introduced to the cell.

The cell(s) into which the synthetic gene and/or vector of the invention, e.g., virus vector, can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). Moreover, the cells can be from any species of origin, as indicated above.

The synthetic gene or vector of the invention, e.g., virus vector, may be introduced to cells in vitro for the purpose of administering the modified cell to a subject. In particular embodiments, the cells have been removed from a subject, the synthetic gene and/or vector of the invention, e.g., virus vector, is introduced therein, and the cells are then replaced back into the subject. Methods of removing cells from subject for treatment ex vivo, followed by introduction back into the subject are known in the art (see. e.g., U.S. Pat. No. 5,399,346). Alternatively, synthetic gene and/or vector of the invention, e.g., virus vector, is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the vector are administered to the subject in an effective amount in combination with a pharmaceutical carrier.

Human subjects include neonates, infants, juveniles, and adults. Optionally, the subject is "in need of" the methods of the present invention, e.g., because the subject has or is believed at risk for a disorder including those described herein or that would benefit from the delivery of a synthetic gene including those described herein.

In certain embodiments, the synthetic gene of the invention is administered to a subject in need thereof as early as possible in the life of the subject, e.g., as soon as the subject is diagnosed with aberrant expression or activity of a nucleic acid or protein of interest. In some embodiments, the synthetic gene is administered to a newborn subject, e.g., after newborn screening has identified aberrant expression or activity of a nucleic acid or protein of interest. In some embodiments, the synthetic gene is administered to a fetus in utero, e.g., after prenatal screening has identified aberrant expression or activity. In some embodiments, the synthetic gene is administered to a subject as soon as the subject develops symptoms associated with aberrant expression or activity of a nucleic acid or protein of interest, or is suspected or diagnosed as having aberrant expression or activity of a nucleic acid or protein of interest. In some embodiments, the synthetic gene is administered to a subject before the subject develops symptoms associated with aberrant expression or activity of a nucleic acid or protein of interest, e.g., a subject that is suspected or diagnosed as having aberrant expression or activity but has not started to exhibit symptoms.

A further aspect of the invention is a method of delivering the synthetic gene, vector, and/or pharmaceutical composition of the invention, e.g., the synthetic gene of the invention, to a subject. In particular embodiments, the method comprises a method of delivering a synthetic gene to an animal subject, the method comprising: administering an effective amount of a synthetic gene according to the invention to an animal subject. Administration of the synthetic gene of the present invention to a human subject or an animal in need thereof can be by any means known in the art. Optionally, the synthetic gene and/or vector are delivered in an effective dose in a pharmaceutically acceptable carrier.

Dosages of vectors to be administered to a subject will depend upon the mode of administration, the disease or condition to be treated, the individual subject's condition, the particular viral vector, and the nucleic acid to be delivered, and can be determined in a routine manner. In embodiments of a viral vector, exemplary doses for achieving therapeutic effects are virus titers of at least about $10^2$, $10^3$, $10^4$, $10^5$, $10^6$, $10^7$, $10^8$, $10^9$, $10^{10}$, $10^{11}$, $10^{12}$, $10^3$, $10^{14}$, $10^{15}$, $10^{16}$ transducing units or more. Doses and virus titer transducing units may be calculated as vector or viral genomes (vg).

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

In some embodiments, the vector is administered to the CNS, the peripheral nervous system, or both.

In some embodiments, the vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. For example, controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the vector in a local rather than systemic manner, for example, in a depot or sustained-release formulation. Further, the viral vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical compositions according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see. e.g., *Pharm. Res.* 3:318 (1986)) and typically take the form of an optionally buffered aqueous solution of the composition of this invention. Suitable formulations can comprise citrate or bis\tris buffer (pH 6) or ethanol/water.

The vectors disclosed herein may be administered to the lungs of a subject by any suitable means, for example, by administering an aerosol suspension of respirable particles comprised of the vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLES

Example 1: Identification of miRNAs Upregulated by MECP2 Expression

To identify endogenous miRNAs upregulated by supraphysiological MeCP2 expression, cerebellar and medullar RNA from mice treated with a toxic dose of MECP2 vector were screened. Mecp2+/y and Mecp2−/y mice were injected intracisternally with either saline or $1\times10^{12}$ vector genomes (vg) of AAV9/MeP426-hMECP2-myc-RDH1pA (postnatal day 28 [PND28]; 10 µL injection volume; n=2 mice per treatment). Two weeks after treatment, mice were euthanized with a lethal dose of tribromoethanol. The cerebellum and brain stem were dissected, frozen on dry ice, and immediately transferred to −80° C. for storage. A Qiagen miRNeasy Mini Kit was used to purify total RNA from thawed cerebellum and brainstem (combined). Purified RNA was stored at −80° C. and later shipped on dry ice to LC Sciences for screening (microarray part number MRA-1002; miRBase version 21).

Raw data was processed by LC Sciences according to their technical bulletin (Sciences, L. microRNA Microarray Data Analysis). The small sample sizes used in the pilot study precluded the identification of positive hits based solely on statistically significant differences between treatment groups. Thus, to improve statistical power, data was aggregated for all 3 MECP2(+) groups (i.e., virus-treated Mecp2−/y mice as well as saline- and virus-treated Mecp2+/y mice) prior to calculating statistical significance. Among 10 moderately to highly expressed miRNAs with elevated levels among MECP2(+) mice, one miRNA (miR-494-3p) has targets within the endogenous MECP2 3'UTR (targetscan.org; Agarwal et al. 2015 Elife (4); mouse and human), suggesting that a negative feedback loop mediated by MeCP2 and miR-494-3p may exist in vivo. Furthermore, the normalized signal intensities demonstrated a compelling trend between increased miR-494-3p expression and exogenous MeCP2 expression in both Mecp2+/y and Mecp2−/y mice.

Example 2: Identification of Additional miRNAs Upregulated by MeCP2 Expression

Figure 8:
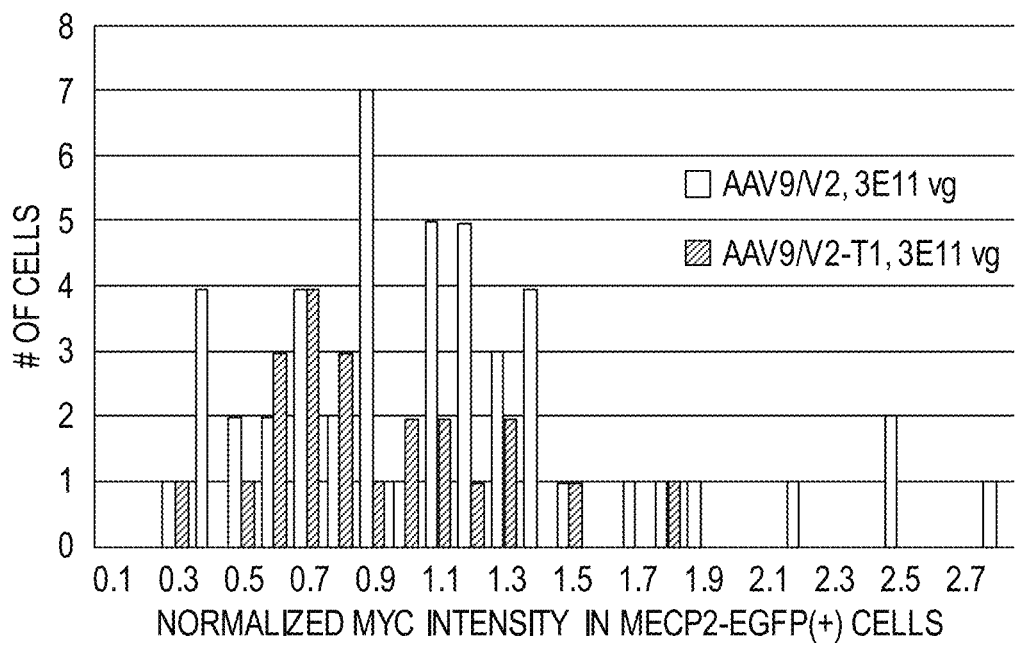
FIG. 8 shows that insertion of mir-494-3p targets into the "V2" viral genome slightly (not significantly) decreases exogenous MeCP2 expression in MeCP2-EGFP(+) cells (vs. MeCP2-null cells). After miR-494-3p was identified as a positive hit in a 2016 pilot study, 3 tandem targets were inserted in the 3'UTR of the MeP426-hMECP2-myc-RDH1pA viral genome (targets for miR-132, miR-19, and miR-22 were removed). The modified viral genome was packaged into AAV9 (AAV9/V2-T1) and injected into mosaic MECP2EGFP-fusion/null mice. Transgene expression was slightly decreased in MeCP2-EGFP(+) cells, compared to that observed in the neighboring null cells.

Three miRNA targets in the MeP426-hMECP2-myc-RDH1pA viral genome (i.e., miR-22-3p, miR-19-3p, and miR-132-3p) were replaced with a target sequence for miR-494-3p (Sinnett et al. 2017 Mol. Ther. Methods Clin. Dev. (5):106-115; Gadalla et al. 2017 Mol. Ther. Methods Clin. Dev. (5):180-190). The modified viral genome was then packaged into AAV9 and injected intracisternally into mosaic MECP2-EGFP-fusion/null females. Transgene expression was slightly decreased in response to MeCP2-EGFP expression compared to that observed in neighboring null cells (FIG. 8).

Example 3: Large-Scale Screening of Upregulated miRNAs

A large-scale screen was completed to address the limitations of the pilot study described above. More specifically, additional control groups were added, more mice were treated, and brain regions were finely dissected (not combined) prior to RNA purification. Mecp2+/y and Mecp2−/y mice were injected intracisternally with either saline, $1\times10^{12}$ vg AAV9/MeP426-hMECP2-myc-RDH1 Pa, or $1\times10^{12}$ vg AAV9/CBH-EGFP (PND P28-P35; 10 µL injection volume; n=3 mice per treatment). 2-3 weeks after treatment, mice were euthanized with a lethal dose of tribromoethanol. Cervical spinal cord, cerebellum, and brain stem were dissected, frozen on dry ice, and immediately transferred to −80° C. for storage. A Qiagen miRNeasy Mini Kit was then used to purify total RNA from thawed tissue. Brain regions were not combined prior to RNA purification. RNA was stored at −80° C. and later shipped on dry ice to LC Sciences for screening (microarray part number MRA-1002; miR-Base version 21).

Raw data was processed by LC Sciences according to their technical bulletin. miRNAs that were significantly upregulated in correlation with endogenous MeCP2, AAV9/MECP2, or AAV9/EGFP treatment were identified (FIGS. 2-7). Mean expression levels of mmu-let-7e-5p, mmu-miR-451a, and mmu-miR-690 increased most frequently in correlation with exogenous and endogenous MeCP2; and increased least frequently in correlation with AAV9/EGFP across tissue types in Mecp2+/y and Mecp2−/y mice.

Figure 9:
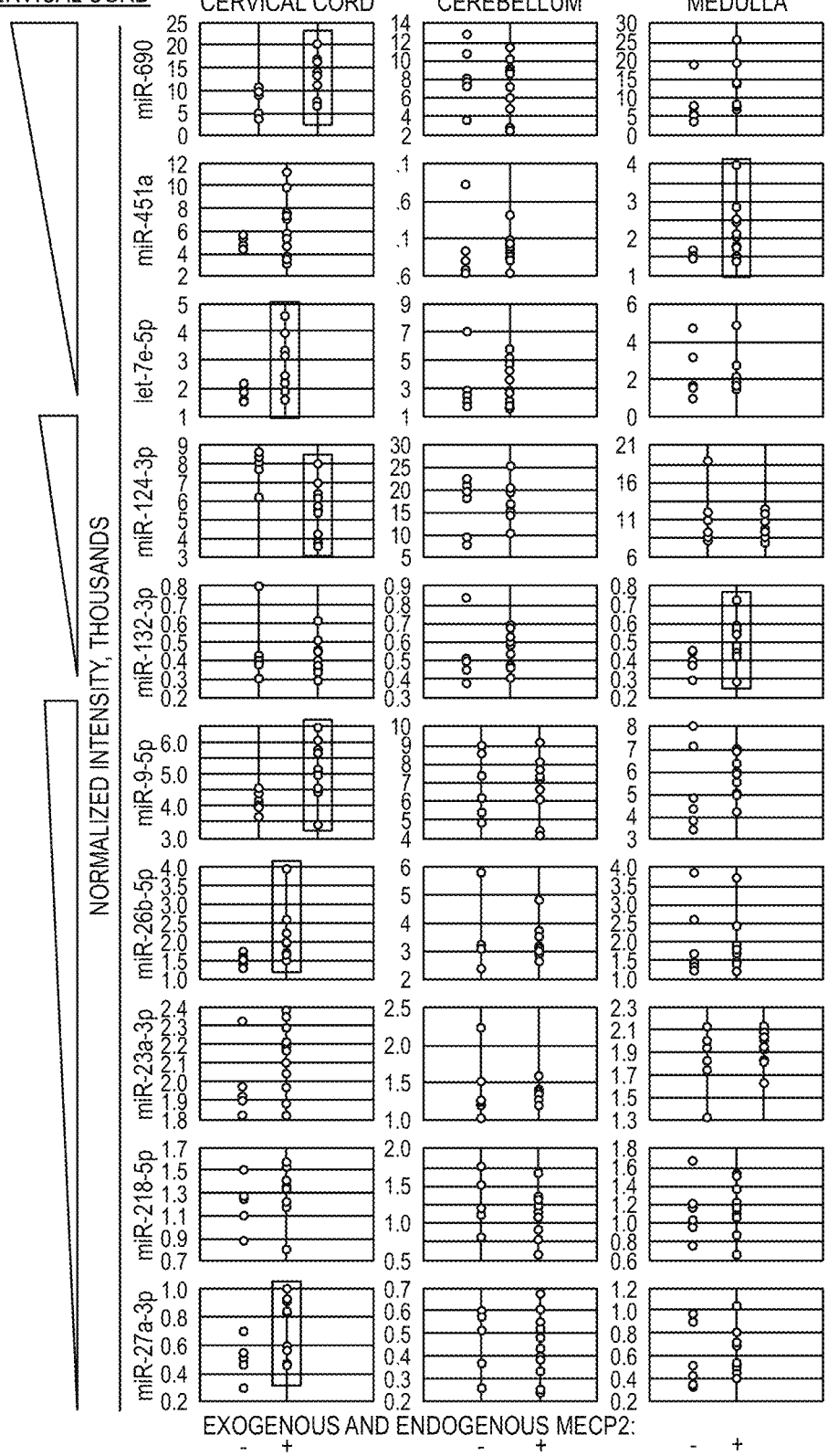
FIG. 9 shows miRNAs upregulated in correlation with aggregated MECP2 expression. The MECP2 (−) group shows data points for saline- and AAV9/EGFP-treated KO mice. The MECP2(+) group shows data points for saline-, AAV9/MECP2−, and AAV9/EGFP-treated WT mice as well as AAV9/MECP2-treated KO mice. Boxes indicate significant differences.

Analysis of aggregated treatment groups (MECP2(−) vs. MECP2(+)) revealed additional miRNAs that were significantly upregulated by MeCP2 expression in at least 1 tissue type (FIG. 9). In regard to miR-690, there was a significant difference between MECP2(−) and (+) group sin the cervical cord, and a significant difference between saline-treated KO and WT mice in the medulla. In regard to miR-451a, there was a significant difference between MECP2(−) and (+) groups in the medulla, and a significant difference between saline-treated KO and WT mice in the cervical cord. In regard to let-7e5p, there was a significant difference between MECP2(−) and (+) groups in the cervical cord, and a significant difference between saline-treated KO and WT mice in the cervical cord as well. Let-7e-5p may be a reasonable target for the cerebellum, considering relative expression level and potential outlier data point that may mask significance. These three targets (miR-690, miR-451a, and Let-7e-5p were added to the MeP426-ΔNIC-RDH1pA. In regard to miR-124-3p, it was lower in the aggregated MECP2(+) group in the cervical cord, and consistent with previous analysis in cervical cord of saline-treated KO and WT mice. Despite this inverse relationship, the relatively high expression throughout the brain means this target may be reasonable for capping expression regardless of injection route. In regard to miR-132-3p, it was found upregulated in the medulla in aggregate analyses only. miR-124-3p and miR-132-3p are published targets in RDH1pA. miR-9-5p, miR-26b-5p, miR-23a-3p, miR-218-5p, and miR-27a-3p are part of the universal panel (as well as let-7e-5p). In regard to miR-9-5p and miR-27a-3p, these were upregulated in the cervical cord in aggregated analyses only. In regard to miR-26b-5p, there was a significant difference between MECP2(−) and (+) groups in the cervical cord, and a significant difference between saline-treated KO and WT mice in the cervical cord as well. Most of the miRNAs of FIG. 9 are normally expressed at higher levels than that of miR-494-3p, suggesting that new panel designs may yield more robust inhibition of transgene expression.

Data from the screens were used to design 2 types of miRNA target panels. The first panel binds miRNAs whose expression levels increase in correlation with MeCP2 expression in vivo, as further described in Example 4. The second panel design is described below.

RNA samples from saline- and virus-treated mice were screened to identify MeCP2-driven miRNAs expressed in the central nervous system (CNS) were screened. Insertion of targets for these miRNAs into the 3'UTR of a MECP2 viral genome allows for use of endogenous RNA interference mechanisms to attenuate toxic overexpression of exogenous MeCP2 in vivo (FIG. 1). Data from recent screens was used to design 2 types of miRNA target panels. The first panel binds miRNAs whose expression levels increase in correlation with MeCP2 expression in vivo. The second panel design includes targets that are justified by both literature and experimental data. Importantly, the targets in this second panel are conserved in the 3' UTRs of many dose-sensitive genes that mediate intellectual ability. Thus, this panel may be ideal for testing in mouse models of Rett syndrome (RTT) as well as other neurodevelopmental disorders, and could mediate improved feedback-regulation of the transgene in a therapeutic setting.

The complete panel sequence is listed below. Seed matches are underlined; every other seed match and flanking sequences section is italicized. Binding site key (in order 5'-3'): miR-9-5p; miR-26-5p; miR-23-3p; miR-218-5p; miR-27-3p; let-7-5p:

(SEQ ID NO: 1)
5' *CTGTTCTAGCCC*CCAAAGA*GTTTTCTGTGCTTGCTTTTGAAA*CTTGAA

*GTCTTGAAAAC*CAAAGA*CATAGA*TGTGAA*AATTTTAGGCAGTGTAAGCTG

*ATA*GCACAA*GTTCTGGCGACT*CACAATTAT*GCTGTGAA*TTTTA*CAAAAAG*

*AAGCAGTAAT*CTACCTCAGCC*GATAAC*-3'

A number of neurodevelopmental disorders characterized by intellectual disability are mediated by mutations in genes that must be tightly regulated (see Table 1). Similarities among the 3' UTRs of these genes suggests that there may be an in vivo inhibitory mechanism to help protect the brain from overexpression-induced intellectual disability, regardless of genetic etiology (see Table 2).

TABLE 1

Selected dose-sensitive genes mediating disorders characterized by intellectual disability.

| Loss-of-function syndrome | Gene | Overexpression syndrome (mediated either wholly or in part by the genes listed) |
|---|---|---|
| Rett Syndrome | MECP2 | MeCP2 Duplication Syndrome |
| Angelman Syndrome | UBE3A | dup15Q |
| DYRK1A haploinsufficiency | DYRK1A | Down Syndrome |
| MEF2C haploinsufficiency syndrome | MEF2C | dup5Q14.3 |
| Sotos syndrome | NSD1 | "reverse" Sotos syndrome |
| Alpha-thalassemia X-linked intellectual disability syndrome | ATRX | Xq13.2q21.1 duplication |
| Coffin-Lowry Syndrome | RPS6KA3 | Xp22.12 duplication |
| Pitt Hopkins Syndrome | TCF4 | Trisomy 18 |
| 2q23.1 Microdeletion Syndrome | MBD5 | 2q23.1 duplication |
| Mowat-Wilson Syndrome | ZEB2 | 2q22.3 triplication |

Deletion and reciprocal duplication disorders mediating similar phenotypes (e.g., intellectual disability, speech abnormalities, seizures, microcephaly, and/or stereotypy) include but are not limited to those listed in Table 1. The severe phenotypes of these duplication disorders justify the need for a broadly applicable miRNA target panel for regulating transgene expression after gene therapy.

References describing human and animal models of deletion or mutation disorders in Table 1: TCF4 (Agarwal 2015; Dean L. 2012 *Medical Genetics Summaries*, Bethesda MD; Sweetser et al. 1993 *GeneReviews((R))*, Seattle WA; de Winter et al. 2016 *Orphanet J. Rare Dis.* 11:37); MECP2 (Leonard et al. 2017 *Nat. Rev. Neurol.* 13(1):37-51; Chahil and Bollu 2018 *StatPearls*: Treasure Island FL; Seltzer and Paciorkowski 2014 *Am. J. Med. Genet. C. Semin. Med. Genet.* 166C(2):140-155; Fuertes-Gonzales et al. 2011 *Med. Oral Patol. Oral Cir. Bucal.* 16(1):e37-41); UBE3A (Dagli et al. 1993 *GeneReviews((R))*: Seattle WA; Pelc et al. 2008 *Neuropsychiatr. Dis. Treat.* 4(3):577-584; Pelc et al. 2008 *Sleep Med.* 9(4):434-441); DYRK1A (Luco et al. 2016 *BMC Med. Genet.* 17:15); MEF2C(Vrecar et al. 2017 *J. Pediatr. Genet.* 6(3):129-141); NSD1 (Tatton-Brown et al. 1993 *GeneReviews((R))*: Seattle WA); ATRX (Stevenson R. E. 1993 *GeneReviews((R))*: Seattle WA; Bouazzi et al. 2016 *Indian J. Med. Res.* 143(1):43-48); RPS6KA3 (Miyata et al. 2018 *Brain Dev.* 40(7):566-569; Morino et al. 2016 *Medicine (Baltimore)* 95(31):e4468; Touraine et al. 2002 *Eur. J. Pediatr.* 161(4):179-187; Tos et al. 2015 *Genet. Couns.* 26(1):47-52); MBD5 (Talkowski et al. 2011 *Am. J. Hum. Genet.* 89(4):551-563); ZEB2 (Hegarty et al. 2015 *Prog. Neurobiol.* 132:81-95).

References describing human and animal models of overexpression (monogenic or polygenic) in Table 1: Trisomy 18 (Roberts et al. 2016 *Clin. Anat.* 29(5):628-632; de Queiroz et al. 2007*J. Dent. Child (Chic)* 74(1):67-72); MeCP2 duplication syndrome (Miguet et al. 2018. *J. Med. Genet.* 55(6): 359-371); Dup15Q (Finucane et al. 1993 *GeneReviews((R))*: Seattle WA; Copping et al. 2017 *Hum. Mol. Genet.* 26(20): 3995-4010; Wegiel et al. 2012*J. Neuropathol. Exp. Neurol.* 71(5):382-397); Down Syndrome (Duchon and Herault 2016 *Front. Behav. Neurosci.* 10:104; Kent and Vorperian 2013.1 *J. Speech Lang. Hear. Res.* 56(1):178-210; Araujo et al. 2015 *Epilepsy Behav.* 53:120-125; Guedj et al. 2012 *Neurobiol. Dis.* 46(1):190-203; Carter et al. 2008 *Neuroreport* 19(6):653-656); dup5Q14.3 (Cesaretti et al. 2016 Am. *J. Med. Genet. A* 170A(5):1352-1357); reverse Sotos syndrome (Rosenfeld et al. 2013 *Mol. Syndromol.* 3(6):247-254); Xq13.2q21.1 (Lugtenberg et al. 2009 *Am. J. Med. Genet. A* 149A(4):760-766; Berube et al. 2002 *Hum. Mol. Genet.* 11(3):253-261); Xp22.12 (Matsumoto et al. 2013 J. Hum. Genet. 58(11):755-757; Tejada et al. 2011 *Pediatrics* 128(4):e1029-1033); 2q23.1 duplication (Mullegamna et al. 2014 *Eur. J. Hum. Genet.* 22(1):57-63); 2q22.3 triplication (Yuan et al. 2015 *Mol. Cytogenet.* 8:99).

TABLE 2

Selected list of common miRNA targets among 3' UTRs of selected genes mediating intellectual ability.

| Targets in 3' UTR in vivo | TCF4 | MECP2 | UBE3A | DYRK1A | MEF2C | NSD1 | MBD5 | ATRX | ZEB2 | RPS6KA3 |
|---|---|---|---|---|---|---|---|---|---|---|
| miR-124-3p.1 | 90/87 # | 79/76 # | 86/85 # | 75/— | X | X | X | X | X | X |
| miR-124-3p.2 | 31/— | 87/82 # | X | 68/— | 57/— | X | X | 77/74 β | 58/45 # | X |
| miR-30-5p | 36/25 # | 27/27 # | 60/— | 81/— | 66/— β | 15/15 | 64/— | —/15 | 76/79 # | X |
| miR-451a | —/62 | X | X | X | X | X | X | X | X | X |

TABLE 2-continued

Selected list of common miRNA targets among 3' UTRs of selected genes mediating intellectual ability.

| Targets in 3' UTR in vivo | TCF4 | MECP2 | UBE3A | DYRK1A | MEF2C | NSD1 | MBD5 | ATRX | ZEB2 | RPS6KA3 |
|---|---|---|---|---|---|---|---|---|---|---|
| miR-9-5p | 75/41 β | 55/— | 88/82 # | | 95/94 # | 96/94 # | —/28 | 81/79 # | X | 63/52 # | —/28 |
| miR-26-5p | 50/49 # | 25/20 # | 93/89 # | 95/93 # | 72/57 # | 25/— | 38/43 | 50/49 β | 44/54 # | —/31 |
| miR-23-3p | 48/— | 26/29 # | 26/53 β | 80/70 β | 52/55 # | 26/— | 94/82 # | 51/66 # | 26/29 # | 38/— |
| miR-218-5p | 89/78 # | 66/69 # | 86/86 # | —/59 | 94/94 # | X | 80/— | 80/— | 95/94 | 92/87 # |
| miR-27-3p | 52/— | 82/86 # | X | 83/84 # | 92/91 # | 89/54 # | 82/54 β | 71/56 # | 76/73 # | —/53 |
| let-7-5p/98-5p | X | 56/55 # | X | 83/85 # | 68/67 # | 73/60 β | 28/46 β | X | X | 81/75 # |
| miR-494-3p | —/37 | 51/68 β | 33/37 # | 64/54 β | —/55 | 33/68 β | 86/55 # | 64/68 # | 33/37 # | 81/37 β |

A complete list of targets in endogenous 3'UTRs can be found at targetscan.org. In each cell of Table 2, the context++ percentile score is listed for two species (human/mouse). High scores indicate targets with favorable genomic context. The synthetic panel includes targets for miRNAs predicted to bind many of the endogenous 3' UTRs listed above. Of the 6 selected targets, 4 targets should bind miRNAs (miR-9-5p, miR-26b-5p, miR-27-3p, and let-7-5p) that demonstrated increased expression in correlation with MeCP2 expression (see HTS data in FIG. 9). In addition, correlations between MeCP2 expression and let-7 (Urdinguio et al. 2010 *Epigenetics* 5(7):656-663; Wu et al. 2010 *Proc. Natl. Acad. Sci. U.S.A.* 107(42):18161-18166); between TCF4 expression and miR-218 (Hassan et al. 2012 *J. Biol. Chem.* 287(50):42084-42092); and between miR-23a-3 and MEF2C expression have been published (Kalsotra et al. 2014 *Cell Rep.* 6(2):336-345). Unpublished HTS data demonstrated a trend in increased miR-23a-3p expression and MeCP2 expression in cervical cord. Other targets were excluded for the following reasons: (1) The target has a modest effect on transgene expression (i.e., miR-494-3p; see FIG. 8); (2) The target does not appear in the UTRs examined above (i.e., miR-451a); (3) The corresponding miRNA is upregulated in correlation with AAV9/EGFP (i.e., miR-30c-5p); or (4) The target is already present as a component of the synthetic distal MECP2 pA in the published MECP2 viral genome (i.e., miR-124-3p) (Sinnett et al. 2017; Gadalla et al. 2017). X indicates no targets in either human or mouse 3' UTR. Boxes containing —/— indicate target is in either human (/—) or mouse (—/) 3'UTR only. The remaining targets appear in both species. Targets with 5' flanking sequences that are similar or identical across species are indicated with a # symbol. Targets that do not have conserved 5' flanking sequences are indicated with a β symbol. Targets (and their flanking sequences) outlined in bold were selected for the synthetic panel. Finally, targets for miR-29-3p, miR-338-3p, miR-98-5p, and miR-7-5p may also be candidates for insertion into a universal target panel, as binding sites for these miRNAs are present in many of the genes listed above (see targetscan.org), and increased expression of these miRNAs was observed in correlation with MeCP2 expression.

TABLE 3

Assessment of miRNA targets and their human genomic context.

| GENE | 5' flanking sequence | miR-9-5p target | 3' flanking sequence |
|---|---|---|---|
| MECP2 | CUCCUGGCACU- (SEQ ID NO: 3) (36% AU) | ACCAAAG- | GACACUUAUCCA (SEQ ID NO: 4) (58% AU) |
| UBE3A | CUGUUCUAGCCC (SEQ ID NO: 5) (42% AU; WC M12-M15) | -CCAAAGA | -GUUUUCUGUGC (SEQ ID NO: 6) (55% AU) |

TABLE 3-continued

Assessment of miRNA targets and their human genomic context.

| DYRK1A | UAAUUUAUUGU- (SEQ ID NO: 7) (91% AU) | ACCAAAG- | CUGUUUUAUAG (SEQ ID NO: 8) (75% AU) |
|---|---|---|---|
| MEF2C | AAUAUGUUUUA- (SEQ ID NO: 9) (91% AU) | ACCAAAGA | -UGUGGAGCAAU (SEQ ID NO: 10) (55% AU) |
| MBD5 | CAUUUGCAUUAG (SEQ ID NO: 11) (67% AU) | -CCAAAGA | -GAUAAGAACAU (SEQ ID NO: 12) (73% AU) |
| ZEB2 | GGGGAAAAAAC- (SEQ ID NO: 13) (55% AU) | ACCAAAGA | -AUUCACAUGGG (SEQ ID NO: 14) (55% AU) |
| TCF4 | UUUAUGAAAUUU (SEQ ID NO: 15) (92% AU) | -CCAAAGA | -UUUUGGUUGAU (SEQ ID NO: 16) (73% AU) |
| vg | CTGTTCTAGCCC (SEQ ID NO: 17) (42% AT; WC M12-M15) | -CCAAAGA | -GTTTTCTGTGC (SEQ ID NO: 18) (55% AT) |

| GENE | 5' flanking sequence | miR-26-5p target | 3' flanking sequence |
|---|---|---|---|
| MECP2 | -AGGCUUGCAGA (SEQ ID NO: 19) | -ACUUGAA (45% AU) | GCCUGCUCCUU (SEQ ID NO: 20) (36% AU) |
| UBE3A | -UUGCUUUUGAA (SEQ ID NO: 21) (73% AU) | -ACUUGAA | GUCUUUGAAAAC (SEQ ID NO: 22) (64% AU) |
| DYRKL4 | -UUUUUUUUUUA (SEQ ID NO: 23) (100% AU) | -ACUUGAA | AAGAUUGCAAA (SEQ ID NO: 24) (73% AU) |
| MEF2C | -AAGAAGAAGCC (SEQ ID NO: 25) (55% AU) | -ACUUGAA | CCCUCAAUAAA (SEQ ID NO: 26) (64% AU) |
| NSD1 | -GAGGUUGAGAC (SEQ ID NO: 27) (45% AU) | -ACUUGAA | CUCAGGCAGAG (SEQ ID NO: 28) (36% AU) |
| ATRX | ACAAUUUUGGU- (SEQ ID NO: 29) (73% AU) | UACUUGAA | UUGUUAAAGAA (SEQ ID NO: 30) (82% AU) |
| MBD5 | -AAAAGAAAACA (SEQ ID NO: 31) (82% AU) | -ACUUGAA | CAUUUUCAAUA (SEQ ID NO: 32) (82% AU) |
| ZEB2 | -UCUGUGAAGGA (SEQ ID NO: 33) (55% AU) | -ACUUGAA | GUGAUGCAUGU (SEQ ID NO: 34) (55% AU) |
| TCF4 | -UUUCUCAUGGG (SEQ ID NO: 35) (55% AU) | -ACUUGAA | GUGGACUCAUC (SEQ ID NO: 36) (45% AU) |
| vg | -TTGCTTTTGAA (SEQ ID NO: 37) (73% AT) | -ACTTGAA | GTCTTGAAAAC (SEQ ID NO: 38) (64% AT) |

| GENE | 5' flanking sequence | miR-23-3p target | 3' flanking sequence |
|---|---|---|---|
| MECP2 | -UUUUUUAAUAC (SEQ ID NO: 39) (91% AU) | -AUGUGAA | -AGCAAAGAAUA (SEQ ID NO: 40) (73% AU) |
| UBE3A | -AAACAAAAAGC (SEQ ID NO: 41) (73% AU) | -AUGUGAA | -AGUGCACUUAA (SEQ ID NO: 42) (64% AU) |
| DYRK1A | AACACUAUGUA- (SEQ ID NO: 43) (73% AU) | AAUGUGAA | -UGGAAACUUGG (SEQ ID NO: 44) (55% AU) |
| MEF2C | CCUUCUCUUGG- (SEQ ID NO: 45) (45% AU) | AAUGUGAA | -GAUCUGUCGAU (SEQ ID NO: 46) (55% AU) |
| NSD1 | -UUUCCAAGGG (SEQ ID NO: 47) (55% AU; WC M14-M16) | -AUGUGAA | -UGGAGUGAAA (SEQ ID NO: 48) (64% AU) |
| ATRX | -CAAAGACAUAG (SEQ ID NO: 49) (64% AU) | -AUGUGAA | -AAUUUUAGGCA (SEQ ID NO: 50) (73% AU) |
| RPS6K43 | CAGCUGGUUCC- (SEQ ID NO: 51) (36% AU) | AAUGUGA- | CUGAGUGUUCUC (SEQ ID NO: 52) (50% AU) |
| MBD5 | AAGUAAGAAAA- (SEQ ID NO: 53) (82% AU) | AAUGUGAA | -ACAAAUGUAGA (SEQ ID NO: 54) (73% AU) |
| ZEB2 | -UUAUGACAUAU (SEQ ID NO: 55) (82% AU) | -AUGUGAA | -CACAUCACAAA (SEQ ID NO: 56) (64% AU) |
| TCF4 | -AUUUGGUUCAC (SEQ ID NO: 57) (64% AU) | -AUGUGAA | -GUGCCCUCCAU (SEQ ID NO: 58) (36% AU) |
| vg | -CAAAGACATAG (SEQ ID NO: 59) (64% AT) | -ATGTGAA | -AATTTTAGGCA (SEQ ID NO: 60) (73% AT) |

| GENE | 5' flanking sequence | miR-218-5p target | 3' flanking sequence |
|---|---|---|---|
| MECP2 | UUCUUACCGAC- (SEQ ID NO: 61) (55% AU; WC M12-M14) | AAGCACA- | GUCAGGUUGAAG (SEQ ID NO: 62) (50% AU) |
| UBE3A | AACUUUAGUAAC (SEQ ID NO: 63) (75% AU; WC M12-M15) | -AGCACAA | -CAAAUUAAAAA (SEQ ID NO: 64) (91% AU) |
| MEF2C | UUAAUGAGAAG- (SEQ ID NO: 65) (73% AU) | AAGCACAA | -UUUUGAUUUUG (SEQ ID NO: 66) (82% AU) |
| ATRX | GCACGAAUAUA- (SEQ ID NO: 67) (64% AU) | AAGCACA- | UCUCUUAACUGC (SEQ ID NO: 68) (58% AU) |
| RPS6KA3 | GUGUAAGCUGAU (SEQ ID NO: 69) (58% AU; WC M15-M19) | -AGCACAA | -GUUCUGGCGAC (SEQ ID NO: 70) (36% AU) |
| MBD5 | AAUAAGAAAUGU (SEQ ID NO: 71) (83% AU) | -AGCACAA | -CAUAAUUUCC (SEQ ID NO: 72) (73% AU) |

TABLE 3-continued

Assessment of miRNA targets and their human genomic context.

| GENE | 5' flanking sequence | miR-23b-3p target | 3' flanking sequence |
|---|---|---|---|
| ZEB2 | AUUUAUACUUU- (SEQ ID NO: 73) (91% AU; WC M15-M17) | AAGCACAA | -CUAGAAAAUUG (SEQ ID NO: 74) (73% AU) |
| TCF4 | UCAGCAUAAAC- (SEQ ID NO: 75) (64% AU) | AAGCACAA | -AAAUUUAGUCU (SEQ ID NO: 76) (82% AU) |
| vg | GTGTAAGCTGAT (SEQ ID NO: 77) (58% AT; WC M15-M19) | -AGCACAA | -GTTCTGGCGAC (SEQ ID NO: 78) (36% AT) |

| GENE | 5' flanking sequence | miR-27a-3p target | 3' flanking sequence |
|---|---|---|---|
| MECP2 | -GAUAAAUCUCU (SEQ ID NO: 79) (73% AU) | -CUGUGAA | -AGUGA (60% AU) |
| DYRK1A | -UCACAAUUAUG (SEQ ID NO: 80) (73% AU) | -CUGUGAA | -UUUUACAAAAA (SEQ ID NO: 81) (91% AU) |
| MEF2C | -UUUAAAAAAAU (SEQ ID NO: 82) (100% AU) | -CUGUGAA | -AUUAACAUGCU (SEQ ID NO: 83) (73% AU) |
| NSD1 | UCAUGAAAUAA- (SEQ ID NO: 84) (82% AU) | ACUGUGAA | -UUUGGGGGGGG (SEQ ID NO: 85) (27% AU) |
| ATRX | -AAAUCAUACAG (SEQ ID NO: 86) (73% AU) | -CUGUGAA | -GACUUGCCUUU (SEQ ID NO: 87) (55% AU) |
| MBD5 | ACAAACCUAAA- (SEQ ID NO: 88) (73% AU) | ACUGUGA- | GCCAUUGUAAA- (SEQ ID NO: 89) (64% AU) |
| ZEB2 | -UUUUUUUUUUU (SEQ ID NO: 90) (100% AU) | -CUGUGAA | -GGAACUUGAAG (SEQ ID NO: 91) (55% AU) |
| TCF4 | -UUGGGGCUUUC (SEQ ID NO: 92) (45% AU) | -CUGUGAA | -AUGUAUGAACA (SEQ ID NO: 93) (73% AU) |
| vg | -TCACAATTATG (SEQ ID NO: 94) (73% AT) | -CTGTGAA | -TTTTACAAAAA (SEQ ID NO: 95) (91% AT) |

| GENE | 5' flanking sequence | let-7e/98-5p target | 3' flanking sequence |
|---|---|---|---|
| MECP2 | GUUGUUAGUUA- (SEQ ID NO: 96) (73% AU) | CUACCUC- | CUCUCCUGACA- (SEQ ID NO: 97) (45% AU) |
| DYRK1A | GAAGCAGUAAU- (SEQ ID NO: 98) (64% AU) | CUACCUC- | UGCCGAUAACC- (SEQ ID NO: 99) (45% AU) |
| MEF2C | CAAAUUGAUUCA (SEQ ID NO: 100) (75% AU) | -UACCUCA- | GUUUAAUUCAG (SEQ ID NO: 101) (73% AU) |
| NSD1 | UCUGCCCCUCU- (SEQ ID NO: 102) (36% AU) | CUACCUC- | UUCCACUCAUG- (SEQ ID NO: 103) (55% AU) |
| MBD5 | CACUGUGUGUG- (SEQ ID NO: 104) (45% AU) | -UACCUCA | -GUGACCUUUUA (SEQ ID NO: 105) (64% AU) |
| RPS6KA3 | GAGCCUACUUC- (SEQ ID NO: 106) (45% AU) | CUACCUC- | UUAAGGCACUU- (SEQ ID NO: 107) (64% AU) |
| vg | GAAGCAGTAAT- (SEQ ID NO: 108) (64% AT) | CTACCTC- | AGCCGATAACC- (SEQ ID NO: 109) (45% AT) |

Targets and their flanking sequences, as they appear in human 3' UTRs, are shown next to each gene in Table 3. The sequence selected for the synthetic panel is listed next to "vg" (viral genome). If 2 or more targets for a given miRNA were present in the human 3' UTR, then the target sequence that was conserved across species was selected and listed in the table above. The following parameters were considered when selecting a 5' flanking sequence for the synthetic panel: (1) consequential Watson-Crick (WC) base-pairing (as predicted by Targetscan) with preferential pairing at messenger RNA (mRNA) nucleotides 13-16 (M13-M16) (Grimson et al. 2007 *Mol. Cell* 27(1):91-105); (2) conservation of the 5' flanking sequence across species (see Table 2); (3) the context++ percentile score listed on Targetscan; and (4) sequence complexity (commercial gene synthesis requires a % GC content no less than 35% for the entire synthetic panel). For each 5' flanking sequence selected, a 3' flanking sequence from the same UTR was selected for insertion into the target panel. (3) One mutation (highlighted and bolded) was introduced to create a T1A anchor to promote mRNA-Argonaute interactions (Schirle et al. 2015 *Elife* (4); Schirle et al. 2014 *Science* 346(6209):608-613). Due to similarity in miRNA sequences, the target for let-7e-5p may also bind other let-7 miRNAs. Let-7a-5p, let-7b-5p, and let-7g-5p showed increased expression in MECP2 (+) cervical cord tissue in aggregated data analyses; let-7c-5p, let-7d-5p, and let-7g-5p showed increased expression in Mecp2$^{-/y}$ mice after treatment with MECP2 virus. In addition, the let-7e-5p target may bind miR-98-5p, whose expression level increased in aggregated data analyses for cervical cord tissue. T1A anchors are underlined in the target column. T9A/Us, which are believed optimize to the conformation of Argonaute interactions, are underlined in the 5' flanking sequence column (Lewis et al. 2005 *Cell* 120(1): 15-20).

Figures 10A, 10B:
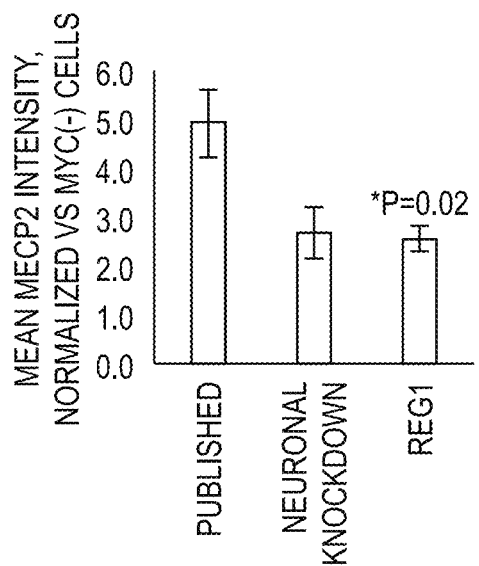

Compare to Table 2. The 3' UTRs of housekeeping genes have few of the targets examined, as shown in Table 4. Table 4 labeling follows as described for Table 2. Thus, the conservation of targets across genes mediating intellectual ability may be physiologically significant. A complete list of targets in endogenous 3'UTRs can be found at targetscan.org. In each cell of Table 4. the context++ percentile score is listed for two species (human/mouse). High scores indicate targets with favorable genomic context. ACTB, beta-actin; ATF1, activating transcription factor 1; DAD1, defender against cell death 1; DARS, aspartyl-tRNA synthetase; GAPDH, glyceraldehyde-3-phosphate dehydrogenase; HSPA4, heat shock protein family A (Hsp70) member 4; MRPL9, mitochondrial ribosomal protein L9; POLR1C, RNA polymerase I and III subunit C; PRKAG1, protein kinase AMP-activated non-catalytic subunit gamma 1; RPL5, ribosomal protein L5.

expression (mini+endogenous full-length) in transduced Purkinje cells was 5× that of non-transduced Purkinje cells, as shown in FIGS. 10A and 10B. The positive control panel for neuronal knockdown (featuring 3 targets for miR-124-

TABLE 4

Selected list of miRNA targets among 3' UTRs of housekeeping genes.

| Targets in 3' UTR in vivo | GAPDH | POLR1C | ATF1 | DAD1 | DARS | PRKAG1 | RPL5 | HSPA4 | MRPL9 | ACTB |
|---|---|---|---|---|---|---|---|---|---|---|
| miR-124-3p.1 | X | X | X | X | X | X | X | —/41 | X | X |
| miR-124-3p.2 | X | X | X | X | X | X | 58/— | —/46 | X | 90/88 # |
| miR-30-5p | X | X | 91/88 # | X | 15/— | X | 79/— | X | X | X |
| miR-451a | X | X | X | X | X | X | X | X | X | X |
| miR-9-5p | X | X | 97/89 # | X | X | X | X | 71/— | X | X |
| miR-26-5p | X | X | 84/— | X | 88/98 β | 89/— | 60/83 β | 88/88 # | X | X |
| miR-23-3p | X | X | X | X | X | 82/— | —/88 | X | X | X |
| miR-218-5p | X | X | X | X | X | 90/— | X | X | X | X |
| miR-27-3p | X | 83/— | 84/80 β | X | X | X | X | 33/— | X | X |
| let-7-5p/98-5p | X | X | X | X | X | X | X | X | X | X |
| miR-494-3p | X | 95/— | —/98 | X | 94/— | —/87 | X | X | X | X |

Example 4: Development of a RTT-Specific Construct

An additional construct was developed to be specific for RT, referred to herein as "reg1." The targets in this sequence correspond to miRNAs shown to be upregulated in correlation with MeCP2 expression in a high-throughput screen of brain and spinal cord RNA.

The sequence of reg1 is as follows. Seed matches are underlined; every other seed matches and flanking sequences section are italicized. Binding site key (in order 5'-3'): miR-451a; let-7-5p; miR-690.

(SEQ ID NO: 2)
5' *ATAAGGGCAGAAACGGTTC*ACATTCCATTCTGCCCCGGAC*CTACCTCC* CTCCCTCTCC*TTATCAAACCCTAGCCTTGCTTGTTAAAT*-3'

Figure 11:
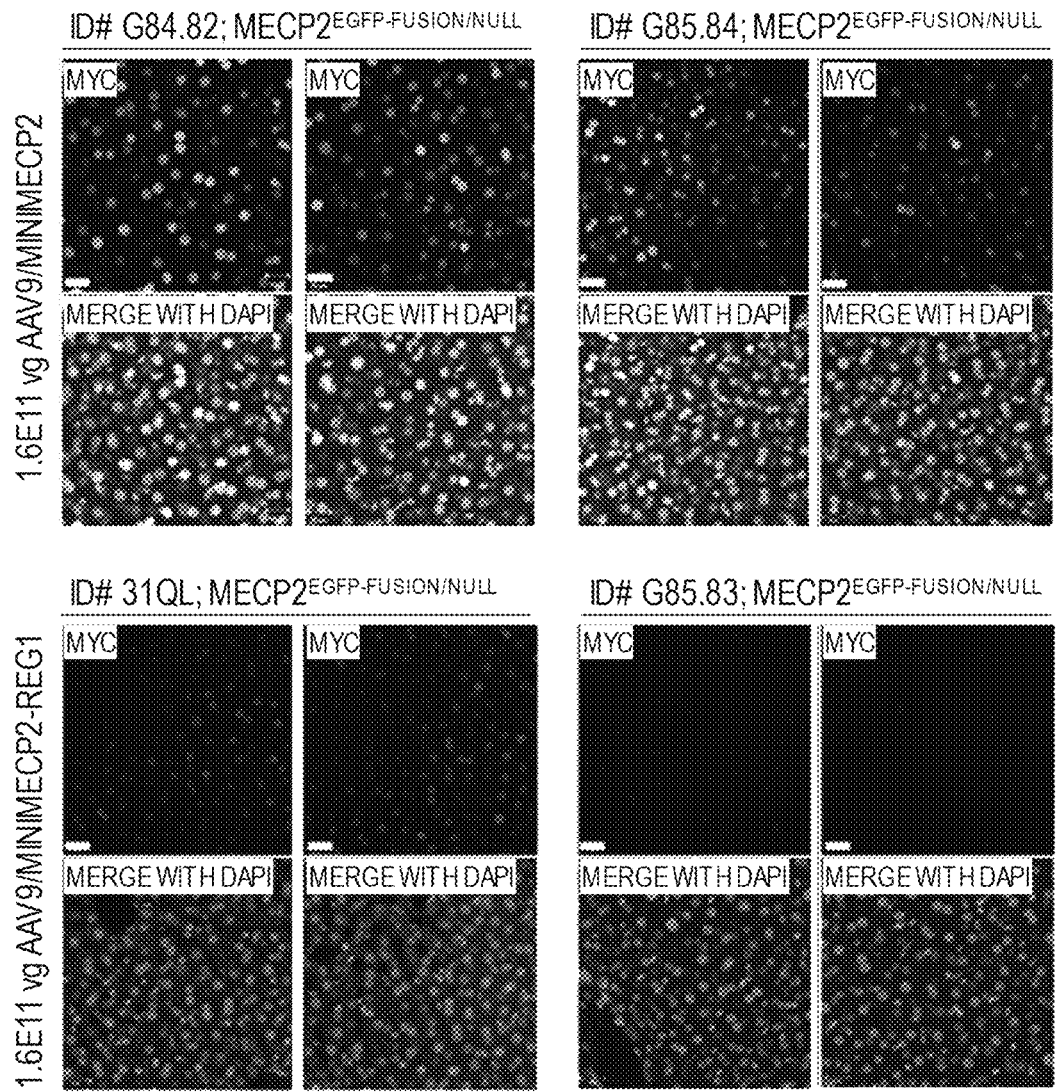
FIG. 11 shows preliminary data in which reg1 appears to decrease hepatic transgene expression after intracisternal administration of AAV9/mini-MECP2-reg1 in heterozygous mosaic female mice. Identical gain settings were used in all of the images shown. Scale bar indicates 20 μm. Each quadrant depicts one mouse, as indicated by ID number (ID #).

Reg1 was tested in WT mice and showed tightly regulated total MeCP2 expression in WT Purkinje cells, as shown in FIGS. 10A-10E. Purkinje cells are located close to the intracisternal injection site and are vulnerable to supraphysiological transgene expression. The corrected total cell fluorescence (anti-MeCP2 signal) for each nucleus was normalized to that of the mean MeCP2 signal for myc(−) Purkinje nuclei. The means presented for each mouse in FIG. 10A represent the normalized MeCP2 signal averaged across all myc(+) nuclei quantified for the specified host. Iterative averaging across cells within a Z-stack, then across Z-stacks within a single mouse, likewise yielded a significant decrease in total MeCP2 expression (vs. that observed for the published control AAV9/MeP426-miniMECP2-myc-RDH1 pA; Gadalla et al. 2017). The mean total MeCP2 3p) decreased overexpression by half (p=0.06). The reg1 cassette also decreased overexpression by half (p=0.02). FIG. 10C shows histograms of total MeCP2 intensity demonstrating that reg1 narrows the distribution of total MeCP2 intensity, indicative of tighter regulation. Because local transduction efficiency varies throughout the cerebellum, the mean total MeCP2 intensity of transduced Purkinje cells vs. local transduction efficiency was plotted in FIG. 10D, where each data point represents the mean intensity and transduction efficiency for Purkinje cells within a single Z-stack. Trendlines connect Z-stacks from a single mouse. The reg1 cassette limited total MeCP2 expression, even in areas of the cerebellum with high transduction efficiency. In contrast, the negative control panel permitted total MeCP2 expression that grossly exceeds physiological levels in areas with high local transduction efficiency. FIG. 10E shows the reg1 cassette permitted transgene expression in NeuN+ cells. In contrast, the positive control for neuronal knockdown decreased the percentage of NeuN+ cells. Similarly, FIG. 11 shows preliminary data in which reg1 decreased hepatic transgene expression after intracisternal administration of AAV9/mini-MECP2-reg1 in heterozygous mosaic female mice.

Example 5: Generalized Panel Design Strategy and Experimental Studies

Figure 12:
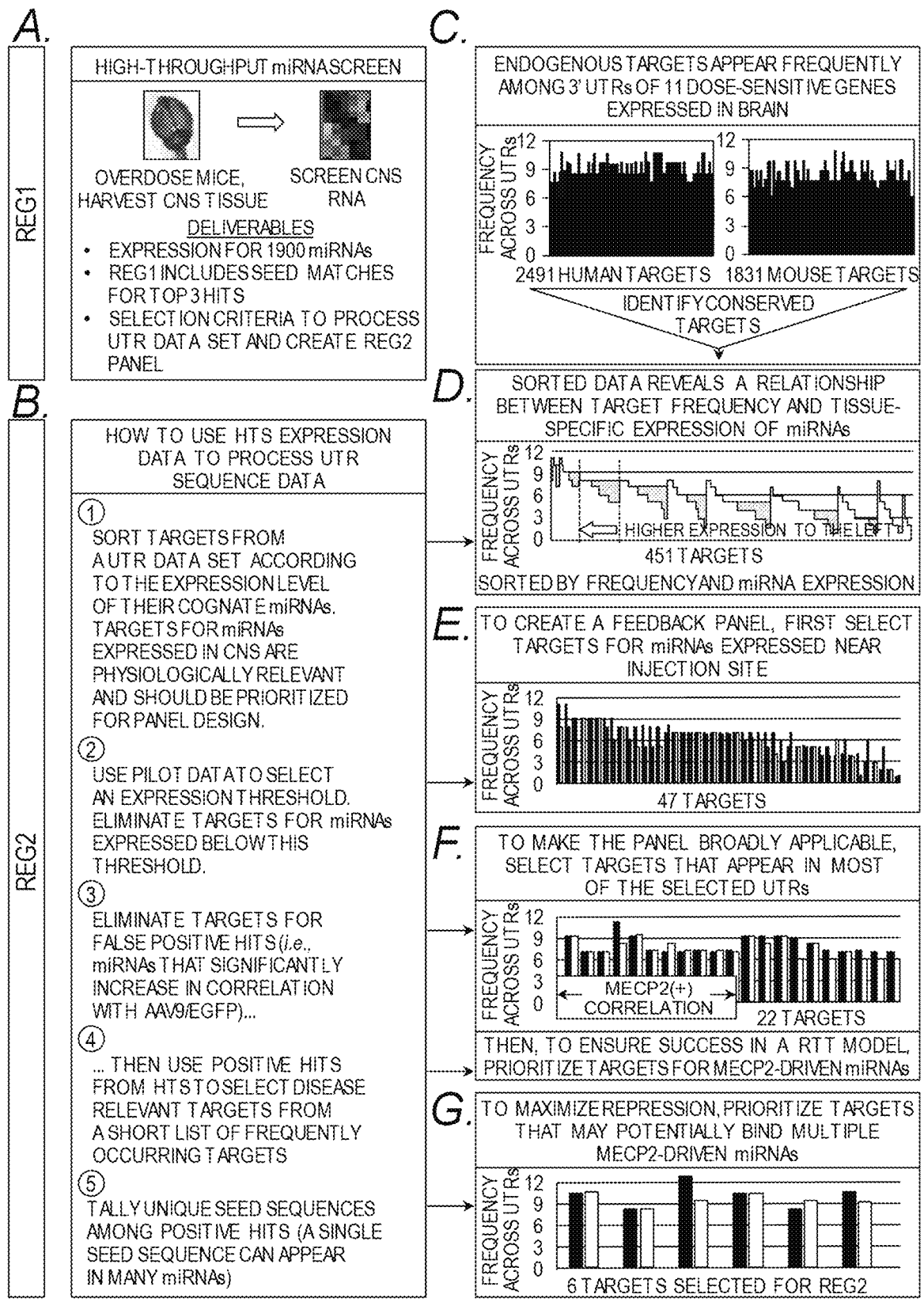
FIG. 12 summarizes strategies for designing a RTT-specific panel (referred to elsewhere as "reg1") and a broadly applicable panel (referred to elsewhere as "reg2" or "UNIVT"). Panel A shows expression data that was used to design a RTT-specific target panel for safely regulating exogenous MeCP2 expression in vivo. The same expression data provided selection criteria for processing a UTR data set for the purpose of designing reg2, as shown in Panel B. Panels C-G show steps used to narrow a list of 2491 human targets down to six conserved targets featured in reg2. Five of these targets are predicted to bind MeCP2-driven miR-NAs (see Table 1). Because the let-7 target base pairs with many let-7 miRNA seeds, it is possible that the reg2 panel may bind up to 11 miRNAs.

FIG. 12 summarizes strategies for designing the RTT-specific panel "reg1" and a broadly applicable panel (referred to elsewhere as "reg2" or "UNIVT"). FIG. 12 panel A shows microRNA expression data that was originally used to design an RTT-specific target panel for safely regulating exogenous MeCP2 expression in vivo. The same expression data provided selection criteria for processing a UTR data set for the purpose of designing reg2, as shown in FIG. 12 panel B. A list of 2491 human targets was narrowed down to six conserved targets now featured in reg2 through the steps illustrated in FIG. 12 panels C-G. Five of these targets are predicted to bind MeCP2-driven miRNAs (see Table 1). Because the let-7 target base pairs with many let-7 miRNA seeds, it is possible that the reg2 panel may bind up to 11 miRNAs. A non-limiting list of potential miRNAs that may bind the miRNA seeds included in Reg1 and/or Reg2 is shown in Table 5.

above the detection limit. Among the 3 regions examined, the hippocampus demonstrated the sharpest decrease in % myc (+) cells (reg2 vs. control-treated mice). FIG. 15B shows representative images for the thalamus, hippocampus, and medulla. FIG. 15C shows that Reg2 enhanced apparent neuronal tropism in the thalamus. FIG. 16 shows that reg2 may also improve miniMeCP2 regulation in the liver.

Figure 17:
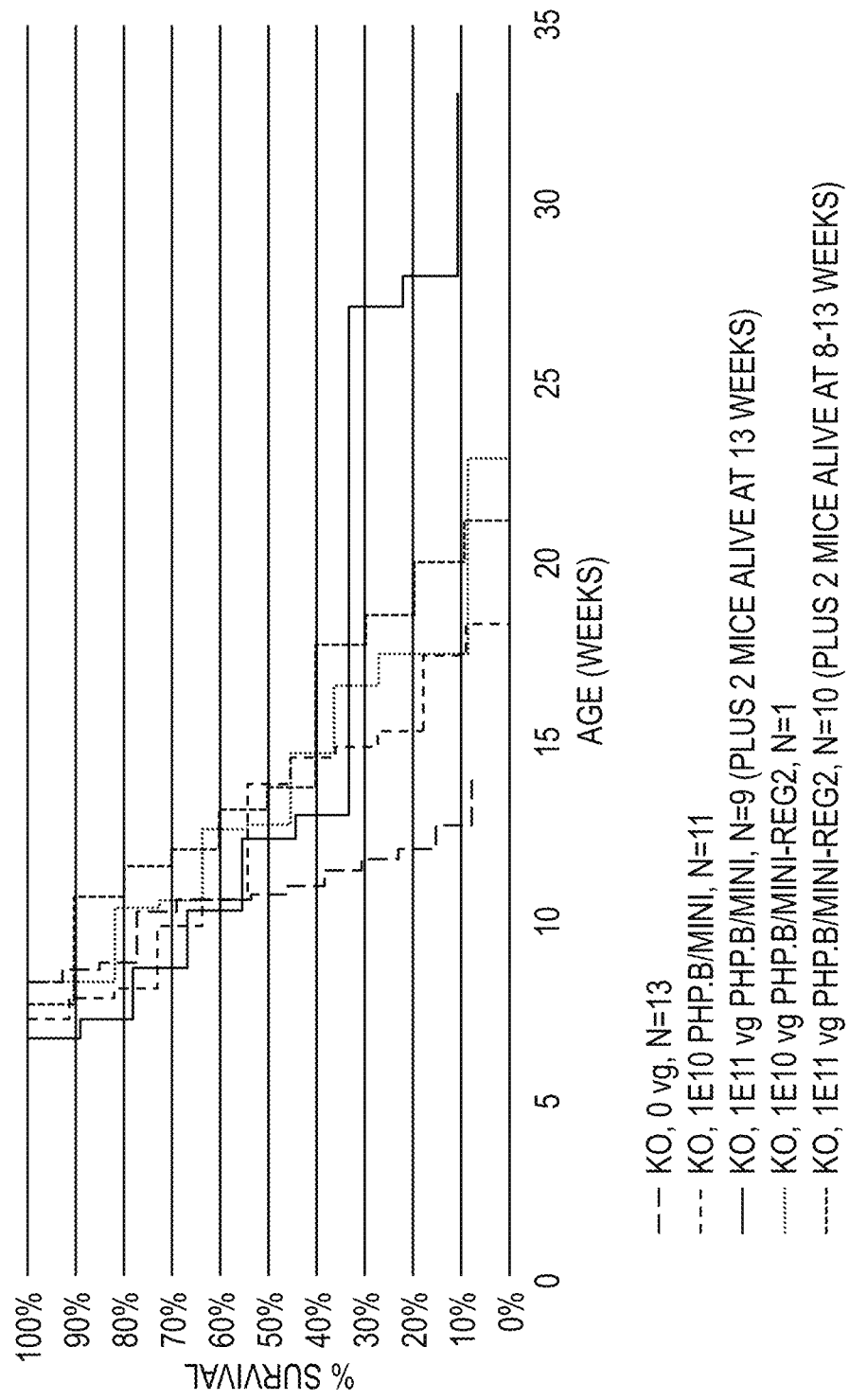
FIG. 17 shows preliminary survival data for saline- and virus-treated KO mice. Mice were injected intracisternally at 4-5 weeks of age. Although reg2 had a strong inhibitory effect on transgene expression, reg2 did not appear to attenuate the extension in median survival mediated by PHP.B/miniMECP2 (1E11 vg/mouse). Furthermore, reg2 treatments yielded fewer early deaths. The number of mice still alive in each cohort is indicated. Corresponding percentages of normal hindlimbs in treated mice is tabulated in Table 6.

Preliminary survival studies were performed in saline- and virus-treated KO mice, as shown in FIG. 17. Mice were injected intracisternally at 4-5 weeks of age. Although reg2 had a strong inhibitory effect on transgene expression, reg2

TABLE 5

MECP2-driven miRNAs and their corresponding targets in Reg1 and Reg2.

| miRNA | Endogenous MeCP2 | Exogenous MeCP2 | Aggregated MECP2(+) treatment groups | Corresponding target | Panel Design |
|---|---|---|---|---|---|
| miR-690 | Medulla | — | Cervical cord | miR-690 | Reg1 |
| miR-451a | Cervical cord | — | Medulla | miR-451a | |
| let-7e-5p | Cervical cord | — | Cervical cord | let-7-5p | Reg1 and Reg2 |
| let-7a-5p | — | — | Cervical cord | | |
| let-7b-5p | — | — | Cervical cord | | |
| let-7c-5p | — | Cervical cord | — | | |
| let-7d-5p | — | Cervical cord | — | | |
| let-7g-5p | — | Cervical cord | Cervical cord | | |
| miR-98-5p | Cervical cord | — | Cervical cord | | |
| miR-9-5p | — | — | Cervical cord | miR-9-5p | Reg2 |
| miR-218-5p | — | — | — | miR-218-5p | |
| miR-26b-5p | Cervical cord | — | Cervical cord | miR-26-5p | |
| miR-23a-3p | — | Cervical cord | — | miR-23-3p | |
| miR-27a-3p | — | — | Cervical cord | miR-27-3p | |

Correlations between miRNA expression vs. endogenous MeCP2 expression, exogenous MeCP2 expression, and/or aggregated (endogenous and exogenous) MeCP2 expression are identified. In addition, it is conceptually possible that there are miRNAs yet to be identified that could contribute to the MeCP2 feedback loop. Any miRNA containing a seed sequence permitting Watson-Crick (WC) base-pairing between the miRNA seed and the miRNA target panel may help mediate exogenous MeCP2 regulation.

Figure 13:
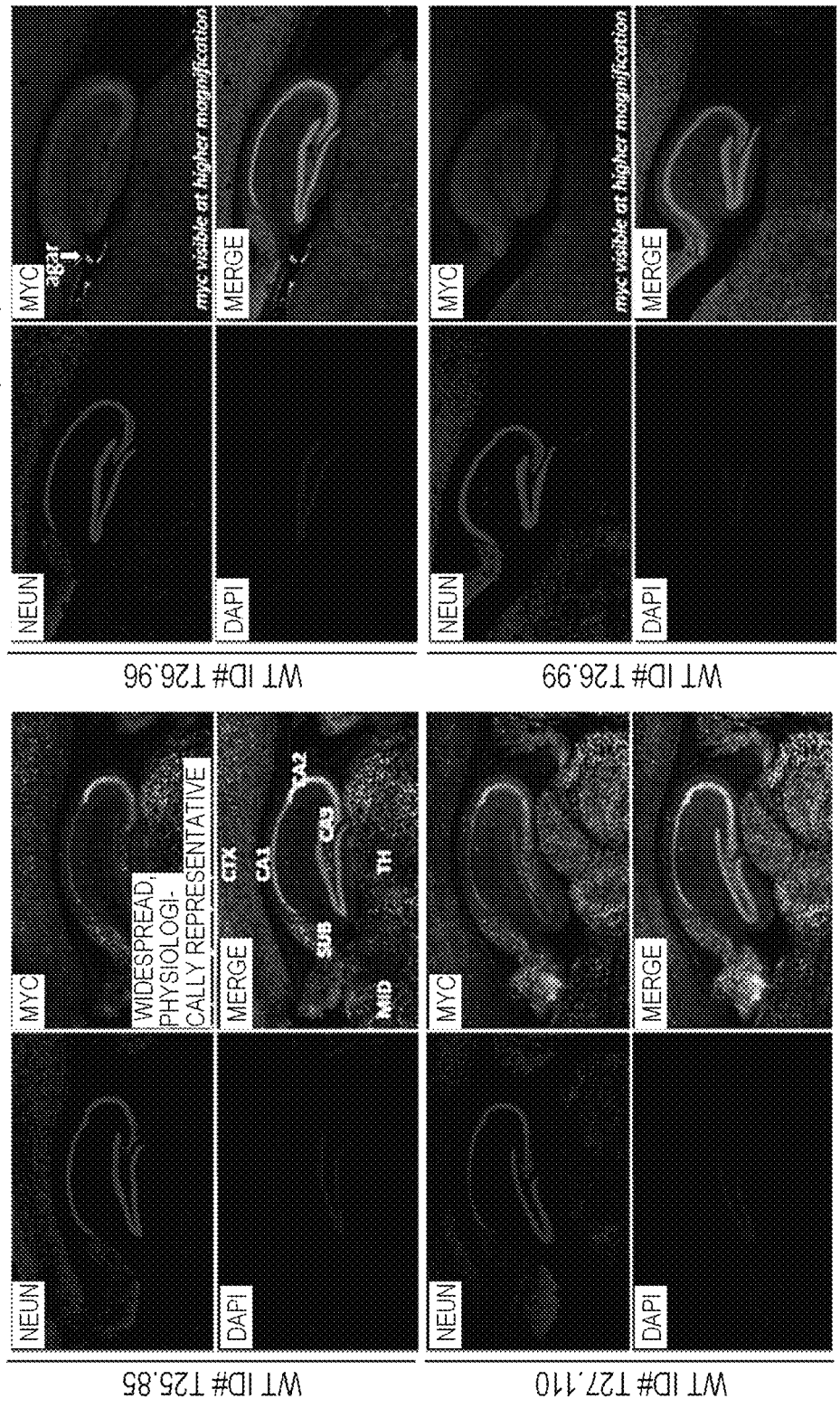
FIG. 13 shows that reg2 decreases transgene expression levels in WT brain after PHP.B-mediated miniMECP2 gene transfer. Acronyms shown in figure include CA1-3, regions of hippocampus; CTX, cortex; MID, midbrain; SUB, subiculum; TH, thalamus. Gain settings for experimental images were matched to those of control images. Each quadrant depicts one mouse, as indicated by ID number (ID #).
Figure 14:
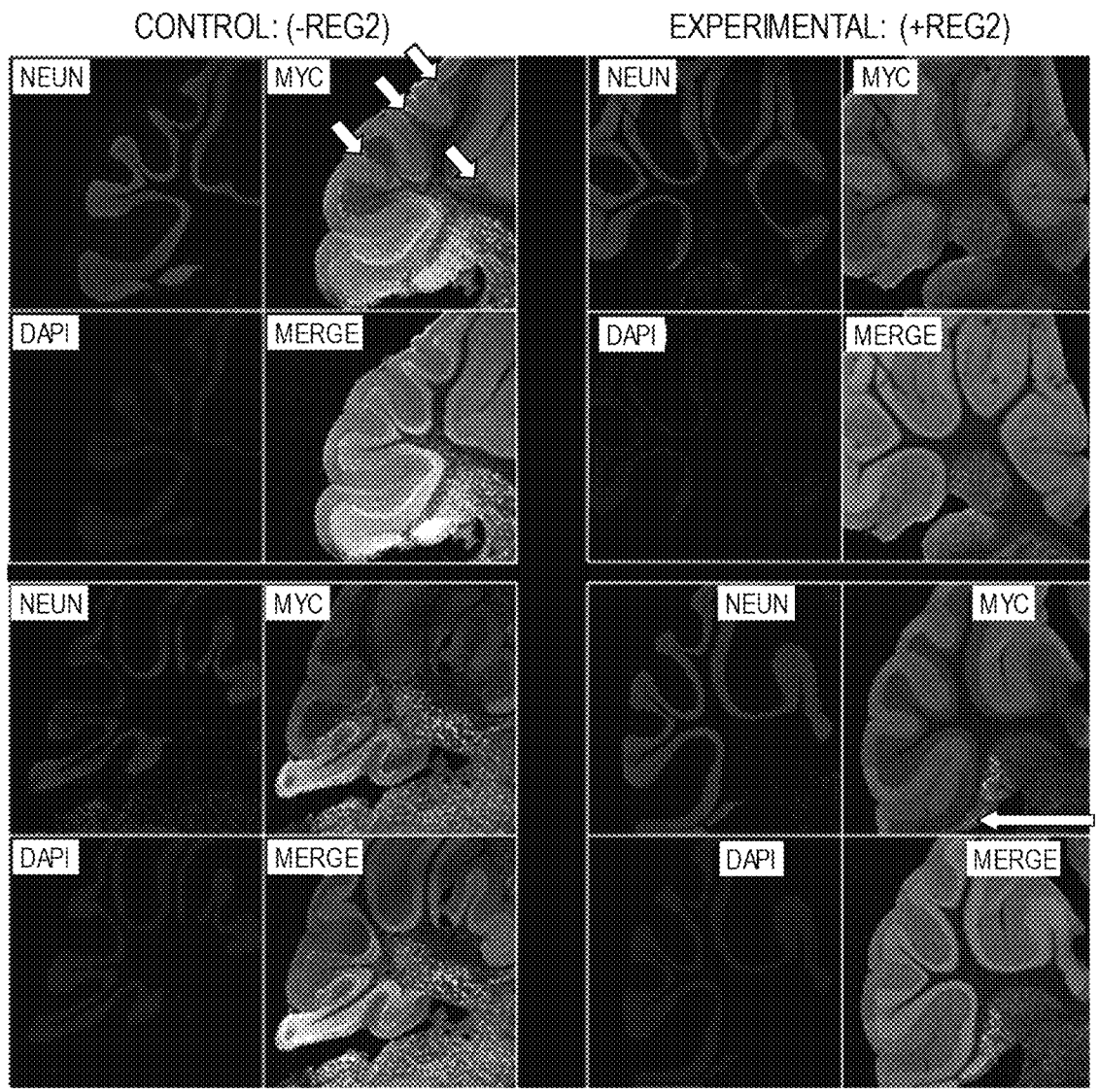
FIG. 14 shows reg2-dependent inhibition of miniMeCP2 expression in Purkinje cells within representative cerebellar tile scans. On the left (control: (−reg2)), arrows point to myc(+) Purkinje neurons in several cerebellar lobes of control vector-treated mice. In reg2-treated mice, most Purkinje cells were myc(−). On the right (Experimental: (+reg2)), the arrow indicates miniMeCP2 expression limited to the vestibulocerebellar region. Because reg2-treated mice had wide swaths of Purkinje cell layers that were either 0% myc(+) or 100% myc(+) (limited to the vestibulocerebellar region), quantitative analyses of total MeCP2 expression in neighboring myc(+) and myc(−) Purkinje cells was not advised. Each 2×2 tile scan depicts one mouse.

Further experimentation was pursued with both the reg1 RTT-specific construct and the reg2 broadly-applicable construct. FIG. 13 shows that reg2 decreases transgene expression levels in WT brain in vivo after PHP.B-mediated miniMECP2 gene transfer. FIG. 14 shows reg2-dependent inhibition of miniMeCP2 expression in Purkinje cells within representative cerebellar tile scans. On the left of FIG. 13, arrows point to myc(+) Purkinje neurons in several cerebellar lobes of control vector-treated mice. In reg2-treated mice, most Purkinje cells were myc(−). On the right of FIG. 13, the arrow indicates miniMeCP2 expression limited to the vestibulocerebellar region. Because reg2-treated mice had wide swaths of Purkinje cell layers that were either 0% myc(+) or 100% myc(+) (limited to the vestibulocerebellar region), quantitative analyses of total MeCP2 expression in neighboring myc(+) and myc(−) Purkinje cells was not advised.

Figure 15A:
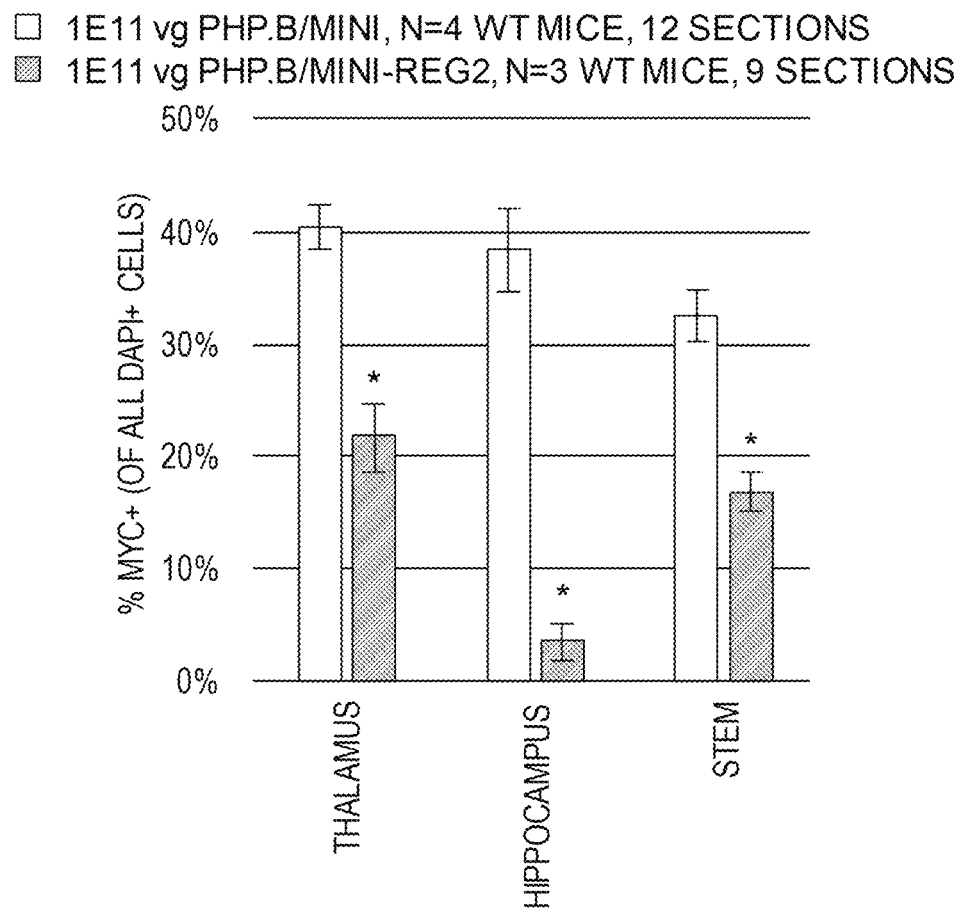
FIGS. 15A-15C show that reg2 permits widespread, but tightly controlled expression in multiple brain regions. The images shown are at a higher magnification than those shown in FIG. 13. The percentage of myc(+) cells (FIG. 15A) indicated for reg2-treated mice is likely an underestimation of the actual percentage of transduced cells, as the anti-myc immunofluorescence signal for many myc(+) cells was barely above the detection limit. Among the 3 regions examined, the hippocampus demonstrated the sharpest decrease in % myc (+) cells (reg2 vs. control-treated mice). The legend depicted in FIG. 15A also applies to FIG. 15C and FIG. 16.
Figure 15B:
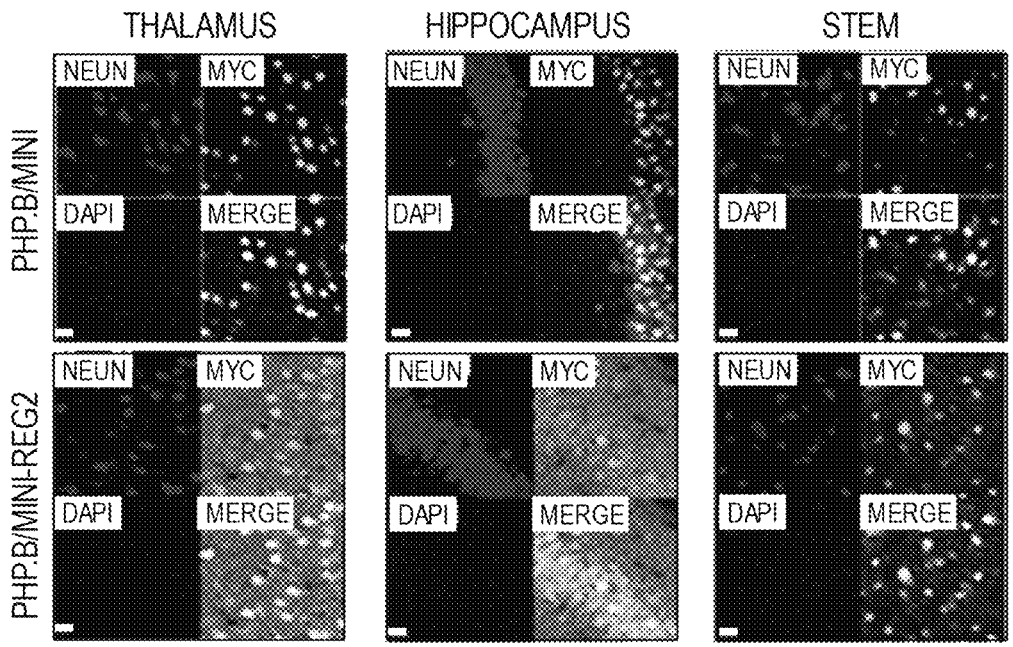
Figure 15C:
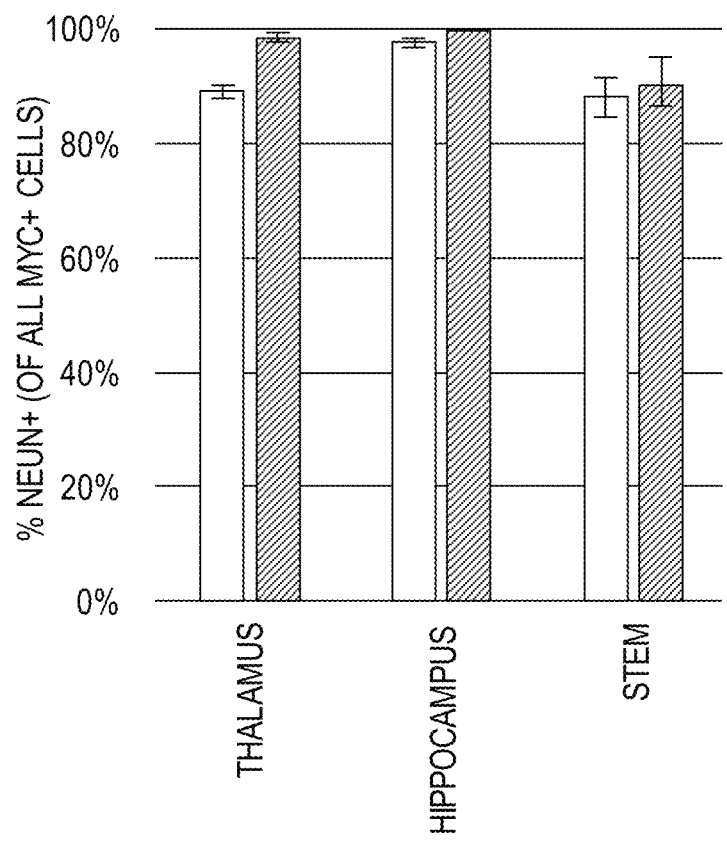
Figure 16:
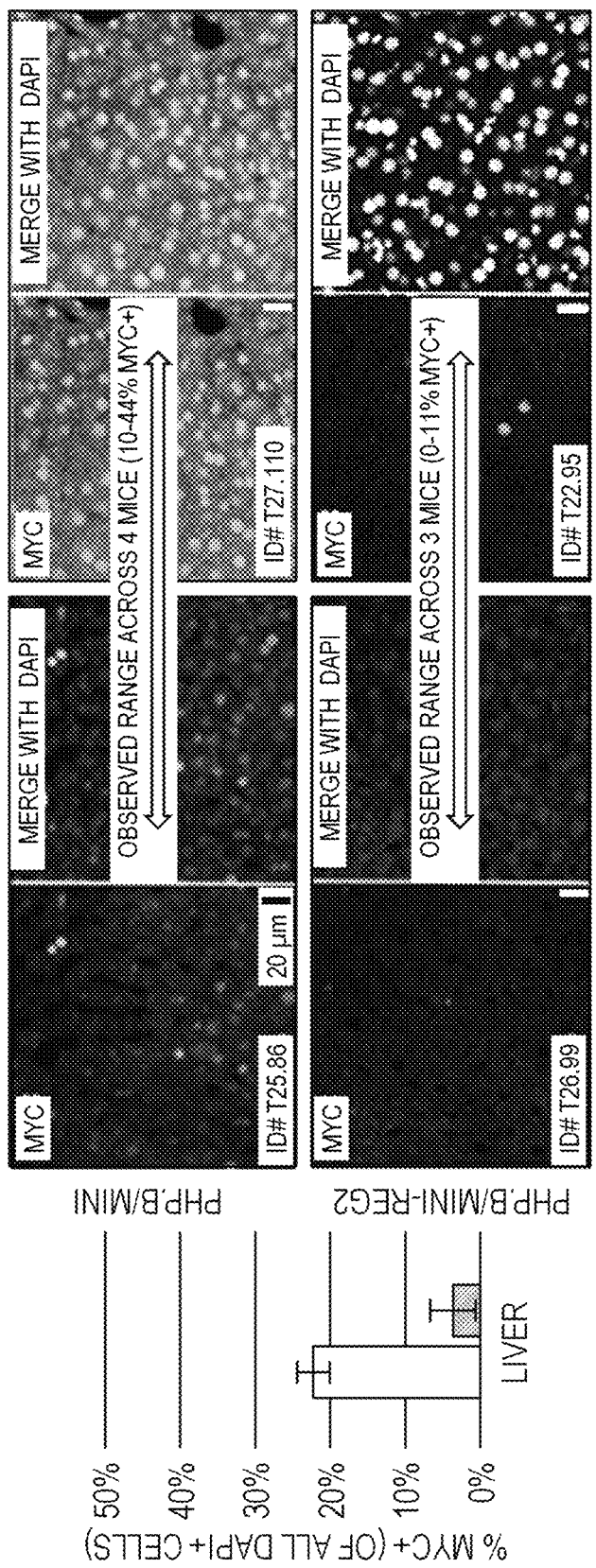
FIG. 16 shows that reg2 may improve miniMeCP2 regulation in the liver. Rather than showing representative images, the figure indicates the variability of % myc(+) hepatic cells across mice. Data are means±SEM. $p > 0.05$. The left bar graph groups correspond to the figure legend as depicted in FIG. 15A.

FIGS. 15A-15C show that reg2 permits widespread, but tightly controlled expression in multiple brain regions. The percentage of myc(+) cells in FIG. 15A indicated for reg2-treated mice were most likely an underestimation of the actual percentage of transduced cells, as the anti-myc immunofluorescence signal for many myc(+) cells was barely did not appear to attenuate the extension in median survival mediated by PHP.B/miniMECP2 (1E11 vg/mouse). Furthermore, reg2 treatments yielded fewer early deaths. The number of mice still alive in each cohort is indicated. Table 6 shows the percentage of treated KO mice that retained normal hindlimb function throughout their life span. KO mice treated with the regulated vector were more likely to retain normal hindlimb phenotypes throughout their lifespan (vs. unregulated vector).

TABLE 6

Treated KO mice retaining normal hindlimbs during survival study.

| Treatment | % (n) |
|---|---|
| Saline ICM | 38% (5/13) |
| PHP.B/mini, 1E10-1E11 vg ICM | 18% (4/22) |
| PHP.B/mini-reg2, 1E10-1E11 vg ICM | 43% (10/23) |
| AAV9/full-length MECP2 (published standard), 1E10-1E11 vg ICM | 12% (3/24) (unpublished data for mice used in studies published by Sinnett et al., 2017, MTMCD) |

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A synthetic gene comprising: a polynucleotide comprising a coding region encoding MECP2 and one or more regulatory regions, wherein the one or more regulatory regions comprise the nucleotide sequence of SEQ ID NO:2.

2. A vector comprising the synthetic gene of claim 1.

3. The vector of claim 2, wherein the vector is a viral vector.

4. The vector of claim 2, wherein the vector is an adeno-associated virus (AAV) vector.

5. The vector of claim 4, wherein the AAV vector is an AAV9 vector.

6. A pharmaceutical composition comprising the synthetic gene of claim 1 and a pharmaceutically acceptable carrier.

7. A method of delivering a synthetic gene to a subject, the method comprising administering to the subject the synthetic gene of claim 1, thereby delivering the synthetic gene to the subject.

8. A polynucleotide target cassette for providing dose dependent inhibitory feedback to a synthetic gene, the cassette comprising a regulatory region comprising the sequence of SEQ ID NO:2.

9. A method of preparing a synthetic gene comprising a polynucleotide comprising a coding region encoding MECP2 and one or more regulatory regions, comprising the step of inserting the polynucleotide target cassette of claim 8 into a regulatory region of the synthetic gene.

* * * * *

UNITED STATES PATENT AND TRADEMARK OFFICE
CERTIFICATE OF CORRECTION

PATENT NO. : 12,311,034 B2
APPLICATION NO. : 17/271432
DATED : May 27, 2025
INVENTOR(S) : Gray et al.

Page 1 of 4

It is certified that error appears in the above-identified patent and that said Letters Patent is hereby corrected as shown below:

In the Specification

Column 21, Line 39: Please insert a paragraph break between "subject." and "In some"

Column 30, Line 45: Please correct "Mullegamna" to read --Mullegama--

Signed and Sealed this
Fourteenth Day of October, 2025

John A. Squires
*Director of the United States Patent and Trademark Office*

Column 31-Column 36, Table 3: Please delete Table 3 and replace with the following:

Table 3. Assessment of miRNA targets and their human genomic context.

| GENE | 5' flanking sequence | miR-9-5p target | 3' flanking sequence |
|---|---|---|---|
| MECP2 | CUCCUGGCACU- (SEQ ID NO:3) (36% AU) | ACCAAAG- | GACACUUAUCCA (SEQ ID NO:4) (58% AU) |
| UBE3A | CUGUUCUAGCCC (SEQ ID NO:5) (42% AU; WC M12-M15) | -CCAAAGA | -GUUUCUGUGC (SEQ ID NO:6) (55% AU) |
| DYRK1A | UAAUUUAUUGU- (SEQ ID NO:7) (91% AU) | ACCAAAG- | CUGUUUUUAUAG (SEQ ID NO:8) (75% AU) |
| MEF2C | AAUAUGUUUUA- (SEQ ID NO:9) (91% AU) | ACCAAAGA | -UGUGGAGCAAU (SEQ ID NO:10) (55% AU) |
| MBD5 | CAUUUGCAUUAG (SEQ ID NO:11) (67% AU) | -CCAAAGA | -GAUAAGAACAU (SEQ ID NO:12) (73% AU) |
| ZEB2 | GGGGAAAAAAC- (SEQ ID NO:13) (55% AU) | ACCAAAGA | -AUUCACAUGGG (SEQ ID NO:14) (55% AU) |
| TCF4 | UUUAUGAAAUUU (SEQ ID NO:15) (92% AU) | -CCAAAGA | -UUUUGGUUGAU (SEQ ID NO:16) (73% AU) |
| vg | CTGTTCTAGCCC (SEQ ID NO:17) (42% AT; WC M12-M15) | -CCAAAGA | -GTTTTCTGTGC (SEQ ID NO:18) (55% AT) |
| GENE | 5' flanking sequence | miR-26-5p target | 3' flanking sequence |
| MECP2 | -AGGCUUGCAGA (SEQ ID NO:19) (45% AU) | -ACUUGAA | GCCUGCUCCUU (SEQ ID NO:20) (36% AU) |
| UBE3A | -UUGCUUUUGAA (SEQ ID NO:21) (73% AU) | -ACUUGAA | GUCUUGAAAAC (SEQ ID NO:22) (64% AU) |
| DYRK1A | -UUUUUUUUUA (SEQ ID NO:23) (100% AU) | -ACUUGAA | AAGAUUGCAAA (SEQ ID NO:24) (73% AU) |
| MEF2C | -AAGAAGAAGCC (SEQ ID NO:25) (55% AU) | -ACUUGAA | CCCUCAAUAAA (SEQ ID NO:26) (64% AU) |
| NSD1 | -GAGGUUGAGAC (SEQ ID NO:27) (45% AU) | -ACUUGAA | CUCAGGCAGAG (SEQ ID NO:28) (36% AU) |
| ATRX | ACAAUUUUGGU- (SEQ ID NO:29) (73% AU) | UACUUGAA | UUGUUAAAGAA (SEQ ID NO:30) (82% AU) |
| MBD5 | -AAAAGAAAACA (SEQ ID NO:31) (82% AU) | -ACUUGAA | CAUUUUCAAUA (SEQ ID NO:32) (82% AU) |
| ZEB2 | -UCUGUGAAGGA (SEQ ID NO:33) (55% AU) | -ACUUGAA | GUGAUGCAUGU (SEQ ID NO:34) (55% AU) |
| TCF4 | -UUUCUCAUGGG (SEQ ID NO:35) (55% AU) | -ACUUGAA | GUGGACUCAUC (SEQ ID NO:36) (45% AU) |
| vg | -TTGCTTTTGAA (SEQ ID NO:37) (73% AT) | -ACTTGAA | GTCTTGAAAAC (SEQ ID NO:38) (64% AT) |
| GENE | 5' flanking sequence | miR-23-3p target | 3' flanking sequence |
| MECP2 | -UUUUUUAAUAC (SEQ ID NO:39) (91% AU) | -AUGUGAA | -AGCAAAGAAUA (SEQ ID NO:40) (73% AU) |
| UBE3A | -AAACAAAAAGC (SEQ ID NO:41) (73% AU) | -AUGUGAA | -AGUGCACUUAA (SEQ ID NO:42) (64% AU) |
| DYRK1A | AACACUAUGUA- (SEQ ID NO:43) (73% AU) | AAUGUGAA | -UGGAAACUUGG (SEQ ID NO:44) (55% AU) |

| GENE | 5' flanking sequence | miR target | 3' flanking sequence |
|---|---|---|---|
| MEF2C | CCUUCUCUUGG- (SEQ ID NO:45) (45% AU) | AAUGUGAA | -GAUCUGUCGAU (SEQ ID NO:46) (55% AU) |
| NSD1 | -UUUCCAAAGGG (SEQ ID NO:47) (55% AU; WC M14-M16) | -AUGUGAA | -UUGGAGUGAAA (SEQ ID NO:48) (64% AU) |
| ATRX | -CAAAGACAUAG (SEQ ID NO:49) (64% AU) | -AUGUGAA | -AAUUUUAGGCA (SEQ ID NO:50) (73% AU) |
| RPS6KA3 | CAGCUGGUUCC- (SEQ ID NO:51) (36% AU) | AAUGUGA- | CUGAGUGUUCUC (SEQ ID NO:52) (50% AU) |
| MBD5 | AAGUAAGAAAA- (SEQ ID NO:53) (82% AU) | AAUGUGAA | -ACAAAUGUAGA (SEQ ID NO:54) (73% AU) |
| ZEB2 | -UUAUGACAUAU (SEQ ID NO:55) (82% AU) | -AUGUGAA | -CACAUCACAAA (SEQ ID NO:56) (64% AU) |
| TCF4 | -AUUUGGUUCAC (SEQ ID NO:57) (64% AU) | -AUGUGAA | -GUGCCCUCCAU (SEQ ID NO:58) (36% AU) |
| vg | -CAAAGACAT<u>A</u>G (SEQ ID NO:59) (64% AT) | -ATGTGA<u>A</u> | -AATTTTAGGCA (SEQ ID NO:60) (73% AT) |
| GENE | 5' flanking sequence | miR-218-5p target | 3' flanking sequence |
| MECP2 | UUCUUACCGAC- (SEQ ID NO:61) (55% AU; WC M12-M14) | AAGCACA- | GUCAGGUUGAAG (SEQ ID NO:62) (50% AU) |
| UBE3A | AACUUUAGUAAC (SEQ ID NO:63) (75% AU; WC M12-M15) | -AGCACAA | -CAAAUUAAAAA (SEQ ID NO:64) (91% AU) |
| MEF2C | UUAAUGAGAAG- (SEQ ID NO:65) (73% AU) | AAGCACAA | -UUUUGAUUUUG (SEQ ID NO:66) (82% AU) |
| ATRX | GCACGAAUAUA- (SEQ ID NO:67) (64% AU) | AAGCACA- | UCUCUUAACUGC (SEQ ID NO:68) (58% AU) |
| RPS6KA3 | GUGUAAGCUGAU (SEQ ID NO:69) (58% AU; WC M15-M19) | -AGCACAA | -GUUCUGGCGAC (SEQ ID NO:70) (36% AU) |
| MBD5 | AAUAAGAAAUGU (SEQ ID NO:71) (83% AU) | -AGCACAA | -CAUAAUUUUCC (SEQ ID NO:72) (73% AU) |
| ZEB2 | AUUUAUACUUU- (SEQ ID NO:73) (91% AU; WC M15-M17) | AAGCACAA | -CUAGAAAAUUG (SEQ ID NO:74) (73% AU) |
| TCF4 | UCAGCAUAAAC- (SEQ ID NO:75) (64% AU) | AAGCACAA | -AAAUUUAGUCU (SEQ ID NO:76) (82% AU) |
| vg | GTGTAAGCTG<u>A</u>T (SEQ ID NO:77) (58% AT; WC M15-M19) | -AGCACA<u>A</u> | -GTTCTGGCGAC (SEQ ID NO:78) (36% AT) |
| GENE | 5' flanking sequence | miR-27a-3p target | 3' flanking sequence |
| MECP2 | -GAUAAAUCUCU (SEQ ID NO:79) (73% AU) | -CUGUGAA | -AGUGA (60% AU) |
| DYRK1A | -UCACAAUUAUG (SEQ ID NO:80) (73% AU) | -CUGUGAA | -UUUUACAAAAA (SEQ ID NO:81) (91% AU) |
| MEF2C | -UUUAAAAAAAU (SEQ ID NO:82) (100% AU) | -CUGUGAA | -AUUAACAUGCU (SEQ ID NO:83) (73% AU) |
| NSD1 | UCAUGAAAUAA- (SEQ ID NO:84) (82% AU) | ACUGUGAA | -UUGGGGGGGGG (SEQ ID NO:85) (27% AU) |
| ATRX | -AAAUCAUACAG (SEQ ID NO:86) (73% AU) | -CUGUGAA | -GACUUGCCUUU (SEQ ID NO:87) (55% AU) |
| MBD5 | ACAAACCUAAA- (SEQ ID NO:88) (73% AU) | ACUGUGA- | GCCAUUGUAAA- (SEQ ID NO:89) (64% AU) |

| | | | |
|---|---|---|---|
| ZEB2 | -UUUUUUUUUU (SEQ ID NO:90) (100% AU) | -CUGUGAA | -GGAACUUGAAG (SEQ ID NO:91) (55% AU) |
| TCF4 | -UUGGGGCUUUC (SEQ ID NO:92) (45% AU) | -CUGUGAA | -AUGUAUGAACA (SEQ ID NO:93) (73% AU) |
| vg | -TCACAATTA<u>T</u>G (SEQ ID NO:94) (73% AT) | -CTGTGA<u>A</u> | -TTTTACAAAAA (SEQ ID NO:95) (91% AT) |
| GENE | 5' flanking sequence | let-7e/98-5p target | 3' flanking sequence |
| MECP2 | GUUGUUAGUUA- (SEQ ID NO:96) (73% AU) | CUACCUC- | CUCUCCUGACA- (SEQ ID NO:97) (45% AU) |
| DYRK1A | GAAGCAGUAAU- (SEQ ID NO:98) (64% AU) | CUACCUC- | UGCCGAUAACC- (SEQ ID NO:99) (45% AU) |
| MEF2C | CAAAUUGAUUCA (SEQ ID NO:100) (75% AU) | -UACCUCA | -GUUUAAUUCAG (SEQ ID NO:101) (73% AU) |
| NSD1 | UCUGCCCCUCU- (SEQ ID NO:102) (36% AU) | CUACCUC- | UUCCACUCAUG- (SEQ ID NO:103) (55% AU) |
| MBD5 | CACUGUGUGUG- (SEQ ID NO:104) (45% AU) | -UACCUCA | -GUGACCUUUUA (SEQ ID NO:105) (64% AU) |
| RPS6KA3 | GAGCCUACUUC- (SEQ ID NO:106) (45% AU) | CUACCUC- | UUAAGGCACUU- (SEQ ID NO:107) (64% AU) |
| vg | GAAGCAGTAA<u>T</u>- (SEQ ID NO:108) (64% AT) | CTACCTC | AGCCGATAACC- (SEQ ID NO:109) (45% AT) |

Column 37, Line 39: Please correct "RT" to read --RTT--